United States Patent
Sooknanan

(10) Patent No.: US 10,435,683 B2
(45) Date of Patent: Oct. 8, 2019

(54) METHODS, COMPOSITIONS, AND KITS FOR GENERATING RRNA-DEPLETED SAMPLES OR ISOLATING RRNA FROM SAMPLES

(71) Applicant: EPICENTRE TECHNOLOGIES CORPORATION, San Diego, CA (US)

(72) Inventor: Roy R. Sooknanan, Beaconsfield (CA)

(73) Assignee: EPICCENTRE TECHNOLOGIES CORPORATION, Madison, WI (US)

(*) Notice: Subject to any disclaimer, the term of this patent is extended or adjusted under 35 U.S.C. 154(b) by 236 days.

(21) Appl. No.: 15/688,600

(22) Filed: Aug. 28, 2017

(65) Prior Publication Data

US 2018/0044660 A1 Feb. 15, 2018

Related U.S. Application Data

(63) Continuation of application No. 14/223,788, filed on Mar. 24, 2014, now Pat. No. 9,745,570, which is a continuation of application No. 12/856,066, filed on Aug. 13, 2010, now abandoned.

(60) Provisional application No. 61/234,044, filed on Aug. 14, 2009.

(51) Int. Cl.
| C12Q 1/68 | (2018.01) |
| C12N 15/10 | (2006.01) |
| C07H 21/02 | (2006.01) |
| C12Q 1/6806 | (2018.01) |

(52) U.S. Cl.
CPC ....... *C12N 15/1006* (2013.01); *C12Q 1/6806* (2013.01)

(58) Field of Classification Search
CPC ... C12N 15/1006; C12Q 1/6806; C07H 21/02
See application file for complete search history.

(56) References Cited

U.S. PATENT DOCUMENTS

| 5,220,014 A | 6/1993 | Ackerman et al. |
| 5,912,148 A | 6/1999 | Eggerding |
| 6,130,073 A | 10/2000 | Eggerding |
| 6,562,575 B1 | 5/2003 | Dahl |
| 6,613,516 B1 | 9/2003 | Christians et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,170,050 B2 | 1/2007 | Turner et al. |
| 7,282,337 B1 | 10/2007 | Harris |
| 7,302,146 B2 | 11/2007 | Turner |
| 7,313,308 B2 | 12/2007 | Turner et al. |
| 7,329,492 B2 | 2/2008 | Hardin et al. |
| 7,476,503 B2 | 1/2009 | Turner et al. |
| 7,482,120 B2 | 1/2009 | Buzby |
| 7,501,245 B2 | 3/2009 | Quake et al. |
| 2003/0059789 A1 | 3/2003 | Efimov et al. |
| 2003/0175709 A1 | 9/2003 | Murphy et al. |
| 2006/0257902 A1 | 11/2006 | Mendoza et al. |
| 2007/0250274 A1 | 10/2007 | Volkov et al. |
| 2008/0241951 A1 | 10/2008 | Battulga et al. |

FOREIGN PATENT DOCUMENTS

| WO | 2001/042457 A2 | 6/2001 |
| WO | 2001/083814 A2 | 11/2001 |
| WO | 2003/054162 A2 | 7/2003 |
| WO | 2006/110314 A2 | 10/2006 |
| WO | 2007/019444 A2 | 2/2007 |

OTHER PUBLICATIONS

"Ask Frank by Fred and Hank, Production and Labeling of Antisense RNA using EPICENTRE's TargetAmp™ Kits," vol. 15-1, May 2008, 1 page.
Cook et al., "Synthesis and hybridization of a series of biotinylated oligonucleotides," Nucleic Acids Res. 1988, 16(9), 4077-4095.
Dorris et al., "A Highly Reproducible, Linear, and Automated Sample Preparation Method for DNA Microarrays," Genome Res. 2002, 976-984.
Fenn et al., "Direct Quantitation of Biotin-Labeled Nucleotide Analogs in RNA Transcripts," Analytical Biochem. 1990, 190, 78-83.
Invitrogen, Biotin-14-CTP, Cat. No. 19519-016, Dec. rev Jul. 17, 2001, 2 pages.
Invitrogen, RiboMinus™ Eukaryote Kit for RNA-Seq, Rev. date Sep. 8, 2008, 4 pages.
Lepp et al., "Methanogenic *Archaea* and human periodontal disease," PNAS 2004, 101(16), 6176-6181.
Paladichuk, "Fishing in a Molecular Sea," The Scientist Magazine, 1999, 8 pages.
Astier et al., "Toward Single Molecule DNA Sequencing: Direct Identification of Ribonucleoside and Deoxyribonucleoside 5'-Monophosphates by Using an Engineered Protein Nanopore Equipped with a Molecular Adapter," J. Am. Chem. Soc. 2006, 128(5), 1705-10.
Bauman et al., "Flow Cytometric Detection of Ribosomal RNA in Suspended Cells by Fluorescent in situ Hybridization," in Cytometry, Alan Liss, New York, US, vol. 9, No. 6, XP009084761, ISSN: 0196-4763, DOI: 10.1002/CUTO.990090602, Nov. 1, 1998, 517-524.

(Continued)

*Primary Examiner* — David C Thomas
(74) *Attorney, Agent, or Firm* — Illumina, Inc.

(57) ABSTRACT

The present invention provides methods, compositions, and kits for generating rRNA-depleted samples and for isolating rRNA from samples. In particular, the present invention provides compositions comprising affinity-tagged antisense rRNA molecules corresponding to substantially all of at least one rRNA molecule (e.g., 28S, 26S, 25S, 18S, 5.8S and 5S eukaryotic cytoplasmic rRNA molecules, 12S and 16S eukaryotic mitochondrial rRNA molecules, and 23S, 16S and 5S prokaryotic rRNA molecules) and methods for using such compositions to generate rRNA-depleted samples or to isolate rRNA molecules from samples.

18 Claims, 27 Drawing Sheets

Specification includes a Sequence Listing.

(56) References Cited

OTHER PUBLICATIONS

Binladen et al., "The use of coded PCR primers enables high-throughput sequencing of multiple homolog amplification products by 454 parallel sequencing," Plos One 2007, 2(2), E197.
Byers et al., "PolyA PCR Amplification of cDNA from RNA Extracted from Formalin-Fixed Paraffin-Embedded Tissue," Diagnostic Molecular Pathology, vol. 13, Issue 3 (abstract), Sep. 2004, 144.
Chakravorty et al., "A detailed analysis of 16S ribosomal RNA gene segments for the diagnosis of pathogenic bacteria," J. Microbiol. Methods 2007, 69, 330-339.
Delong et al., "Visualization and enumeration of marine planktonic archaea and bacteria by using polyribonucleotide probes and fluorescent in situ hybridization," Appl. Env. Microbiol. 1999, 65, 12, 5554-5563.
Emelyanov, "Evolutionary relationship of Rickettsiae and mitochondria," FEBS Lett. 2001, 501, 11-18.
EP Office Action, Application No. 10808806.3, dated Nov. 11, 2013.
Fernandez et al., "Full-length-enriched cDNA libraries from Echinococcus granulosus contain separate populations of oligo-capped and trans-spliced transcripts and a high level of predicted signal peptide sequences," Mol. Biochem. Parasitol. 2002, 122, 171-180.
Harris et al., "Single-Molecule DNA Sequencing of a Viral Genome," Science 2008, 2008, 320, 106-109 and Suppl. Materials 1-25.
Hoffmann et al., "Dna Bar Coding and Pyrosequencing to Identify Rare HIV Drug Resistance Mutations", Nucleic Acids Res. 2009, 35, e91, 2007, 8 pages.
Ingolia et al., "Genome-wide analysis in vivo of translation with nucleotide resolution using ribosome profiling," Science 2009, 324(5924), 218-223.
Invitrogen Corp, "RiboMinus Transcriptome Isolation Kit", 2005.
Invitrogen Dynal, "Dynabeads M-280 Streptavidin," Cat. No. 11205D, Rev. No. 012: Introgen Dynal AS, 2006.
Kaminski et al., "Chapter 5, Affinity methods for isolating RNA binding proteins," in *RNA protein interactions: A practical approach*, edited by Christopher W.J. Smith. Series edited by B.D. Hames. Oxford University Press, 1998, reprinted in 2002, ISBN 0-19-963650-8.
Kong et al., "The presence of rRNA sequences in polyadenylated RNA and its potential functions," Biotechnol. J. 2008, 3, 1041-1046.
Margulies et al., "Genome sequencing in microfabricated high-density picolitre reactors," Nature 2005, 437, 376-380 and Supplemental Materials.

McGowan et al., "Acid-induced expression of an LPS-associated gene in Helicobacter pylori," Mol. Microbiol. 1998, 30, 19-31.
McGowan et al., "Promoter analysis of Helicobacter pylori genes with enhanced expression at low pH," Mol. Microbiol. 2003, 48(5), 1225-1239.
McLaughlin et al., "Whole-Genome Resequencing with Short Reads: Accurate Mutation Discovery with Mate Pairs and Quality Values," ASHG Annual Meeting, 2007.
Mehta, "RiboMinus Transcriptome Isolation Kit (Human/Mouse)," Invitrogen User Manual, Catalog Nos. K1550-02, K1550-05, Version C, Sep. 12, 2005, 40 pages.
Mikkelsen et al., "Genome-Wide Maps of Chromatin State in Pluripotent and Lineage-Committed Cells," Nature 2007, 448, 553-60.
Millar et al., "Molecular Diagnostics of Medically Important Bacterial Infections," Curr. Issues Mol. Biol. 2007, 9, 21-40.
Mitsuya et al., "Minority Human Immunodeficiency Virus Type 1 Variants in Antiretroviral-Naive Persons with Reverse Transcriptase Codon 215 Revertant Mutations," J. Virol. 2008, 82, 10747-10755.
Plum et al., "Induction of *Mycobacterium avium* Gene Expression following Phagocytosis by Human Macrophages," Infect. Immun. 1994, 62(2), 476-483.
Seqanswers, "SEQanswers the next generation sequencing community", [cited Jun. 30, 2015] Available from: [http://seqanswers.com/forums/showthread.php?t=1026].
Shendure et al., "Accurate Multiplex Polony Sequencing of an Evolved Bacterial Genome," Science, 2005, 309, 1728-1732.
Simen et al., "Prevalence of Low Abundance Drug Resistant Variants by Ultra Deep Sequencing in Chronically HIV-infected Antiretroviral (ARV) Naïve Patients and the Impact on Virologic Outcomes," 16th International HIV Drug Resistance Workshop, Barbados, 2007, 23.
Stewart et al., "Development and quantitative analyses of a universal rRNA-subtraction protocol for microbial metatranscriptomics," ISME J. 2010, 4, 896-907.
Stoffels et al., "rRNA probe-based cell fishing of bacteria," Environmental Microbiology, Blackwell Science, Oxford, UK, vol. 1., No. 3, XP002246085, ISSN: 1462-2912, DOI, 10.1046/J 1462-2920.1999.00032.X, (Jun. 1, 1999), 256-271.
Stratagene, "RNAMaxx High Yield Transcription Kit," Catalog #200339 Revision A, 2009.
Su et al., "A Simple Method to Enrich mRNA from Total Prokaryotic RNA," Mol. Biotechnol. 1998, 10(1), 83-85.
Thomas et al., "Sensitive Mutation Detection in Heterogeneous Cancer Specimens by Massively Parallel Picoliter Reactor Sequencing," Nature Med. 2006, 12, 852-855.
Voelkerding et al., "Next-Generation Sequencing: From Basic Research to Diagnostics," Clin. Chem. 2009, 55(4), 641-658.

```
                            SEQUENCE LISTING

<160> NUMBER OF SEQ ID NOS: 72

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
cctacctacc tggttgatcc                                                  20

<210> SEQ ID NO 2
<211> LENGTH: 51
<212> TYPE: DNA
<213> ORGANISM: Artificial Sequence
<220> FEATURE:
<223> OTHER INFORMATION: Synthetic

<400> SEQUENCE: 2
aattctaata cgactcacta tagggagaga tccttccgca ggttcaccta c               51

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
cgactcttag cggtggatca ctc                                              23

<210> SEQ ID NO 4
<211> LENGTH: 51
<212> TYPE: DNA
<213> ORGANISM: Artificial Sequence
<220> FEATURE:
<223> OTHER INFORMATION: Synthetic

<400> SEQUENCE: 4
aattctaata cgactcacta tagggagaga tccttccgca ggttcaccta c               51

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
gtctacggcc ataccaccct gaa                                              23

<210> SEQ ID NO 6
<211> LENGTH: 50
<212> TYPE: DNA
<213> ORGANISM: Artificial Sequence
<220> FEATURE:
<223> OTHER INFORMATION: Synthetic

<400> SEQUENCE: 6
aattctaata cgactcacta tagggagaaa gcctacagca cccggtattc                 50
```

```
<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
aagcgactaa gcgtacacgg tgga                                          24

<210> SEQ ID NO 8
<211> LENGTH: 52
<212> TYPE: DNA
<213> ORGANISM: Artificial Sequence
<220> FEATURE:
<223> OTHER INFORMATION: Synthetic

<400> SEQUENCE: 8
aattctaata cgactcacta tagggagatt cctggaagca gggcatttgt tg           52

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
caacaaatgc cctgcttcca ggaa                                          24

<210> SEQ ID NO 10
<211> LENGTH: 53
<212> TYPE: DNA
<213> ORGANISM: Artificial Sequence
<220> FEATURE:
<223> OTHER INFORMATION: Synthetic

<400> SEQUENCE: 10
aattctaata cgactcacta tagggagaca cggttcatta gtaccggtta gct          53

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
agagtttgat cctggctcag                                               20

<210> SEQ ID NO 12
<211> LENGTH: 50
<212> TYPE: DNA
<213> ORGANISM: Artificial Sequence
<220> FEATURE:
<223> OTHER INFORMATION: Synthetic

<400> SEQUENCE: 12
aattctaata cgactcacta tagggagagg aggtgatcca accgcaggtt              50

<210> SEQ ID NO 13
<211> LENGTH: 22
<212> TYPE: DNA
<213> ORGANISM: Artificial Sequence
<220> FEATURE:
<223> OTHER INFORMATION: Synthetic
```

<400> SEQUENCE: 13
tgcctggcgg cagtagcgcg gt                                          22

<210> SEQ ID NO 14
<211> LENGTH: 50
<212> TYPE: DNA
<213> ORGANISM: Artificial Sequence
<220> FEATURE:
<223> OTHER INFORMATION: Synthetic

<400> SEQUENCE: 14
aattctaata cgactcacta tagggagatg cctggcagtt ccctactctc            50

<210> SEQ ID NO 15
<211> LENGTH: 22
<212> TYPE: DNA
<213> ORGANISM: Artificial Sequence
<220> FEATURE:
<223> OTHER INFORMATION: Synthetic

<400> SEQUENCE: 15
gacgtgctaa tctgcgataa gc                                          22

<210> SEQ ID NO 16
<211> LENGTH: 27
<212> TYPE: DNA
<213> ORGANISM: Artificial Sequence
<220> FEATURE:
<223> OTHER INFORMATION: Synthetic

<400> SEQUENCE: 16
atggattcag ttaatgatag tgtgtcg                                     27

<210> SEQ ID NO 17
<211> LENGTH: 27
<212> TYPE: DNA
<213> ORGANISM: Artificial Sequence
<220> FEATURE:
<223> OTHER INFORMATION: Synthetic

<400> SEQUENCE: 17
ctgaaagcat ctaagcacga aacttgc                                     27

<210> SEQ ID NO 18
<211> LENGTH: 24
<212> TYPE: DNA
<213> ORGANISM: Artificial Sequence
<220> FEATURE:
<223> OTHER INFORMATION: Synthetic

<400> SEQUENCE: 18
cctatcaacg tcgtcgtctt caac                                        24

<210> SEQ ID NO 19
<211> LENGTH: 22
<212> TYPE: DNA
<213> ORGANISM: Artificial Sequence
<220> FEATURE:
<223> OTHER INFORMATION: Synthetic

<400> SEQUENCE: 19
gcctaacaca tgcaagtcga ac                                          22

```
<210> SEQ ID NO 20
<211> LENGTH: 24
<212> TYPE: DNA
<213> ORGANISM: Artificial Sequence
<220> FEATURE:
<223> OTHER INFORMATION: Synthetic

<400> SEQUENCE: 20
agctaccgtt tccagtagtt atcc                                          24

<210> SEQ ID NO 21
<211> LENGTH: 23
<212> TYPE: DNA
<213> ORGANISM: Artificial Sequence
<220> FEATURE:
<223> OTHER INFORMATION: Synthetic

<400> SEQUENCE: 21
cggaatcgct agtaatcgtg gat                                           23

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
tcccgaaggt taagctacct actt                                          24

<210> SEQ ID NO 23
<211> LENGTH: 22
<212> TYPE: DNA
<213> ORGANISM: Artificial Sequence
<220> FEATURE:
<223> OTHER INFORMATION: Synthetic

<400> SEQUENCE: 23
tgcctggcag ttccctactc tc                                            22

<210> SEQ ID NO 24
<211> LENGTH: 24
<212> TYPE: DNA
<213> ORGANISM: Artificial Sequence
<220> FEATURE:
<223> OTHER INFORMATION: Synthetic

<400> SEQUENCE: 24
accaggttaa cccgtatgtt ggct                                          24

<210> SEQ ID NO 25
<211> LENGTH: 24
<212> TYPE: DNA
<213> ORGANISM: Artificial Sequence
<220> FEATURE:
<223> OTHER INFORMATION: Synthetic

<400> SEQUENCE: 25
accgatgttg ttggtccact ggta                                          24

<210> SEQ ID NO 26
<211> LENGTH: 20
<212> TYPE: DNA
<213> ORGANISM: Artificial Sequence
<220> FEATURE:
<223> OTHER INFORMATION: Synthetic
```

<400> SEQUENCE: 26
ctcagtaacg gcgagtgaac        20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
gcctcgatca gaaggacttg        20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
taccacaggg ataactggct        20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
taggaagagc cgacatcgaa        20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
cctacctggt tgatcctgcc        20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
ccaagtagga gaggagcgag        20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
cccagtaagt gcgggtcata        20

<210> SEQ ID NO 33
<211> LENGTH: 25
<212> TYPE: DNA
<213> ORGANISM: Artificial Sequence
<220> FEATURE:
<223> OTHER INFORMATION: Synthetic

<400> SEQUENCE: 33
tcactaaacc atccaatcgg tagta                                         25

<210> SEQ ID NO 34
<211> LENGTH: 23
<212> TYPE: DNA
<213> ORGANISM: Artificial Sequence
<220> FEATURE:
<223> OTHER INFORMATION: Synthetic

<400> SEQUENCE: 34
gatccttccg caggttcacc tac                                           23

<210> SEQ ID NO 35
<211> LENGTH: 22
<212> TYPE: DNA
<213> ORGANISM: Artificial Sequence
<220> FEATURE:
<223> OTHER INFORMATION: Synthetic

<400> SEQUENCE: 35
aagcctacag cacccggtat tc                                            22

<210> SEQ ID NO 36
<211> LENGTH: 24
<212> TYPE: DNA
<213> ORGANISM: Artificial Sequence
<220> FEATURE:
<223> OTHER INFORMATION: Synthetic

<400> SEQUENCE: 36
tcgacagtca gccgcatctt cttt                                          24

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
accaaatccg ttgactccga cctt                                          24

<210> SEQ ID NO 38
<211> LENGTH: 25
<212> TYPE: DNA
<213> ORGANISM: Artificial Sequence
<220> FEATURE:
<223> OTHER INFORMATION: Synthetic

<400> SEQUENCE: 38
cacaagagga agagagagac cctca                                         25

<210> SEQ ID NO 39
<211> LENGTH: 24
<212> TYPE: DNA
<213> ORGANISM: Artificial Sequence
<220> FEATURE:
<223> OTHER INFORMATION: Synthetic

<400> SEQUENCE: 39
ttgatggtac atgacaaggt gcgg                                             24

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
gaatcaccga cctctctccc                                                  20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
cgactctcat aacgacccgc                                                  20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
ccagaggtga ccactttcaa                                                  20

<210> SEQ ID NO 43
<211> LENGTH: 21
<212> TYPE: DNA
<213> ORGANISM: Artificial Sequence
<220> FEATURE:
<223> OTHER INFORMATION: Synthetic

<400> SEQUENCE: 43
atgtggaaca gagccttcct c                                                21

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
cacgttttct cagctgcttg                                                  20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
ttcacctttt catccaaggc                                                  20

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
gtgtggtggt gtgtgcctat                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
gagacatggt cttgctccgt                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
tagctcagtg gtagagcgca                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
gatttgctca gcagcacgta                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
cacttgggga cactttccag                                              20

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
tcagggaaaa tgagccaatc                                              20

<210> SEQ ID NO 52
<211> LENGTH: 19
<212> TYPE: DNA
<213> ORGANISM: Artificial Sequence
<220> FEATURE:
<223> OTHER INFORMATION: Synthetic

<400> SEQUENCE: 52
cttagaggga caagtggcg                                                    19

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
gtagggtagg cacacgctga                                                   20

<210> SEQ ID NO 54
<211> LENGTH: 24
<212> TYPE: DNA
<213> ORGANISM: Artificial Sequence
<220> FEATURE:
<223> OTHER INFORMATION: Synthetic

<400> SEQUENCE: 54
gaaacttaaa ggaattgacg gaag                                              24

<210> SEQ ID NO 55
<211> LENGTH: 23
<212> TYPE: DNA
<213> ORGANISM: Artificial Sequence
<220> FEATURE:
<223> OTHER INFORMATION: Synthetic

<400> SEQUENCE: 55
gaatcgagaa agagctatca atc                                               23

<210> SEQ ID NO 56
<211> LENGTH: 21
<212> TYPE: DNA
<213> ORGANISM: Artificial Sequence
<220> FEATURE:
<223> OTHER INFORMATION: Synthetic

<400> SEQUENCE: 56
cgattggatg gtttagtgag g                                                 21

<210> SEQ ID NO 57
<211> LENGTH: 27
<212> TYPE: DNA
<213> ORGANISM: Artificial Sequence
<220> FEATURE:
<223> OTHER INFORMATION: Synthetic

<400> SEQUENCE: 57
ccttgttacg acttttactt cctctag                                           27

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
gccgaaacga tctcaaccta                                                   20

```
<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
cgccagttct gcttaccaaa                                               20

<210> SEQ ID NO 60
<211> LENGTH: 19
<212> TYPE: DNA
<213> ORGANISM: Artificial Sequence
<220> FEATURE:
<223> OTHER INFORMATION: Synthetic

<400> SEQUENCE: 60
cggaccaagg agtctaaca                                                19

<210> SEQ ID NO 61
<211> LENGTH: 23
<212> TYPE: DNA
<213> ORGANISM: Artificial Sequence
<220> FEATURE:
<223> OTHER INFORMATION: Synthetic

<400> SEQUENCE: 61
caggcatagt tcaccatctt tcg                                           23

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
ggagagggtg taaatctcgc                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
gccgacttcc cttacctaca                                               20

<210> SEQ ID NO 64
<211> LENGTH: 22
<212> TYPE: DNA
<213> ORGANISM: Artificial Sequence
<220> FEATURE:
<223> OTHER INFORMATION: Synthetic

<400> SEQUENCE: 64
gtgtcagaaa agttaccaca gg                                            22

<210> SEQ ID NO 65
<211> LENGTH: 25
<212> TYPE: DNA
<213> ORGANISM: Artificial Sequence
<220> FEATURE:
<223> OTHER INFORMATION: Synthetic
```

```
<400> SEQUENCE: 65
ggcgaattct gcttcacaat gatag                                           25

<210> SEQ ID NO 66
<211> LENGTH: 26
<212> TYPE: DNA
<213> ORGANISM: Artificial Sequence
<220> FEATURE:
<223> OTHER INFORMATION: Synthetic

<400> SEQUENCE: 66
gggagtaact atgactctct taaggt                                          26

<210> SEQ ID NO 67
<211> LENGTH: 21
<212> TYPE: DNA
<213> ORGANISM: Artificial Sequence
<220> FEATURE:
<223> OTHER INFORMATION: Synthetic

<400> SEQUENCE: 67
ttggctgtgg tttcgctgga t                                               21

<210> SEQ ID NO 68
<211> LENGTH: 21
<212> TYPE: DNA
<213> ORGANISM: Artificial Sequence
<220> FEATURE:
<223> OTHER INFORMATION: Synthetic

<400> SEQUENCE: 68
gtgaacagca gttgaacatg g                                               21

<210> SEQ ID NO 69
<211> LENGTH: 26
<212> TYPE: DNA
<213> ORGANISM: Artificial Sequence
<220> FEATURE:
<223> OTHER INFORMATION: Synthetic

<400> SEQUENCE: 69
cttcacaaag aaagagaac tctccc                                           26

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
cgactcttag cggtggatca                                                 20

<210> SEQ ID NO 71
<211> LENGTH: 17
<212> TYPE: DNA
<213> ORGANISM: Artificial Sequence
<220> FEATURE:
<223> OTHER INFORMATION: Synthetic

<400> SEQUENCE: 71
aagcgacgct cagacag                                                    17
```

```
<210> SEQ ID NO 72
<211> LENGTH: 23
<212> TYPE: DNA
<213> ORGANISM: Artificial Sequence
<220> FEATURE:
<223> OTHER INFORMATION: Synthetic

<400> SEQUENCE: 72
aaagcctaca gcacccggta ttc                                              23
```

METHODS, COMPOSITIONS, AND KITS FOR GENERATING RRNA-DEPLETED SAMPLES OR ISOLATING RRNA FROM SAMPLES

This application is a continuation of U.S. application Ser. No. 14/223,788, filed Mar. 24, 2014, which is a continuation of U.S. application Ser. No. 12/856,066, filed Aug. 13, 2010, which claims priority to U.S. Provisional Application Ser. No. 61/234,044, filed Aug. 14, 2009, the content of each of which is herein incorporated by reference in its entirety.

FIELD OF THE INVENTION

The present invention relates to methods, compositions, and kits for generating rRNA-depleted samples and for isolating rRNA from samples. In particular, the present invention provides compositions comprising affinity-tagged antisense rRNA molecules that exhibit sequences complementary to substantially all of at least one full-length rRNA molecule encoded by a rRNA gene (e.g., compositions comprising affinity-tagged antisense rRNA molecules that exhibit sequences which, either alone or in combination, are complementary to substantially all or the complete sequence of at least one rRNA molecule selected from among 28S, 26S, 25S, 18S, 5.8S and 5S eukaryotic cytoplasmic rRNA molecules, 12S and 16S eukaryotic mitochondrial rRNA molecules, and 23S, 16S and 5S prokaryotic rRNA molecules) and methods for using such compositions to generate rRNA-depleted samples or to isolate rRNA from samples.

BACKGROUND OF THE INVENTION

Since rRNA comprises about 95% to about 98% of the RNA in a cell, its presence can complicate various types of analyses of other RNA molecules of interest in a sample (e.g., gene expression analyses by arrays or microarrays, next-generation sequencing of tagged cDNA molecules made from one or more types of RNA molecules in samples (e.g., using the massively parallel digital sequencing methods referred to as "RNA-seq"), etc.). The problems caused by rRNA are especially difficult for analyses of RNA molecules of interest that are fragmented. For example, a considerable and continuing problem in the art is to find better methods for removing degraded rRNA from formalin-fixed paraffin-embedded (FFPE) tissue sections. If better methods were available to remove degraded rRNA from samples (e.g., FFPE-derived samples), it is believed that the enormous quantities of clinical specimens, for which medical outcomes of various diseases and various treatments are recorded in the medical records, would provide extremely valuable information related to identifying RNAs involved in the cause, maintenance, response, diagnosis, or prognosis of many diseases, such as cancer. Still further, better methods for removing rRNA, including degraded rRNA, from non-rRNA RNA molecules of interest would greatly improve the applicability and success of methods that comprise deliberately degrading the RNA as part of the particular method (such as the method of Ingolia et al., Science 324: 218-23, 2009, herein incorporated by reference).

SUMMARY OF THE INVENTION

The present invention provides methods, compositions, and kits for generating rRNA-depleted samples or for isolating rRNA from samples. In particular, the present invention provides methods for generating compositions comprising affinity-tagged antisense rRNA molecules, kits comprising such compositions, and methods for using such compositions to generate rRNA-depleted samples or to isolate rRNA from a sample (e.g., for further analysis and use).

In some embodiments, the present invention provides methods for generating a composition comprising affinity-tagged antisense rRNA molecules that exhibit sequences which, either alone or in combination, are complementary to the complete sequence of at least one rRNA molecule selected from among 28S, 26S, 25S, 18S, 5.8S and 5S eukaryotic cytoplasmic rRNA molecules, 12S and 16S eukaryotic mitochondrial rRNA molecules, and 23S, 16S and 5S prokaryotic rRNA molecules, wherein the composition is for use in a method for generating a rRNA-depleted sample or for isolating rRNA from a sample. In some embodiments, the composition comprises affinity-tagged antisense rRNA molecules that exhibit sequences which, either alone or in combination, are complementary to multiple different rRNA molecule selected from among 28S, 26S, 25S, 18S, 5.8S and 5S eukaryotic cytoplasmic rRNA molecules, 12S and 16S eukaryotic mitochondrial rRNA molecules, and 23S, 16S and 5S prokaryotic rRNA molecules from one or multiple cells or organisms. In some embodiments, the present invention provides methods for using the composition comprising the affinity-tagged antisense rRNA molecules for generating a rRNA-depleted sample and/or for isolating rRNA from a sample.

In some embodiments, the present invention provides a composition comprising affinity-tagged antisense rRNA molecules that, either alone or in combination, exhibit one or more sequences that are complementary to substantially all of the sequence exhibited by at least one full-length rRNA molecule selected from among 28S, 26S, 25S, 18S, 5.8S and/or 5S eukaryotic cytoplasmic rRNA molecules, and 12S and 16S eukaryotic mitochondrial rRNA molecules. In some embodiments, the present invention provides a composition comprising affinity-tagged antisense rRNA molecules that, either alone or in combination, exhibit one or more sequences that are complementary to substantially all of the sequence exhibited by the at least one full-length rRNA molecule selected from among 23S, 16S and 5S prokaryotic rRNA molecules. In particular embodiments, the at least one full-length cytoplasmic rRNA molecule includes both the 28S rRNA and the 18S rRNA (or both the 25S rRNA and the 18S rRNA, or both the 26S rRNA and the 18S rRNA) from one or multiple eukaryotic cells, tissues, organs, or organisms. In some embodiments, the at least one full-length rRNA molecule includes both the 23S rRNA and the 16S rRNA from one or multiple prokaryotic organisms. In some embodiments wherein the at least one full-length rRNA molecule includes both the 28S rRNA and the 18S rRNA (or both the 25S rRNA and the 18S rRNA, or both the 26S rRNA and the 18S rRNA) from one or multiple eukaryotic cells, tissues, organs, or organisms, the affinity-tagged antisense rRNA molecules also correspond to the 5.8S rRNA molecule and the 5S rRNA molecule from the one or multiple eukaryotic cells, tissues, organs, or organisms. In some embodiments, the affinity-tagged antisense rRNA molecules also correspond to at least one full-length rRNA molecule that includes both the 12S and 16S eukaryotic mitochondrial rRNA molecules from the one or multiple eukaryotic cells, tissues, organs, or organisms. In some embodiments, the affinity-tagged antisense rRNA molecules also correspond to at least one full-length rRNA molecule that includes both the 23S rRNA and the 16S rRNA from one or multiple prokaryotic organisms, and in some embodiments, the affinity-tagged antisense rRNA molecules also correspond to at least one full-length rRNA molecule that includes the 5S rRNA molecules from the one or multiple prokaryotic organisms. In further embodiments of any of the compositions comprising affinity-tagged antisense rRNA molecules, the compositions are substantially free of non-rRNA RNA molecules comprising the affinity tags. In further embodiments of any of the compositions comprising affinity-tagged antisense rRNA molecules, the compositions further comprise a binding matrix comprising affinity-tag-binding molecules.

In some embodiments wherein the composition comprising affinity-tagged antisense rRNA molecules corresponds to all of at least one rRNA molecule selected from among 28S, 26S, 25S, and 18S eukaryotic cytoplasmic rRNA molecules, 12S and 16S eukaryotic mitochondrial rRNA molecules, and prokaryotic 23S and 16S rRNA molecules, said affinity-tagged antisense rRNA molecules are fragmented (e.g., by controlled nuclease fragmentation or by controlled fragmentation using a divalent metal cation, such as Mg2+, and heat). In some embodiments, the composition comprising fragmented affinity-tagged antisense rRNA molecules comprises fragments ranging in size from about 3,500 nucleotides to about 240 nucleotides.

In some embodiments, the present invention provides a method for generating a composition comprising affinity-tagged antisense rRNA molecules comprising: a) generating double-stranded DNA molecules comprising an RNA polymerase promoter that directs RNA synthesis of antisense RNA corresponding to all of at least one rRNA molecule selected from among 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules; and b) contacting the double-stranded DNA molecules comprising the RNA polymerase promoter with an RNA polymerase and ribonucleoside-5'-triphosphates complementary to all of the nucleobases, including at least one pair of ribonucleoside-5'-triphosphates complementary to the same nucleobase, one of which pair comprises an affinity tag and the other of which pair does not comprise an affinity tag, and incubating under conditions wherein affinity-tagged antisense rRNA molecules are generated corresponding to substantially all of the sequence of the at least one rRNA molecule.

With respect to such methods, work conduct during the development of embodiments of the present invention determined that the concentration of the ribonucleoside-5'-triphosphate molecules comprising the affinity tag relative to the concentration of the ribonucleoside-5'-triphosphate molecules that lacked the affinity tag in the at least one pair of ribonucleoside-5'-triphosphates complementary to the same nucleobase was important for generating a composition comprising affinity-tagged antisense rRNA molecules that could be used to remove >95% of the at least one rRNA molecules from a sample, and that the relative concentration of the ribonucleoside-5'-triphosphate molecules comprising the affinity tag needed to be higher than had been previously used in the art. In some embodiments of the present method for generating a composition comprising antisense rRNA molecules, at least about 35% of the ribonucleoside-5'-triphosphate molecules comprising the at least one pair of ribonucleoside-5'-triphosphates comprise an affinity tag and about 65% of the ribonucleoside-5'-triphosphate molecules comprising the pair do not have an affinity tag. In some embodiments of this method, at least about 40% of the ribonucleoside-5'-triphosphate molecules comprising the at least one pair of ribonucleoside-5'-triphosphates have an affinity tag and about 60% of the ribonucleoside-5'-triphosphate molecules comprising the pair do not have an affinity tag. In some embodiments of this method, at least about 50% of the ribonucleoside-5'-triphosphate molecules comprising the at least one pair of ribonucleoside-5'-triphosphates have an affinity tag and about 50% of the ribonucleoside-5'-triphosphate molecules comprising the pair do not have an affinity tag. In some embodiments of this method, at least about 60% of the ribonucleoside-5'-triphosphate molecules comprising the at least one pair of ribonucleoside-5'-triphosphates have an affinity tag and about 40% of the ribonucleoside-5'-triphosphate molecules comprising the pair do not have an affinity tag. In some embodiments of this method, wherein the at least one rRNA molecule is selected from 5.8S and 5S eukaryotic cytoplasmic rRNA, and prokaryotic 5S rRNA, at least about 75% of the ribonucleoside-5'-triphosphate molecules comprising the at least one pair of ribonucleoside-5'-triphosphates have an affinity tag and 25% of the ribonucleoside-5'-triphosphate molecules comprising the pair do not have an affinity tag.

In some other embodiments, the present invention provides a method for generating a composition comprising affinity-tagged antisense rRNA molecules comprising: a) generating double-stranded DNA molecules comprising an RNA polymerase promoter that directs RNA synthesis of antisense RNA corresponding to all of at least one rRNA molecule selected from among 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules; b) contacting the double-stranded DNA molecules comprising the RNA polymerase promoter with an RNA polymerase and ribonucleoside-5'-triphosphates complementary to all of the nucleobases, including at least one ribonucleoside-5'-triphosphate that comprises an affinity-tag-reactive moiety (e.g., an allylamino group on the 5 position of uridine), and incubating under conditions wherein antisense rRNA molecules comprising the affinity-tag-reactive moiety are generated, which antisense rRNA molecules correspond to substantially all of the sequence of the at least one rRNA molecules; and c) contacting the antisense rRNA molecules comprising the affinity-tag-reactive moiety with a quantity of an affinity tag reagent (e.g., Biotin-X-X-NHS, EPICENTRE Biotechnologies, Madison, Wis.) under conditions wherein the affinity tag reagent reacts with at least a portion of the affinity-tag-reactive moieties in the antisense rRNA molecules comprising the affinity-tag-reactive moiety and affinity-tagged antisense rRNA molecules are generated.

Work conducted during the development of embodiments of the present invention found that the relative number of the affinity tags per given number of nucleobases in the affinity-tagged antisense rRNA molecules is important for generating a composition comprising affinity-tagged antisense rRNA molecules that can be used to remove >95% of the at least one rRNA molecules from a sample, and that the number of the affinity tags per given number of nucleobases in the affinity-tagged antisense rRNA molecules generated using the method varies based on the amount of the affinity-tag-reactive moieties present in the antisense rRNA molecules generated in step b), the properties and concentration of the affinity tag reagent, the reaction conditions, and the reaction time. Thus, in some embodiments of this method, 100% of the ribonucleoside-5'-triphosphate molecules comprising one particular nucleobase have an affinity-tag-reactive moiety. In some other embodiments of this method, the ribonucleoside-5'-triphosphates includes at least one pair of ribonucleoside-5'-triphosphates complementary to the same nucleobase, one of which pair comprises an affinity-tag-reactive moiety (e.g., UTP having an allylamino reactive group on the 5 position of uridine or "AA-UTP") and the other of which pair does not comprise an affinity tag. In some embodiments of this method, at least about 50% of the ribonucleoside-5'-triphosphate molecules comprising the at least one pair of ribonucleoside-5'-triphosphates have an affinity-tag-reactive moiety and about 50% of the ribonucleoside-5'-triphosphate molecules comprising the pair do not have an affinity-tag-reactive moiety. In some embodiments of this method, at least about 75% of the ribonucleoside-5'-triphosphate molecules comprising the at least one pair of ribonucleoside-5'-triphosphates have an affinity-tag-reactive moiety and 25% of the ribonucleoside-5'-triphosphate molecules comprising the pair do not have an affinity-tag-reactive moiety. In some embodiments of this method, the affinity tag reagent is a biotinylation reagent (e.g., Biotin-X-X-NHS) and the affinity tag comprises biotin. In some embodiments, the biotin is joined via a spacer arm to the nucleobase (e.g., a spacer arm joined to the allylamino group on the 5 position of uridine, e.g., from incorporation of AA-UTP).

In further embodiments, the present invention provides a method for generating a composition comprising antisense rRNA molecules comprising: a) generating double-stranded DNA molecules comprising an RNA polymerase promoter that directs RNA synthesis of antisense RNA corresponding to all of at least one rRNA molecule selected from among 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules; and b) contacting the double-stranded DNA molecules comprising the RNA polymerase promoter with an RNA polymerase and ribonucleoside-5'-triphosphates complementary to all of the nucleobases, including at least one pair of ribonucleoside-5'-triphosphates complementary to the same nucleobase, one of which pair comprises an affinity tag and the other of which pair does not comprise an affinity tag, and incubating under conditions wherein affinity-tagged antisense rRNA molecules are generated corresponding to substantially all of the sequence of the at least one rRNA molecule, wherein the affinity tags are present at a ratio of at least two affinity tags per hundred nucleobases of the affinity-tagged antisense rRNA molecules (e.g., based on fluorescence quantification of 200 ng of affinity-tagged antisense rRNA according to the instructions supplied with the Fluorescence Biotin Quantitation Kit, Pierce Biotechnology, Rockford, Ill.; Cat. #: Thermo 46610) after digestion of the affinity-tagged antisense rRNA with RNase 1 at 36° C. for 45 min and heat inactivation of the enzyme according to the RNase 1 literature provided by the manufacturer, EPICENTRE Biotechnologies, Madison, Wis.). In some other embodiments of this method, the affinity tags are present at a ratio of at least about three to five affinity tags per hundred nucleobases of the affinity-tagged antisense rRNA molecules (e.g., based on the fluorescence data obtained using the Pierce Fluorescence Biotin Quantitation Kit). In some other embodiments of this method, the affinity tags are present at a ratio of at least about four to six affinity tags per hundred nucleobases of the affinity-tagged antisense rRNA molecules (e.g., based on the fluorescence data obtained using the Pierce Fluorescence Biotin Quantitation Kit). In some other embodiments of this method, the affinity tags are present at a ratio of at least about six to eight affinity tags per hundred nucleobases of the affinity-tagged antisense rRNA molecules (e.g., based on the fluorescence data obtained using the Pierce Fluorescence Biotin Quantitation Kit). In some embodiments of this method wherein the at least one rRNA molecule is selected from among 28S, 26S, 25S, and 18S eukaryotic cytoplasmic rRNA molecules, 12S and 16S eukaryotic mitochondrial rRNA molecules, and 23S and 16S prokaryotic rRNA molecules, at least about 35% to about 50% of the ribonucleoside-5'-triphosphates comprising the at least one pair of ribonucleoside-5'-triphosphates complementary to the same nucleobase comprise the affinity tag (e.g., an affinity tag comprising biotin; e.g., biotin-16-UTP) and the affinity tags are present in the affinity-tagged antisense rRNA molecules generated at a ratio of at least about two to eight affinity tags per hundred nucleobases (e.g., based on the fluorescence data obtained using the Pierce Fluorescence Biotin Quantitation Kit). In some embodiments of this method wherein the at least one rRNA molecule is selected from among 5.8S and 5S eukaryotic rRNA molecules and 5S prokaryotic rRNA molecules, at least about 60% to about 75% of the ribonucleoside-5'-triphosphates comprising the at least one pair of ribonucleoside-5'-triphosphates complementary to the same nucleobase comprise the affinity tag (e.g., an affinity tag comprising biotin; e.g., biotin-16-UTP) and the affinity tags are present in the affinity-tagged antisense rRNA molecules generated at a ratio of at least about two to eight affinity tags per hundred nucleobases (e.g., based on the fluorescence data obtained using the Pierce Fluorescence Biotin Quantitation Kit).

In further embodiments, the present invention provides a method for generating a composition comprising antisense rRNA molecules comprising: a) generating double-stranded DNA molecules comprising an RNA polymerase promoter that directs RNA synthesis of antisense RNA corresponding to all of at least one rRNA molecule selected from among 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules; b) contacting the double-stranded DNA molecules comprising the RNA polymerase promoter with an RNA polymerase and ribonucleoside-5'-triphosphates complementary to all of the nucleobases, including at least one ribonucleoside-5'-triphosphate that comprises an affinity-tag-reactive moiety (e.g., an allylamino group on the 5 position of uridine), and incubating under conditions wherein antisense rRNA molecules comprising the affinity-tag-reactive moiety are generated, which antisense rRNA molecules correspond to substantially all of the sequence of the at least one rRNA molecules; and c) contacting the antisense rRNA molecules comprising the affinity-tag-reactive moiety with a quantity of an affinity tag reagent (e.g., Biotin-X-X-NHS, EPICENTRE Biotechnologies, Madison, Wis.) under conditions wherein the affinity tag reagent reacts with the affinity-tag-reactive moieties in the antisense rRNA molecules comprising the affinity-tag-reactive moiety and affinity-tagged antisense rRNA molecules are generated, wherein the affinity tags are present at a ratio of at least about two affinity tags per hundred nucleobases of the affinity-tagged antisense rRNA molecules (e.g., based on fluorescence quantification of RNase 1-digested affinity-tagged antisense rRNA molecules (200 nanograms) using the Fluorescence Biotin Quantitation Kit from Pierce Biotechnology, Rockford, Ill.). In some other embodiments of this method, the affinity tags are present at a ratio of at least about three to five affinity tags per hundred nucleobases of the affinity-tagged antisense rRNA molecules (e.g., based on the fluorescence data obtained using the Pierce Fluorescence Biotin Quantitation Kit). In some other embodiments of this method, the affinity tags are present at a ratio of at least about four to six affinity tags per hundred nucleobases of the affinity-tagged antisense rRNA molecules (e.g., based on the fluorescence data obtained using the Pierce Fluorescence Biotin Quantitation Kit). In some other embodiments of this method, the affinity tags are present at a ratio of at least about six to eight affinity tags per hundred nucleobases of the affinity-tagged antisense rRNA molecules (e.g., based on the fluorescence data obtained using the Pierce Fluorescence Biotin Quantitation Kit).

In some embodiments of any of the methods herein for generating affinity-tagged antisense rRNA molecules, the affinity tag comprises biotin. In some embodiments, the biotin is joined via a spacer arm to the 5 position of uridine. In some embodiments of any of these methods, the RNA polymerase is selected from among T7 RNA polymerase, T3 RNA polymerase, and SP6 RNA polymerase. In some embodiments of any of these methods, wherein the at least one rRNA molecule is selected from among eukaryotic cytoplasmic 25S, 26S, and 28S rRNA molecules, the RNA polymerase is SP6 RNA polymerase. In some embodiments of any of these methods, wherein the at least one rRNA molecule is a prokaryotic 23S rRNA, the RNA polymerase is SP6 RNA polymerase.

In certain embodiments of any of the above methods for generating affinity-tagged antisense rRNA molecules, the methods further comprise, after generating the antisense rRNA molecules, contacting the double-stranded DNA molecules comprising the RNA polymerase promoter with a DNase enzyme under conditions wherein the double-stranded DNA molecules comprising the RNA polymerase promoter are digested.

In some embodiments of any of the methods for generating affinity-tagged antisense rRNA molecules, step a) of the method (comprising "generating double-stranded DNA molecules comprising an RNA polymerase promoter that directs RNA synthesis of antisense RNA corresponding to all of at least one rRNA molecule selected from among 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules") comprises either: i) incubating the at least one rRNA molecule with a DNA polymerase and at least one primer pair under conditions wherein double-stranded DNA molecules that comprise an RNA polymerase promoter that is capable of directing RNA synthesis of antisense RNA corresponding to all of the at least one rRNA molecule are generated, wherein each said at least one primer pair comprises a forward primer and a reverse primer, wherein the reverse primer anneals to the at least one rRNA molecule and has a 5' portion that exhibits the sequence of one strand of an RNA polymerase promoter and the forward primer anneals to the DNA generated from the reverse primer; or: ii) incubating the at least one rRNA molecule with a DNA polymerase and at least one primer pair under conditions wherein double-stranded DNA molecules are generated, wherein each said at least one primer pair comprises a forward primer and a reverse primer, wherein the reverse primer primes DNA synthesis after annealing to the at least one rRNA molecule and the forward primer primes DNA synthesis after annealing to the DNA generated from DNA polymerase extension of the reverse primer, and then ligating said double-stranded DNA molecules generated from each at least one primer pair into a DNA vector that comprises an RNA polymerase promoter, wherein RNA polymerase promoter is capable of directing synthesis of antisense RNA that is complementary to the at least one rRNA molecule using said double-stranded DNA that is ligated into said DNA vector as a template.

In some embodiments of any of the methods for generating affinity-tagged antisense rRNA molecules, step a) of the method (comprising "generating double-stranded DNA molecules comprising an RNA polymerase promoter that directs RNA synthesis of antisense RNA corresponding to all of at least one rRNA molecule selected from among 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules") comprises obtaining a genomic DNA fragment that encodes the at least one rRNA molecule and either: i) contacting said genomic DNA fragment with a DNA polymerase and at least one primer pair, wherein the first primer of each of said at least one primer pair has a 5' portion that exhibits the sequence of one strand of an RNA polymerase promoter and a 3' portion that is complementary to a portion of a first strand of the genomic DNA fragment and the second primer of each of said at least one primer pair is complementary to a portion of the second strand of the genomic DNA fragment, and incubating under conditions wherein RNA polymerase promoter-containing double-stranded DNA copies of at least a portion of the genomic DNA fragment are generated, wherein the RNA polymerase promoter is capable of directing RNA synthesis of antisense RNA corresponding to all of the at least one rRNA molecule; or: ii) ligating said genomic DNA fragment or a PCR amplification product thereof into a DNA vector that comprises an RNA polymerase promoter to obtain a genomic clone, wherein the RNA polymerase promoter in said genomic clone is capable of directing synthesis of antisense RNA that is complementary to the at least one rRNA molecule using said double-stranded DNA that is ligated into said DNA vector as a template.

In some embodiments of the methods for generating affinity-tagged antisense rRNA molecules and of the compositions generated using the method, the affinity-tagged antisense rRNA molecules do not exhibit any rRNA internal transcribed spacer sequences. In some other embodiments, the affinity-tagged antisense rRNA molecules exhibit internal transcribed spacer sequences selected from among: i) a sequence exhibited by the ITS1 rRNA spacer region, which is located between a eukaryotic 18S rRNA gene and a eukaryotic 5.8S rRNA gene; ii) a sequence exhibited by the ITS2 rRNA spacer region, which is located between a eukaryotic 5.8S rRNA gene and a eukaryotic 28S rRNA gene; iii) a sequence exhibited by a prokaryotic 16S-23S ITS; and iv) a sequence exhibited by a prokaryotic 23S-5S rRNA ITS.

In some embodiments, the present invention provides a composition comprising affinity-tagged antisense rRNA molecules that are bound to a binding matrix comprising affinity-tag-binding molecules, wherein the affinity-tagged antisense rRNA molecules, alone or in combination, exhibit sequences corresponding to substantially all of at least one full-length rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules.

A composition comprising affinity-tagged antisense rRNA molecules that are bound to a binding matrix comprising affinity-tag-binding molecules is generated by incubating the composition comprising affinity-tagged antisense rRNA molecules with a binding matrix comprising affinity-tag-binding molecules under binding conditions, wherein the affinity tag binds to the affinity-tag-binding molecules that are attached to the matrix or solid support (e.g., microparticles) to form a specific binding pair. In some embodiments, this method further comprises the step of washing the composition under conditions wherein affinity-tagged antisense rRNA molecules that are not specifically bound to the binding matrix are removed, thereby generating a purified composition comprising affinity-tagged antisense rRNA molecules that are bound to the binding matrix.

In particular embodiments of this aspect of the invention, the composition comprising affinity-tagged antisense rRNA molecules that are bound to a binding matrix can be any composition of affinity-tagged antisense rRNA molecules described herein and can be generated using any method for generating a composition comprising antisense rRNA molecules described herein.

In one particular embodiment of this composition, the affinity-tagged antisense rRNA molecules comprise biotin as the affinity tag, wherein the biotin is joined to at least about two nucleobases per hundred nucleobases of the antisense rRNA molecules, and the binding matrix comprises a microparticle to which an affinity-tag-binding molecule comprising streptavidin or avidin is attached. In some other embodiments of this composition, the affinity-tagged antisense rRNA molecules comprise biotin as the affinity tag, wherein the biotin is joined to at least about two to four nucleobases per hundred nucleobases of the antisense rRNA molecules, or to at least three to five nucleobases per hundred nucleobases of the antisense rRNA molecules, or to at least four to six nucleobases per hundred nucleobases of the antisense rRNA molecules, or to at least six to eight nucleobases per hundred nucleobases of the antisense rRNA molecules.

In some embodiments of the invention, any of the compositions comprising affinity-tagged antisense rRNA molecules, including any of the compositions comprising affinity-tagged antisense rRNA molecules that are bound to a binding matrix, is used in a method of the invention for generating a rRNA-depleted sample or for isolating substantially all of the RNA molecules that, either alone or in combination, exhibit the sequence of at least one full-length rRNA molecule.

In some embodiments, the present invention provides methods for generating a rRNA-depleted sample from an initial sample comprising: a) providing i) an initial sample comprising RNA molecules, wherein the RNA molecules comprise rRNA molecules and at least one non-rRNA RNA molecule of interest; ii) a composition comprising affinity-tagged antisense rRNA molecules that, alone or in combination, exhibit sequences corresponding to substantially all of at least one full-length rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules; and iii) a binding matrix (e.g., microparticles) comprising affinity-tag-binding molecules; b) contacting the initial sample with the composition under conditions such that at least some of the affinity-tagged antisense rRNA molecules and at least some of the rRNA molecules form double-stranded rRNA hybrids thereby generating a treated sample; c) contacting the treated sample with the binding matrix under conditions such that at least a portion of the double-stranded rRNA hybrids bind to the binding matrix and are removed from the treated sample, thereby generating a rRNA-depleted sample, wherein the rRNA-depleted sample is substantially free of rRNA sequences exhibited by the at least one rRNA molecule and comprises substantially all of the at least one non-rRNA RNA molecule of interest present in the initial sample (e.g., at least >90% . . . , >95% . . . , >98% . . . , >99% . . . , >99.8% . . . , or >99.9% of the at least one non-rRNA RNA molecule of interest present in the initial sample).

In certain embodiments, one or more steps are repeated and/or additional methods are performed to generate the rRNA-depleted sample. In particular embodiments, the methods are performed with repeated rounds of subtraction in order to generate the rRNA-depleted sample. In particular embodiments, at least a portion of the RNA molecules in the initial sample are highly fragmented, and wherein the rRNA-depleted sample is at least 50% . . . 60% . . . 70% . . . 80% . . . 90.0% . . . 95% . . . 98% . . . 99% . . . or 100% free of rRNA sequences exhibited by the at least one rRNA molecule.

In certain embodiments, the present invention provides methods for generating a rRNA-depleted sample from an initial sample comprising: a) providing: i) an initial sample comprising RNA molecules, wherein the RNA molecules comprise rRNA molecules and at least one non-rRNA RNA molecule of interest; ii) a composition comprising affinity-tagged antisense rRNA molecules that, alone or in combination, are complementary to substantially all of the sequence exhibited by the at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules; and iii) a binding matrix (e.g., microparticles) comprising affinity-tag-binding molecules; b) contacting the initial sample with the composition under conditions such that at least some of the affinity-tagged antisense rRNA molecules and at least some of the rRNA molecules form double-stranded rRNA hybrids thereby generating a treated sample; c) contacting the treated sample with the binding matrix under conditions such that at least a portion of the double-stranded rRNA hybrids bind to the binding matrix and are removed from the treated sample, thereby generating an rRNA-depleted sample, wherein the rRNA-depleted sample comprises substantially all (e.g., >90% . . . , >95% . . . , >98% . . . , >99% . . . , >99.8% . . . , or >99.9%) of the at least one non-rRNA RNA molecule of interest present in the initial sample and is substantially free (e.g., >95% . . . , >98% . . . , >99% . . . , >99.8% . . . , or >99.9% free) of rRNA sequences exhibited by the at least one rRNA molecule present in the initial sample.

In additional embodiments, the present invention provides methods for generating a rRNA-depleted sample from an initial sample comprising: a) providing; i) an initial sample comprising RNA molecules, wherein the RNA molecules comprise rRNA molecules and at least one non-rRNA RNA molecules of interest; ii) a composition comprising affinity-tagged antisense rRNA molecules complementary to substantially all of the sequence exhibited by the at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules, wherein the affinity tags are present on the antisense rRNA molecules at a ratio of at least about two to at least four affinity-tags per hundred nucleobases of the antisense rRNA molecules; and iii) a binding matrix comprising affinity-tag-binding molecules; b) contacting the initial sample with the composition under conditions such that at least some of the affinity-tagged antisense rRNA molecules and at least some of the rRNA molecules form double-stranded rRNA hybrids thereby generating a treated sample; c) contacting the treated sample with the binding matrix under conditions wherein at least a portion of the double-stranded rRNA hybrids bind to the binding matrix and are removed from the treated sample, thereby generating a rRNA-depleted sample, wherein the rRNA-depleted sample comprises substantially all (e.g., >90% . . . , >95% . . . , >98% . . . , >99% . . . , >99.8% . . . , or >99.9%) of the at least one non-rRNA RNA molecule of interest present in the initial sample and is substantially free (e.g., >95% . . . , >98% . . . , >99% . . . , >99.8% . . . , or >99.9% free) of molecules that, either alone or in combination, exhibit the sequences within the at least one rRNA molecule present in the initial sample.

In certain embodiments, the present invention provides methods for generating a rRNA-depleted sample from an initial sample comprising: a) providing; i) an initial sample comprising RNA molecules, wherein the RNA molecules comprise rRNA molecules and at least one non-rRNA RNA molecule of interest; ii) a composition comprising affinity-tagged antisense rRNA molecules complementary to substantially all of the sequence exhibited by the at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules; and iii) a binding matrix (e.g., microparticles) comprising affinity-tag-binding molecules; b) contacting the initial sample with the composition under conditions such that at least some of the affinity-tagged antisense rRNA molecules and at least some of the rRNA molecules form double-stranded rRNA hybrids thereby generating a treated sample; c) contacting the treated sample with the binding matrix under conditions such that at least a portion of the double-stranded rRNA hybrids bind to the binding matrix and are removed from the treated sample, thereby generating a rRNA-depleted sample, wherein the rRNA-depleted sample comprises substantially all (e.g., >90% . . . , >95% . . . , >98% . . . , >99% . . . , >99.8% . . . , or >99.9%) of the at least one non-rRNA RNA molecule of interest present in the initial sample) and wherein, the rRNA-depleted sample is either: i) ≥99.0% free (e.g., >99.0%, 99.1%, 99.2%, 99.3%, 99.4%, 99.5%, 99.6%, 99.7%, 99.8%, 99.9%, 99.95%, or 99.99% free) of RNA molecules that, either alone or in combination, exhibit a sequence within the at least one rRNA molecule present in the initial sample, or ii) contains undetectable levels of the at least one rRNA molecules from the initial sample as measured using agarose gel electrophoresis and ethidium bromide staining.

In some embodiments, the present invention provides methods for generating a rRNA-depleted sample from an initial sample comprising: a) providing i) an initial sample comprising RNA molecules, wherein the RNA molecules comprise rRNA molecules and at least one non-rRNA RNA molecule of interest; and ii) a composition comprising affinity-tagged antisense rRNA molecules that are bound to a binding matrix (e.g., microparticles comprising affinity-tag-binding molecules), wherein the affinity-tagged antisense rRNA molecules, alone or in combination, exhibit sequences corresponding to substantially all of at least one full-length rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules; b) contacting the initial sample with the composition under conditions such that at least some of the affinity-tagged antisense rRNA molecules in the composition and at least some of the rRNA molecules form double-stranded rRNA hybrids that are bound to the binding matrix, thereby generating a treated sample; and c) removing the binding matrix to which the double-strand rRNA hybrids are bound, thereby generating a rRNA-depleted sample, wherein the rRNA-depleted sample is: i) substantially free of rRNA sequences exhibited by the at least one rRNA molecule and comprises substantially all of the at least one non-rRNA RNA molecule of interest present in the initial sample (e.g., at least >90% . . . , >95% . . . , >98% . . . , >99% . . . , >99.8% . . . , or >99.9% of the at least one non-rRNA RNA molecule of interest present in the initial sample), and ii) either, substantially free (e.g., >95% . . . , >98% . . . , >99% . . . , >99.8% . . . , or >99.9% free) of rRNA sequences exhibited by the at least one rRNA molecule present in the initial sample, or, contains undetectable levels of the at least one rRNA molecules from the initial sample as measured using agarose gel electrophoresis and ethidium bromide staining. In particular embodiments of this method of the invention, the composition comprising affinity-tagged antisense rRNA molecules that are bound to a binding matrix is any composition of affinity-tagged antisense rRNA molecules described herein and/or is generated using any method for generating a composition comprising antisense rRNA molecules described herein.

In particular embodiments of any of the methods for generating an rRNA-depleted sample, the rRNA-depleted sample is 98.0% free of rRNA molecules that exhibit sequences within the at least one rRNA molecule (e.g., 98.0% free, 98.5% free, 99.0% free, 99.5% free, 99.7% free, 99.9% free, 99.99% free, or 100% free). In other embodiments, the at least one rRNA molecule includes both the 28S rRNA and the 18S rRNA, and wherein the rRNA-depleted sample is 99.0% free (e.g., 99.5% free) of rRNA molecules that exhibit sequences within the 28S rRNA gene and the 18S rRNA gene. In other embodiments, the rRNA-depleted sample contains undetectable levels of rRNA molecules that exhibit sequences within the at least one rRNA molecule (e.g., undetectable as measured using agarose gel electrophoresis and ethidium bromide staining). In some embodiments of the method, the composition comprising affinity-tagged antisense rRNA molecules does not exhibit any rRNA internal transcribed spacer sequences. In some other embodiments of the method, the composition comprising the antisense rRNA molecules exhibits internal transcribed spacer sequences selected from among: i) a sequence exhibited by the ITS1 rRNA spacer region, which is located between a eukaryotic 18S rRNA gene and a eukaryotic 5.8S rRNA gene; ii) a sequence exhibited by the ITS2 rRNA spacer region, which is located between a eukaryotic 5.8S rRNA gene and a eukaryotic 28S rRNA gene; iii) a sequence exhibited by a prokaryotic 16S-23S ITS; and iv) a sequence exhibited by a prokaryotic 23S-5S rRNA ITS. In particular embodiments of the methods for generating rRNA-depleted samples or for isolating rRNA from a sample, step b) is performed using a composition comprising antisense rRNA molecules that do not exhibit any rRNA internal transcribed spacer sequences, whereas, in other embodiments, step b) is performed using a composition comprising affinity-tagged antisense rRNA molecules that exhibit one or more of the internal transcribed spacer sequences.

In some embodiments of any of the methods for generating a rRNA-depleted sample from an initial sample wherein the initial sample comprises RNA molecules that comprise rRNA molecules and at least one non-rRNA RNA molecule of interest, the RNA molecules in the initial sample are fragmented (e.g., from an FFPE or other sample comprising degraded RNA molecules, or from a sample wherein the RNA molecules are deliberated degraded (e.g. by incubation in the presence of heat and Mg2+) prior to being provided in the initial sample). In some embodiments of any of the methods of the invention for generating a rRNA-depleted sample, the at least one non-rRNA RNA molecule of interest comprises a multiplicity of non-rRNA molecules of interest. In some embodiments, the at least one non-rRNA RNA molecule of interest comprises substantially all of the non-rRNA RNA molecules present in the initial sample (e.g., including both the intact and fragmented non-rRNA RNA molecules present in the initial sample). In some embodiments, the at least one non-rRNA RNA molecule of interest comprises substantially all of the eukaryotic mRNA molecules present in the initial sample. In some embodiments, the at least one non-rRNA RNA molecule of interest comprises substantially all of the non-rRNA RNA molecules comprising the transcriptome (minus the at least one rRNA molecule) from one or multiple eukaryotic cells, tissues, organs, or organisms (e.g., for use in making sequencing templates or labeled target nucleic acid, e.g., for analysis of the expression or relative expression of said at least one non-rRNA RNA molecule of interest by digital expression analysis or microarray analysis, respectively). In some embodiments, the at least one non-rRNA RNA molecule of interest comprises the non-rRNA RNA molecules comprising a transcriptome (minus the at least one rRNA molecule) of one or multiple eukaryotic cells, tissues, organs, or organisms (e.g., for use in making sequencing templates or labeled target nucleic acid, e.g., for analysis of the expression or relative expression of all of said non-rRNA RNA molecules by digital expression analysis or microarray analysis, respectively, e.g., for medical or agricultural analysis). In some embodiments, the at least one non-rRNA RNA molecule of interest comprises a subfraction of the non-rRNA RNA molecules comprising the transcriptome (minus the at least one rRNA molecules) of one or multiple cells, tissues, organs, or organisms (e.g., a subfraction selected from among mRNA molecules, miRNA molecules, ncRNA molecules, piwiRNA, snRNA, etc.) (e.g., for use in making sequencing templates or labeled target nucleic acid, e.g., for analysis of the expression or relative expression of said subfraction of non-rRNA RNA molecules, e.g., by digital expression analysis or microarray analysis, respectively, e.g., for medical or agricultural analysis). In some embodiments, the at least one non-rRNA RNA molecule of interest comprises substantially all of the non-rRNA RNA molecules comprising a transcriptome (minus the at least one rRNA molecule) of one or multiple prokaryotic cells or of one or multiple cells comprising both eukaryotic and prokaryotic cells. In some embodiments, the at least one non-rRNA RNA molecule of interest comprises or consists of one or multiple RNA molecules that exhibit specific nucleic acid sequences (e.g., wherein the presence or absence or the quantity of said one or multiple RNA molecules that exhibit the specific nucleic acid sequences is used to detect a pathogen or a medical condition, e.g., for screening (e.g., for screening for the presence of a pathogen in water, on a surface, such as a hospital surface, etc.), or e.g., for diagnostic or theranostic assay (e.g., for diagnosing or monitoring the quantity of a pathogen, or the status of a disease or medical condition for deciding on a therapy or treatment).

In some embodiments of any of the methods of the invention for generating a rRNA-depleted sample, the method further comprises using the rRNA-depleted sample or the at least one non-rRNA RNA molecule of interest contained therein for further analysis or use. In some embodiments, the method further comprises using the at least one non-rRNA RNA molecule of interest as part of a method for generating templates for next-generation DNA sequencing (e.g., for digital expression analysis or RNA-Seq, miRNA profiling, etc.). In some embodiments of the method for generating a rRNA-depleted sample, the method further comprises using the at least one non-rRNA RNA molecule of interest as part of a method for generating labeled target nucleic acid molecules for hybridization to probes of an array or microarray on a porous or non-porous surface (e.g., to probes on an array or microarray, a dot blot, etc.). In some embodiments of the method for generating a rRNA-depleted sample, the method further comprises using the rRNA-depleted sample for performing a diagnostic or theranostic assay to detect for the presence of the at least one non-rRNA RNA molecule of interest (e.g., wherein the presence or quantity of said at least one non-rRNA RNA molecule of interest is indicative of the presence or status of a health or disease state). In some embodiments of the method for generating a rRNA-depleted sample, the method further comprises amplifying the at least one non-rRNA RNA molecule of interest for further analysis or use. In some embodiments of the method for generating a rRNA-depleted sample, the method further comprises using the at least one non-rRNA RNA molecule of interest or an amplification product thereof for transfection of a eukaryotic cell (e.g., an antigen-presenting cell (APC), such as a dendritic cell, a macrophage, or an artificial APC for immunotherapeutic use). In some embodiments, the at least one non-rRNA RNA molecule of interest or an amplification product thereof is used for transfection of a human or animal cell from the same individual from whom the at least one non-rRNA RNA molecule of interest was obtained (e.g., to make a vaccine comprising the APC-transfected cell for immunotherapeutic use to treat a disease, e.g., cancer, in a human or animal individual). In some embodiments, the at least one non-rRNA RNA molecule of interest or an amplification product thereof is used for transfection of a cell from a different human or animal than the cell from whom the at least one non-rRNA RNA molecule of interest was obtained (e.g., to make a vaccine comprising the APC-transfected cell for immunotherapeutic use to treat a disease, e.g., cancer, in a human or animal individual). In certain embodiments, the RNA vaccine is made using the at least one non-rRNA RNA of interest from a first individual and the RNA vaccine is used to vaccinate a second individual. In some embodiments of the method for generating a rRNA-depleted sample, the method further comprises using the at least one non-rRNA RNA molecule of interest or an amplification product thereof to manufacture an RNA vaccine for therapeutic use. In some embodiments of the method, the at least one non-rRNA RNA molecule of interest or a sense RNA amplification product thereof is used to manufacture an RNA vaccine that is used to directly inoculate a patient for therapeutic use. In some embodiments, the RNA vaccine is made using the at least one non-rRNA RNA of interest from a cell, tissue, or organ from first individual and is the RNA vaccine is administered to said first individual as an immunotherapeutic treatment. In some embodiments, the RNA vaccine is made using the at least one non-rRNA RNA of interest from a first individual and the RNA vaccine is used to vaccinate a second individual.

In still other embodiments, the invention provides methods for using the composition comprising affinity-tagged antisense rRNA molecules for isolating substantially all of the RNA molecules that, either alone or in combination, exhibit a sequence within at least one full-length rRNA molecule selected from among 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules.

Thus, in some embodiments, the present invention provides methods for isolating substantially all of the RNA molecules that, either alone or in combination, exhibit the sequence within at least one full-length rRNA molecule, the method comprising: a) providing i) an initial sample comprising RNA molecules, wherein the RNA molecules comprise rRNA molecules and non-rRNA RNA molecules; ii) a composition comprising affinity-tagged antisense rRNA molecules that exhibits sequences corresponding to substantially all of at least one full-length rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules; and iii) a binding matrix (e.g., microparticles) comprising affinity-tag-binding molecules; b) contacting the initial sample with the composition under conditions such that at least some of the affinity-tagged antisense rRNA molecules and at least some of the rRNA molecules form double-stranded rRNA hybrids thereby generating a treated sample; c) contacting the treated sample with the binding matrix under conditions such that at least a portion of the double-stranded rRNA hybrids bind to the binding matrix; d) removing the binding matrix to which are bound the double-stranded rRNA hybrids comprising the affinity-tagged antisense rRNA molecules and the at least some of the rRNA molecules from the treated sample; and e) incubating the binding matrix in a solution under conditions wherein the at least some rRNA molecules from the treated sample are released into the solution, thereby isolating substantially all of the RNA molecules that, either alone or in combination, exhibit a sequence within at least one full-length rRNA molecule present in the initial sample (e.g., at least >95% . . . , >98% . . . , >99% . . . , >99.8% . . . , or >99.9% of the at least one full-length rRNA molecules present in the initial sample).

In some embodiments, the present invention provides methods for isolating substantially all of the RNA molecules that, either alone or in combination, exhibit the sequence within at least one full-length rRNA molecule, the method comprising: a) providing i) an initial sample comprising RNA molecules, wherein the RNA molecules comprise rRNA molecules and non-rRNA RNA molecules; ii) a composition comprising affinity-tagged antisense rRNA molecules that exhibits sequences corresponding to substantially all of at least one full-length rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules; and iii) a binding matrix (e.g., microparticles) comprising affinity-tag-binding molecules; b) contacting the initial sample with the composition under conditions such that at least some of the affinity-tagged antisense rRNA molecules and at least some of the rRNA molecules form double-stranded rRNA hybrids thereby generating a treated sample; c) contacting the treated sample with the binding matrix under conditions such that at least a portion of the double-stranded rRNA hybrids bind to the binding matrix; d) removing the binding matrix to which are bound the double-stranded rRNA hybrids comprising the affinity-tagged antisense rRNA molecules and the at least some of the rRNA molecules from the treated sample; and e) incubating the binding matrix in a solution under conditions wherein the at least some rRNA molecules from the treated sample are released into the solution, thereby generating an isolated rRNA sample comprising substantially all of the RNA molecules that, either alone or in combination, exhibit a sequence within at least one full-length rRNA molecule present in the initial sample (e.g., at least >90% . . . , >95% . . . , >98% . . . , >99% . . . , >99.8% . . . , or >99.9% of the at least one full-length rRNA molecule present in the initial sample) and wherein the isolated rRNA sample is substantially free (e.g., at least >90% . . . , >95% . . . , >98% . . . , >99% . . . , >99.8% . . . , or >99.9% free) of the non-rRNA RNA molecules present in the initial sample.

In some embodiments, the present invention provides methods for isolating substantially all of the RNA molecules that, either alone or in combination, exhibit the sequence within at least one full-length rRNA molecule, the method comprising: a) providing i) an initial sample comprising RNA molecules, wherein the RNA molecules comprise rRNA molecules and non-rRNA RNA molecules; ii) a composition comprising affinity-tagged antisense rRNA molecules that exhibits sequences corresponding to substantially all of at least one full-length rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules; and iii) a binding matrix (e.g., microparticles) comprising affinity-tag-binding molecules; b) contacting the initial sample with the composition under conditions such that at least some of the affinity-tagged antisense rRNA molecules and at least some of the rRNA molecules form double-stranded rRNA hybrids thereby generating a treated sample; c) contacting the treated sample with the binding matrix under conditions such that at least a portion of the double-stranded rRNA hybrids bind to the binding matrix; d) removing the binding matrix to which are bound the double-stranded rRNA hybrids comprising the affinity-tagged antisense rRNA molecules and the at least some of the rRNA molecules from the treated sample; and e) incubating the binding matrix in a solution under conditions wherein the at least some rRNA molecules from the treated sample are released into the solution, thereby generating an isolated rRNA sample comprising substantially all of the RNA molecules that, either alone or in combination, exhibit a sequence within at least one full-length rRNA molecule present in the initial sample (e.g., at least >90% . . . , >95% . . . , >98% . . . , >99% . . . , >99.8% . . . , or >99.9% of the at least one full-length rRNA molecule present in the initial sample) and wherein, either i) the isolated rRNA sample is substantially free (e.g., at least >90% . . . , >95% . . . , >98% . . . , >99% . . . , >99.8% . . . , or >99.9% free) of the non-rRNA RNA molecules present in the initial sample, or ii) contains undetectable levels of non-rRNA RNA from the initial sample as measured using agarose gel electrophoresis and ethidium bromide staining.

In some embodiments of the methods for isolating substantially all of the RNA molecules that, either alone or in combination, exhibit the sequence within at least one full-length rRNA molecule, the isolated rRNA sample is from an initial sample (e.g., comprising a biological specimen, including a medical specimen, such as saliva, sputum, feces, urine, or a cell, tissue, or organ sample, an environmental sample, a metagenomic sample, or any other type of sample which may contain the RNA of interest), whether the sample is unprepared or prepared (e.g., by fixation using a solution, e.g., formalin or ethanol; mounting on a slide; or using other procedures known in the art), and the isolated rRNA is analyzed to determine the genera, species or strains of origin, thereby indicating what particular genera, species or strains were present in the initial sample, and therefore, in the particular specimen or environment from which the sample was collected. For example, in some embodiments, the method is used to identify and study the organisms present in a human or animal or plant "microbiome", e.g., for research, medical, or agricultural applications. In some embodiments, the isolate rRNA sample is from an initial sample comprising a sample from a human, animal, or plant specimen that is provided for medical diagnostic or theranostic testing or analysis (e.g., to detect a pathogenic microorganism, such as a fungal or bacterial pathogen, that is or may be related to or causative of a disease condition, e.g., a pathogenic bacterium that can be detected or diagnosed based on analysis of at least one rRNA molecule, e.g., as described by Chakravorty, S et al., J. Microbiol. Methods 69: 330-339, 2007 and by Millar, B C et al. in Current Issues Mol. Biol. 9: 21-40, 2007, both incorporated herein by reference.) In some embodiments, the isolated rRNA sample is analyzed using any of the many next-generation sequencing methods known in the art (e.g., after tagging the 3' end or the 3' and 5' ends of the isolated rRNA molecules and reverse transcribing them to make tagged or di-tagged linear ssDNA templates or circular ssDNA templates for next-generation sequencing (e.g., using a Roche454™, Illumina Solexa™, Life Technologies SOLID™ Pacific Biosciences, Intelligent Biosystems, Helicos, Qiagen, or another next-generation sequencing platform. In still other embodiments, the isolated rRNA sample is analyzed by real-time PCR.

In some embodiments, the present invention provides methods for isolating substantially all of the RNA molecules that, either alone or in combination, exhibit the sequence within at least one full-length rRNA molecule, the method comprising: a) providing i) an initial sample comprising RNA molecules, wherein the RNA molecules comprise rRNA molecules and non-rRNA RNA molecules; and ii) a composition comprising affinity-tagged antisense rRNA molecules that are bound to a binding matrix (e.g., microparticles comprising affinity-tag-binding molecules), wherein the affinity-tagged antisense rRNA molecules, alone or in combination, exhibit sequences corresponding to substantially all of at least one full-length rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules; b) contacting the initial sample with the composition under conditions such that at least some of the affinity-tagged antisense rRNA molecules in the composition and at least some of the rRNA molecules form double-stranded rRNA hybrids that are bound to the binding matrix, thereby generating a treated sample; and c) removing the binding matrix to which the double-strand rRNA hybrids are bound, thereby isolating substantially all of the RNA molecules that, either alone or in combination, exhibit the sequence within at least one full-length rRNA molecule. In some embodiments of this method, the method further comprises the step of washing the binding matrix to which the double-stranded rRNA hybrids are bound in order to remove non-specifically-bound non-rRNA RNA molecules from the sample. In some embodiments, the treated sample is stored on the binding matrix for future analysis or use. In some embodiments, the method further comprises the step of incubating the binding matrix in a solution under conditions wherein the at least some rRNA molecules from the treated sample are released into the solution, thereby generating a solution of the isolated rRNA sample comprising substantially all of the RNA molecules that, either alone or in combination, exhibit a sequence within at least one full-length rRNA molecule present in the initial sample (e.g., at least >90% . . . , >95% . . . , >98% . . . , >99% . . . , >99.8% . . . , or >99.9% of the RNA molecules that, either alone or in combination, exhibit a sequence within at least one full-length rRNA molecule present in the initial sample) and wherein, either i) the isolated rRNA sample is substantially free (e.g., at least >90% . . . , >95% . . . , >98% . . . , >99% . . . , >99.8% . . . , or >99.9% free) of the non-rRNA RNA molecules present in the initial sample, or ii) contains undetectable levels of non-rRNA RNA from the initial sample as measured using agarose gel electrophoresis and ethidium bromide staining. In some embodiments, the isolated rRNA sample is from an environmental or metagenomic sample and the isolated rRNA is analyzed to determine the genera, species or strains that were present in the sample, and therefore, the particular environment from which the sample was collected. In some embodiments, the isolated rRNA sample is analyzed (e.g., by next-generation sequencing, real-time reverse transcription PCR, or another method, such as a method described elsewhere herein).

In some embodiments of any of the methods of the invention for generating a rRNA-depleted sample or for isolating substantially all of the RNA molecules that, either alone or in combination, exhibit the sequence of at least one full-length rRNA molecule, the method uses any of the compositions comprising affinity-tagged antisense rRNA molecules obtained using any of the methods described herein for generating affinity-tagged antisense rRNA molecules.

In some embodiments of any of the methods for generating a rRNA-depleted sample or for isolating substantially all of the rRNA that, either alone or in combination, exhibits a sequence within at least one full-length rRNA molecule from an initial sample, the composition comprising affinity-tagged antisense rRNA molecules that are bound to a binding matrix comprises biotin as the affinity tag, wherein the biotin is joined to at least about two to eight nucleobases per hundred nucleobases of the antisense rRNA molecules, and the binding matrix comprises microparticles to which streptavidin or avidin is attached as the affinity-tag-binding molecule. In some other embodiments of this method, the affinity-tagged antisense rRNA molecules comprise biotin as the affinity tag, wherein the biotin is joined to at least about two to four nucleobases per hundred nucleobases of the antisense rRNA molecules, or to at least about three to five nucleobases per hundred nucleobases of the antisense rRNA molecules, or to at least about four to six nucleobases per hundred nucleobases of the antisense rRNA molecules, or to at least about six to eight nucleobases per hundred nucleobases of the antisense rRNA molecules.

In some embodiments of any of the methods of the invention for generating a rRNA-depleted sample or for isolating substantially all of the rRNA that, either alone or in combination, exhibits a sequence within at least one full-length rRNA molecule from an initial sample, the initial sample contains degraded RNA and the method is used for generating a rRNA-depleted sample for further analysis and use. For example, in some embodiments, the initial sample is an FFPE sample that contains degraded RNA, and the method is used for generating a rRNA-depleted sample that contains at least one non-rRNA RNA molecule of interest, wherein the rRNA-depleted sample is used for analysis of expression or relative expression of one or more RNA molecules, selected from among mRNA, miRNA, ncRNA, piwiRNA, and RNA comprising the whole transcriptome (minus the rRNA) from one or multiple cells, tissues, organs, or organisms, wherein the method of analysis is selected from among microarray analysis (e.g., Affymetrix, NimbleGen Systems, Agilent Systems), next-generation sequencing (or so-called "digital" analysis), including, among others, next-gen RNA sequencing methods and techniques referred to by terms such as "RNA-Seq," "digital mRNA profiling," "transcriptome profiling," and "ribosome profiling" (e.g., Ingolia et al., Science 324: 218-223, 2009), screening analysis, and analysis using a diagnostic or theranostic assay, including a diagnostic or theranostic assay comprising reverse-transcription qPCR, and a diagnostic or theranostic assay comprising RNA amplification and/or detection of a sequencing using a labeled probe.

In certain embodiments of any of the methods of the invention for using a composition comprising affinity-tagged antisense rRNA molecules for generating a rRNA-depleted sample or for isolating substantially all of the RNA molecules that, either alone or in combination, exhibit the sequence of at least one full-length rRNA molecule, the composition of affinity-tagged antisense rRNA molecules are generated from a first species or organism, and used for generating a rRNA-depleted sample or for isolating substantially all of the RNA molecules that, either alone or in combination, exhibit a sequence within at least one full-length rRNA molecule from a second species or organism different from the first species or organism (e.g., the first species or organism is mouse or rat and the second species or organism is human). In some embodiments, the affinity-tagged antisense rRNA molecules are generated from any at least one rRNA molecule from the first species of organism wherein said affinity-tagged antisense rRNA molecules hybridize with sequences exhibited within all of the at least one rRNA molecules present in the initial sample from the second species or organism under the conditions used in the method for generating a rRNA-depleted sample or for isolating at least one rRNA molecule from the initial sample. In further embodiments, the first species or organism is a non-human mammal (e.g., cat, dog, sheep, mouse, rat, monkey, etc.) and the second species or organism is *Homo sapiens*. In particular embodiments, the first species or organism comprises non-*E. coli* bacteria, and the second species or organism is *E. coli*. In some embodiments, the method for generating a rRNA-depleted sample or for isolating substantially all of the RNA molecules that, either alone or in combination, exhibit a sequence within at least one full-length rRNA molecule is performed using a metagenomic or environmental sample containing multiple species or organisms. Thus, in some embodiments wherein the composition comprising affinity-tagged antisense rRNA molecules corresponds to at least one full-length prokaryotic rRNA molecule (e.g., generated from at least one full-length rRNA molecule from *E. coli*), the composition is used for generating a rRNA-depleted sample or for isolating substantially all of the RNA molecules that, either alone or in combination, exhibit a sequence within at least one full-length rRNA molecule comprising multiple rRNA molecules from multiple species or organisms.

In some embodiments of any of the methods of the invention for generating a rRNA-depleted sample or for isolating substantially all of the RNA molecules that, either alone or in combination, exhibit the sequence of at least one full-length rRNA molecule, instead of using the compositions comprising affinity-tagged antisense rRNA molecules, the method uses compositions comprising affinity-tagged single-stranded DNA molecules that, alone or in combination, are complementary to substantially all of the sequence exhibited by the at least one full-length rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules, wherein the affinity tags are present at a ratio of at least about two to at least four affinity tags per hundred nucleobases of the affinity-tagged single-stranded DNA molecules.

Word conducted during developments of the present invention found that the method can be performed using samples wherein the initial sample comprises generally any amount of total RNA molecules. In one embodiment, the amount of total RNA present in the initial sample is between about 10 picograms and 50 nanograms. In another embodiment, the amount of total RNA present in the initial sample is between about 50 nanograms and one microgram. In still another embodiment, the amount of total RNA present in the initial sample is between about one microgram and five micrograms. In some embodiments of these methods, at least a portion of the RNA molecules in the initial sample are highly fragmented (e.g., previously digested with an RNase enzyme or from older RNA samples). In some embodiments of these methods, the RNA molecules in the initial sample are from a paraffin-embedded sample (e.g., paraffin-embedded formalin-fixed sample). In further embodiments of these methods, the affinity-tagged antisense RNA molecules corresponds to the at least one rRNA molecules from the same species or organism (e.g., the affinity-tagged antisense RNA molecules correspond to the at least one rRNA molecule from human cells or the affinity-tagged antisense RNA molecules correspond to the at least one rRNA molecule from *E. coli* cells). In certain embodiments of these methods wherein the affinity-tagged antisense RNA molecules corresponds to the at least one rRNA molecule from human cells, the at least one rRNA molecule is human 28S rRNA.

In some embodiments of any of the methods of the invention for generating a rRNA-depleted sample or for isolating substantially all of the RNA molecules that, either alone or in combination, exhibit the sequence of at least one full-length rRNA molecule, the ratio of the affinity-tag-binding molecules to the affinity tags during the contacting in step b) is at least 2 to 1 (e.g., 2:1, 3:1, 4:1, 5:1, ... or 10:1).

In certain embodiments of any of the methods of the invention for generating a rRNA-depleted sample or for isolating substantially all of the RNA molecules that, either alone or in combination, exhibit the sequence of at least one full-length rRNA molecule, the initial sample comprising RNA molecules represents total RNA isolated from a cell or tissue sample or from an environmental sample (e.g., from a cell line, a tissue biopsy sample, a bodily fluid sample, a swab from a hospital surface, a water sample, etc.). In some embodiments of these methods, the method further comprises providing a control sample of RNA (e.g., comprising total RNA) from a cell or tissue sample, and also performing the method using the control sample. In certain embodiments, the control sample comprises total RNA from HeLa cells and/or from *E. coli* cells.

In additional embodiments of any of the methods of the invention for generating a rRNA-depleted sample or for isolating substantially all of the RNA molecules that, either alone or in combination, exhibit the sequence of at least one full-length rRNA molecule, the initial sample is substantially free of salts and/or organic liquids. In other of these embodiments, the initial sample comprises RNase-free water and/or TE buffer. In particular embodiments, the method further comprises treating the rRNA-depleted sample or the isolated rRNA sample under conditions such that the RNA molecules present in the sample are further purified (e.g., by further purification using ethanol, isopropanol or ammonium acetate precipitation). In particular embodiments, the rRNA-depleted sample or the isolated rRNA sample is used in methods for further analysis, such as for analysis by next-gen sequencing, for preparing labeled target for microarray analysis, for screening or diagnostic or theranostic analysis (e.g., using a plant, human, or animal, screening, diagnostic or theranostic kit). In some embodiments, the nucleic acids in the rRNA-depleted sample or the isolate rRNA sample is amplified prior to further analysis. In other embodiments of these methods, the contacting in step b) is conducted in the presence of an RNase inhibitor. In some embodiments, the compositions used in the method further comprise RNase free water.

In further embodiments of any of the methods of the invention for generating a rRNA-depleted sample or for isolating substantially all of the RNA molecules that, either alone or in combination, exhibit the sequence of at least one full-length rRNA molecule, the condition in step b) comprise incubating at a temperate of about 60-75° C. for a first time period (e.g., 5-15 minutes) and incubating at about room temperature for a second time period (e.g., 10-25 minutes). In some embodiments of these methods, the conditions in step b) include the presence of hybridization buffer. In particular embodiments of these methods, the conditions in step c) include at least occasional mixing at room temperature and/or at 35-60° C. or 25-70° C., or at about 50° C. In further embodiments of these methods, the binding matrix comprises a plurality of individual particles (e.g., nanoparticle, magnetic particles, macroporous beads, etc.) In further embodiments of these methods, the binding matrix comprises a binding column or a membrane. In some embodiments of these methods, the affinity tags are selected from biotin, avidin or streptavidin, digoxigenin, antibodies (or antibody fragments), and other useful binding molecules. In certain embodiments of these methods, the affinity-tag-binding molecules are selected from biotin, avidin or streptavidin, digoxigenin, antibodies (or antibody fragments), and other useful binding molecules.

In some embodiments of the invention, one or more of the sequences in the at least one rRNA molecules, or in one or more of the non-rRNA RNA molecules, or in one or more other nucleic acid molecules present in the initial sample is amplified (e.g., using any appropriate method known in the art for RNA and/or DNA amplification, e.g., real-time PCR or reverse transcription-PCR, transcription-mediated amplification, RNA amplification using a RiboMultiplier™ Kit, Epicentre Biotechnologies, Madison, Wis., strand-displacement amplification, LAMP, ICAN™, UCAN™ (TAKARA), rolling circle amplification, etc.) either, prior to, or after generating the rRNA-depleted sample or isolating the at least one rRNA molecule, respectively, using one of the methods of the present invention for generating a rRNA-depleted sample or for isolating substantially all of the RNA molecules that, either alone or in combination, exhibit the sequence within at least one full-length rRNA molecule. In some of these embodiments, the sample comprising the respective one or more amplified sequences of non-rRNA RNA molecules, or rRNA molecules, and/or other nucleic acid molecules is used for further analysis.

In other embodiments, the present invention provides a composition comprising antisense rRNA molecules corresponding to substantially all of at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules, wherein the antisense rRNA molecules comprise affinity-tags, wherein the composition is substantially free of non-rRNA RNA molecules comprising the affinity tags. In certain embodiments, the composition further comprises a binding matrix, wherein the binding matrix comprises affinity-tag-binding molecules (e.g., microparticles). In particular embodiments, the antisense rRNA molecules are bound to the binding matrix via the affinity-tag-affinity tag binding molecule interaction.

In some embodiments, the present invention provides compositions comprising: a) a composition comprising antisense rRNA molecules corresponding to substantially all of at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules, wherein the antisense rRNA molecules comprise affinity tags, and b) non-rRNA RNA molecules that are affinity-tag free. In certain embodiments, the compositions further comprise a binding matrix comprising affinity-tag-binding molecules.

In particular embodiments, the present invention provides compositions comprising an rRNA-depleted sample comprising non-rRNA RNA molecules, wherein the composition is substantially free of rRNA sequences exhibited by at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules.

In further embodiments, the present invention provides compositions comprising antisense rRNA molecules corresponding to substantially all of at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules, wherein the antisense rRNA molecules comprise affinity-tags, and wherein the composition is substantially free of non-rRNA RNA molecules comprising the affinity tags.

In other embodiments, the present invention provides compositions comprising: a) compositions comprising antisense rRNA molecules corresponding to substantially all of at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules, wherein the antisense rRNA molecules comprise affinity-tags, and b) non-rRNA RNA molecules that are affinity-tag free. In further embodiments, the compositions further comprise a binding matrix comprising affinity-tag-binding molecules.

In some embodiments, the present invention provides compositions comprising: an rRNA-depleted sample comprising non-rRNA RNA molecules, wherein the composition is substantially free of rRNA sequences exhibited by at least one rRNA molecule selected from among 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules. In some particular embodiments, the compositions are substantially free of rRNA sequences exhibited by two, three, or four rRNA molecules selected from among 25S, 26S, 28S, 18S, 5.8S, and 5S eukaryotic cytoplasmic rRNA molecules. In some particular embodiments, the compositions are substantially free of rRNA sequences exhibited by both 12S and 16S eukaryotic mitochondrial rRNA molecules.

In certain embodiments, the present invention provides compositions comprising: a) compositions comprising antisense rRNA molecules corresponding to substantially all of at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules, wherein the antisense rRNA molecules comprise affinity-tags, and wherein the antisense rRNA molecules are from a first species or organism, and b) non-rRNA RNA molecules that are affinity-tag free, wherein the non-rRNA RNA molecules are from a second species or organism different from the first species or organism. In other embodiments, the compositions further comprise a binding matrix comprising affinity-tag-binding molecules.

In some embodiments, the present invention provides compositions comprising: a) affinity-tagged antisense rRNA molecules corresponding to substantially all of at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules, wherein the affinity tags are present on the antisense rRNA molecules at a ratio of at least about two to eight affinity tags per hundred nucleobases of the antisense rRNA molecules, and b) non-rRNA RNA molecules that are affinity-tag free. In some embodiments, composition comprises affinity-tagged antisense rRNA molecules from a first species or organism and non-rRNA RNA molecules that are affinity-tag free from a second species or organism. In certain embodiments, the compositions further comprise a binding matrix comprising affinity-tag-binding molecules.

In additional embodiments, the present invention provides compositions comprising: an rRNA-depleted sample comprising non-rRNA RNA molecules, wherein the composition is at least about 99.0% free of rRNA sequences exhibited by at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules.

The present invention provides kits or systems for performing any of the methods of the invention, including any of the steps of said methods.

For example, in some further embodiments, the present invention provides kits and systems comprising: a) a first component comprising a composition comprising antisense rRNA molecules complementary to substantially all of the sequence exhibited by the at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules, wherein the antisense rRNA molecules comprise affinity-tags, and wherein the composition is substantially free of non-rRNA RNA molecules comprising the affinity tags; and b) at least one second component selected from the group consisting of: i) a binding matrix comprising affinity-tag-binding molecules; ii) a control sample comprising total RNA from a cell or tissue sample; iii) a solution comprising an RNase inhibitor; iv) a binding matrix wash solution that is RNase-free; v) a volume of RNase-free water; vi) a hybridization buffer; vii) a total RNA purification reagent; and viii) a binding matrix resuspension solution, wherein said solution is RNase-free. In certain embodiments, the second component is the binding matrix. In further embodiments, the second component is the control sample. In some embodiments, the second component is the solution comprising an RNase inhibitor.

In some embodiments, the present invention provides kits and systems comprising: a) a first component comprising a composition comprising antisense rRNA molecules complementary to substantially all of the sequence exhibited by the at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules, wherein the antisense rRNA molecules comprise affinity-tags, and wherein the composition is substantially free of non-rRNA RNA molecules comprising the affinity tags; and b) at least one second component selected from the group consisting of: i) a binding matrix comprising affinity-tag-binding molecules; ii) a control sample comprising total RNA from a cell or tissue sample; iii) a solution comprising an RNase inhibitor; iv) a binding matrix wash solution that is RNase-free; v) a volume of RNase-free water; vi) a hybridization buffer; and vii) a total RNA purification reagent.

In additional embodiments, the present invention provides kits and systems comprising: a) a first component comprising a composition comprising affinity-tagged antisense rRNA molecules complementary to substantially all of the sequence exhibited by the at least one rRNA molecule selected from: 25S, 26S, 28S, 18S, 5.8S, and 5S eukaryotic cytoplasmic rRNA molecules, 12S and 16S eukaryotic mitochondrial rRNA molecules, and 23S, 16S, and 5S prokaryotic rRNA molecules, wherein the antisense rRNA molecules comprise affinity tags, wherein the affinity tags are present on the antisense rRNA molecules at a ratio of at least about two to eight affinity tags per hundred nucleobases of the antisense rRNA molecules, and wherein the composition is substantially free of non-rRNA RNA molecules comprising the affinity tags; and b) at least one second component selected from the group consisting of: i) a binding matrix comprising affinity-tag-binding molecules; ii) a control sample comprising total RNA from a cell or tissue sample; iii) a solution comprising an RNase inhibitor; iv) a binding matrix wash solution that is RNase-free; v) a volume of RNase-free water; vi) a hybridization buffer; and vii) a total RNA purification reagent.

In some embodiments of a kit or system, the affinity-tags are present in the composition of affinity-tagged antisense rRNA molecules at a ratio of at least about two to about eight affinity tags per every 100 nucleobases of the antisense rRNA molecules (e.g., at least 2:100, 3:100, 4:100, 5:100, 6:100, 7:100, or 8:100). In certain embodiments, the affinity tag is associated with only one nucleobase of the antisense rRNA molecules. In some of these embodiments, the affinity-tags are associated with only one type of nucleobase selected from: adenine (A), cytosine (C), guanine (G) and uracil (U).

In other embodiments of a kit or system, the compositions comprising affinity-tagged antisense rRNA molecules correspond to at least 95.0% of all of the at least one rRNA sequence (e.g., 95.0% . . . 95.5% . . . 96.0% . . . 96.5% . . . 97.0% . . . 97.5% . . . 98% . . . 98.5% . . . 99.0% . . . 99.5% . . . 99.9 . . . or 100% of the at least one rRNA molecule (e.g., wherein the compositions comprise antisense rRNA molecules that exhibit, alone or in combination, sequences corresponding to all of the full-length rRNA sequence for a particular rRNA molecule).

BRIEF DESCRIPTION OF THE DRAWINGS

The foregoing summary and description is better understood when read in conjunction with the accompanying drawings which are included by way of example and not by way of limitation.

DEFINITIONS

Figure 1A:
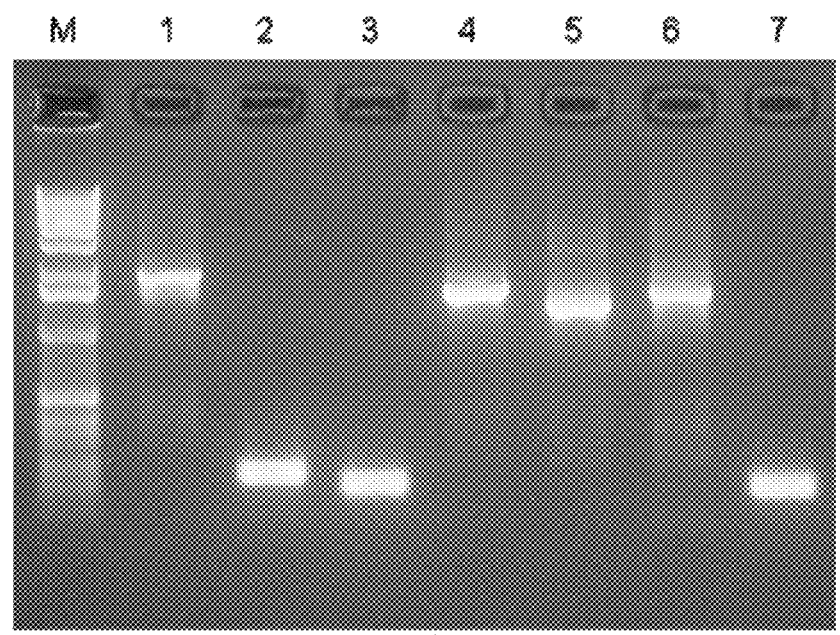
FIG. 1A shows an ethidium bromide stained agarose gel containing the following PCR amplicons: Lane M—DNA molecular weight ladder; Lane 1—300 ng of PCR amplicon for human 18S rRNA; Lane 2—300 ng of PCR amplicon for human 5.8S rRNA; Lane 3—300 ng of PCR amplicon for human 5S rRNA; Lane 4—300 ng of PCR amplicon for *E. coli* 23S rRNA 5' segment; Lane 5—300 ng of PCR amplicon for *E. coli* 23S rRNA 3' segment; Lane 6—300 ng of PCR amplicon for *E. coli* 16S rRNA; and Lane 7—300 ng of PCR amplicon for *E. coli* 5SS rRNA

It is to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology and grammatical variants will be used in accordance with the definitions set forth below.

When the terms "for example", "e.g.", "such as", "include", "including" or variations thereof are used herein, these terms will not be deemed to be terms of limitation, and will be interpreted to mean "but not limited to" or "without limitation."

As used herein, a "composition comprising affinity-tagged antisense rRNA molecules" means "a composition comprising RNA molecules that, either alone or in combination, exhibit one or more sequences that are complementary to substantially all of the sequence exhibited by the at least one full-length rRNA molecule, wherein at least a portion of the nucleotides in said RNA molecules are joined to an affinity tag."

As used herein, the phrase "a composition comprising antisense rRNA molecules corresponding to substantially all of at least one rRNA molecule" or "a composition comprising antisense rRNA molecules corresponding to substantially all of" (or "all of the sequence exhibited by") "at least one rRNA molecule" or "a composition comprising antisense rRNA molecules that, alone or in combination, are complementary to substantially all" (or "all of the sequence") "of at least one full-length rRNA molecule"

refers to a composition comprising affinity-tagged antisense rRNA molecules that exhibit, that will specifically hybridize with or anneal with or complex with, at least 95% of the RNA molecules or fragments of RNA molecules that exhibit a sequence of a particular full-length rRNA molecule. Preferably, the antisense rRNA molecules in the composition will specifically hybridize with at least 95% of the molecules of a particular rRNA molecule or fragments thereof in a sample, such that, when affinity-tagged, said antisense rRNA molecules can be used with a binding matrix to remove at least about 95% of the RNA molecules or fragments of RNA molecules that exhibit a sequence of said particular rRNA molecule from the sample. It is not necessary that the antisense nucleic acid sequences exhibited in the composition share 95% sequence identity with the complement of a particular rRNA molecule, but instead, it is only necessary that the antisense nucleic acid sequences are able to specifically hybridize, anneal or complex with at least 95% of the RNA molecules or fragments of RNA molecules that exhibit a sequence of said particular rRNA molecule. The antisense nucleic acid sequences in the composition do not need to be present in a single nucleic acid strand (although they may be), but instead, the composition comprising antisense rRNA molecule can consist of antisense rRNA fragments that will collectively hybridize with at least 95% of the RNA molecules or fragments of RNA molecules that exhibit a sequence of a particular rRNA molecule. In certain embodiments, the antisense nucleic acid sequences will specifically hybridize with at least 95% . . . 96% . . . 97% . . . 98% . . . 98.5% . . . 99.0% . . . 99.3% . . . 99.5% . . . 99.8%, 99.0% . . . 99.5% . . . 99.9 . . . or 100% of the RNA molecules or fragments of RNA molecules that exhibit the sequence of a particular rRNA molecule.

A used herein, the phrase "an rRNA-depleted sample that comprises substantially all of said at least one non-rRNA RNA molecule of interest present in said initial sample," refers to a purified sample that originally contained rRNA molecules and a first amount of the at least one non-rRNA RNA molecule of interest and that has been purified by removing a certain amount of rRNA molecules, while retaining at least 90% of said first amount of said at least one non-rRNA RNA molecule of interest. In certain embodiments, at least 91% . . . 93% . . . 96% . . . 97% . . . 98% . . . 98.5% . . . 99.0% . . . 99.3% . . . 99.5% . . . 99.8% . . . , or 99.9% of said first amount of said at least one non-rRNA RNA molecule of interest is present in the rRNA-depleted sample. Those with knowledge in the art will know or easily find methods for assaying for the first amount of the at least one non-rRNA RNA molecule of interest in the initial sample and assaying for the amount of the at least one non-rRNA RNA molecule of interest remaining in the rRNA-depleted sample, and using said information to calculate the percentage of said first amount of said at least one non-rRNA RNA molecule of interest that is present in the rRNA-depleted sample. For example, in one embodiment, the percentage of the at least one non-rRNA RNA molecule of interest remaining in the rRNA-depleted sample is determined based on the amounts of the at least one non-rRNA RNA molecule of interest in the initial sample and in the rRNA-depleted sample as determined using reverse transcription real-time PCR (also called "RT-qPCR").

A used herein, the phrase "an isolated rRNA sample that is substantially free of the non-rRNA RNA molecules present in the initial sample" refers to a purified sample that initially contained non-rRNA RNA molecules and a first amount of the at least one rRNA molecule and that has been purified by removing a certain amount of the non-rRNA RNA molecules, while retaining at least 90% of said first amount of said at least one rRNA molecule. In certain embodiments, at least >90% . . . , >95% . . . , >98% . . . , >99% . . . , >99.8% . . . , or >99.9% of said first amount of said at least one rRNA molecule is present in the isolated rRNA sample. In certain embodiments, at least >90% . . . , >95% . . . , >98% . . . , >99% . . . , >99.8% . . . , or >99.9% of the non-rRNA RNA molecules that were present in the initial sample are not present in the isolated rRNA sample (e.g., wherein the amounts of the at least one rRNA molecule and/or of the non-rRNA molecules are determined using RT-qPCR as described above).

As used herein, the phrase "substantially free of RNA molecules that exhibit sequences of the at least one rRNA molecule" refers to a purified sample wherein 5% or less of all the molecules present in the initial sample that exhibited a nucleic acid sequence from said at least one rRNA molecule are still present in the rRNA-depleted sample. In certain embodiments, 5% . . . 4% . . . 3% . . . 2% . . . 1.5% . . . 1.0% . . . 0.5% . . . or 0.1% or less of all the molecules present in the initial sample that exhibited a nucleic acid sequence from a particular rRNA molecule are still present in the purified sample. Those with knowledge in the art will know or easily find methods for assaying for the amounts of RNA molecules that exhibit sequences of the at least one rRNA molecule that are present in the initial sample and in the rRNA-depleted sample. For example, in one embodiment, the percentage of RNA molecules that exhibit sequences of the at least one rRNA molecules is determined based on the amounts of the RNA molecules that exhibit sequences of the at least one rRNA molecule in the initial sample and in the rRNA-depleted sample as determined using reverse transcription real-time PCR (also called "RT-qPCR").

As used herein, the phrase "substantially free of non-rRNA RNA molecules comprising affinity tags," refers to a composition wherein 2% or less of all the affinity-tagged nucleic acid sequences present are non-rRNA RNA molecules having affinity tags. In certain embodiments, 2% . . . 1.5% . . . 1.0% . . . 0.5% . . . 0.1% or less of all the affinity-tagged nucleic acid molecules present are non-rRNA RNA molecules having affinity tags.

As used herein, the terms "an rRNA-depleted sample" or "a sample that is substantially free of rRNA molecules" is sometimes referred to herein as "a rRNA subtracted sample" or "a subtracted sample," and the "methods for generating rRNA-depleted samples" or the "methods for isolating rRNA from samples" are sometimes referred to herein as "methods for rRNA subtraction" or, more simply, as "rRNA subtraction." The term "rRNA subtraction" herein shall mean and refer to "a method for generating a rRNA-depleted sample or a method for isolating rRNA from a sample." Similarly, when a form of the verb "to subtract" is used herein, it shall mean "a method or the process of performing a method for generating a rRNA-depleted samples or for isolating rRNA from a sample" and the term "subtracted" herein shall mean or refer to the rRNA-depleted state of the sample after performing the method or process.

As used herein, the phrase "binding matrix" refers to any type of substrate, whether porous or non-porous, that will bind affinity-tagged nucleic acid molecules such that affinity-tagged nucleic acid molecules, and the sequences they are hybridized to, can can be preferentially removed from a sample. Affinity-tag-binding molecules are associated with the binding matrix to allow the binding matrix to bind affinity-tagged nucleic acid molecules. Examples of such binding matrices include, but are not limited to, nylon membranes or particles, silica membranes or particles, cellulose acetate membranes or particles, membranes or particles composed of silica and $Fe_2O_3$, and other similar membranes, fibers, coated plates, solid supports, and particles.

As used herein, a "specific binding pair" refers to two molecules that have affinity for and "bind" to each other under certain conditions, referred to as "binding conditions." Biotin and streptavidin or avidin are examples of a "specific binding pair" or "affinity binding molecules," but the invention is not limited to use of this particular specific binding pair. In many embodiments of the present invention, one member of a particular specific binding pair is referred to as the "affinity tag molecule" or the "affinity tag" and the other as the "affinity-tag-binding molecule" or the "affinity tag binding molecule." For example, but without limitation, in some embodiments, biotin is referred to as the affinity tag or affinity tag molecule, and a streptavidin or avidin molecule, whether it is free, attached to a surface, attached to another molecule, or labeled with a detectable molecule such as a dye, is referred to as the affinity-tag-binding molecule. In other embodiments, streptavidin is the affinity tag and biotin is the affinity-tag-binding molecule, since streptavidin and biotin function together as a specific binding pair or as affinity binding molecules. A wide variety of other specific binding pairs or affinity binding molecules, including both affinity tag molecules and affinity-tag-binding molecules, are known in the art (e.g., see U.S. Pat. No. 6,562,575, herein incorporated by reference), which can be used in the present invention. For example, an antigen (which itself may be an antibody) and an antibody, including a monoclonal antibody, that binds the antigen is a specific binding pair. Also, an antibody and an antibody binding protein, such as Staphylococcus aureus Protein A, can be employed as a specific binding pair. Other examples of specific binding pairs include, but are not limited to, a carbohydrate moiety which is bound specifically by a lectin and the lectin; a hormone and a receptor for the hormone; and an enzyme and an inhibitor of the enzyme. Usually, molecules that comprise a specific binding pair interact with each other through non-covalent bonds such as hydrogen-bonding, hydrophobic interactions (including stacking of aromatic molecules), van der Waals forces, and salt bridges. Without being bound by theory, it is believed in the art that these kinds of non-covalent bonds result in binding, in part due to complementary shapes or structures of the molecules involved in the binding pair. The term "binding" according to the invention refers to the interaction between an affinity binding molecules or specific binding pairs (e.g., between biotin as an affinity tag molecule and streptavidin as an affinity-tag-binding molecule) as a result of non-covalent bonds, such as, but not limited to, hydrogen bonds, hydrophobic interactions, van der Waals bonds, and ionic bonds. Based on the definition for "binding," and the wide variety of affinity binding molecules or specific binding pairs, it is clear that "binding conditions" vary for different specific binding pairs. Those skilled in the art can easily determine conditions whereby, in a sample, binding occurs between the affinity binding molecules. In particular, those skilled in the art can easily determine conditions whereby binding between affinity binding molecules that would be considered in the art to be "specific binding" can be made to occur. As understood in the art, such specificity is usually due to the higher affinity between the affinity binding molecules than for other substances and components (e.g., vessel walls, solid supports) in a sample. In certain cases, the specificity might also involve, or might be due to, a significantly more rapid association of affinity binding molecules than with other substances and components in a sample.

In some embodiments of the invention, an "affinity tag reagent" or and "affinity tag having a reactive moiety" is used, by which we mean herein, a molecule that comprises both an affinity tag and a reactive chemical group or moiety that is capable of reacting with one or more atoms or groups of the molecule with which it reacts to form one or more covalent chemical bonds between the molecule comprising the affinity tag and the molecule with which it reacts. By way of example, but without limitation, in some embodiments, the affinity tag reagent is an acylating reagent (e.g., an N-hydroxysuccinimidyl ester), wherein the affinity tag is chemically joined to an atom in the molecule with which it reacts via an acyl linkage. In other embodiments, the affinity tag reagent is an alkylating reagent, group, wherein the affinity tag is chemically joined to an atom in the molecule with which it reacts via an alkyl linkage. In other embodiments, the affinity tag reagent reacts via an electrocyclic type of chemical reaction, such as a 1,3-dipolar cycloaddition (e.g., cycloaddition of an alkyne with an azide). Thus, the term "reactive" moiety with respect to, for example, an "affinity tag reagent" or "affinity tag having a reactive moiety" is used to refer to a moiety or group that is involved in or responsible for the chemical reaction whereby a molecule comprising the affinity tag reacts chemically to form a covalent chemical bond with one or more atoms in the molecule with which it reacts, rather than to the binding that results between affinity binding molecules due to non-covalent forces and bonds.

When we refer to attaching the "affinity-tag-binding molecule" or the "affinity tag binding molecule," such as streptavidin or avidin, directly to the surface or solid support, it usually, but not always means that the affinity-tag-binding molecule is covalently attached to the surface by means of a chemical linker that is joined to the surface and to the affinity-tag-binding molecule. When we refer to attaching the "affinity-tag-binding molecule" or the "affinity tag binding molecule," such as streptavidin or avidin, indirectly to the surface, it is meant that the affinity-tag-binding molecule is bound to another molecule with which it has affinity (e.g., an anti-streptavidin antibody) that is in turn bound to the surface. In some embodiments, the affinity-tag-binding molecule, such as streptavidin or avidin, is not attached to a surface, but is bound by another molecule, such as an antibody or Protein A, and the biotinylated modified-nucleotide-capped RNA is recovered by precipitation or by binding to a second antibody or other molecule using methods and compositions known in the art.

As used herein, the term "about" means encompassing plus or minus 25%. For example, "about 200 nucleotides" refers to a range encompassing between 150 and 250 nucleotides.

As used herein, the term "hybridization" or "hybridize" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, the melting temperature ($T_m$) of the formed hybrid, and the G:C ratio within the nucleic acids. A single molecule that contains pairing of complementary nucleic acids within its structure is said to be "self-hybridized." An extensive guide to nucleic hybridization may be found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993), which is incorporated by reference.

DETAILED DESCRIPTION

The present invention provides methods, compositions, and kits for generating rRNA-depleted samples and for isolating rRNA from samples. In particular, the present invention provides compositions comprising affinity-tagged antisense rRNA molecules corresponding to substantially all of the sequence of at least one rRNA molecule (e.g., a eukaryotic 28S, 26S, 25S, 18S, 5.8S, and/or 5S rRNA and/or a prokaryotic 23S, 16S, and/or 5S rRNA) and methods of using such compositions to generate rRNA-depleted samples.

Ribosomal RNA constitutes a majority mass of the RNA content of a cell and thus, presents a tremendous background contamination burden when studying the less abundant and, often, more relevant transcripts. Methods to reduce rRNA are available but are severely limiting since, for example, they require only "high quality intact RNA" samples for good rRNA removal. Fragments of rRNA in the sample without the complementary consensus sequences will not be removed using the methods in the art and, thus, still contribute to significant rRNA contamination of the sample, which limits the efficacy of downstream transcript analysis and significantly increases cost burden from unnecessary use of consumables and manpower. Furthermore, even in the best case wherein the RNA in the sample comprises so-called "intact total RNA," the sample can still comprise a population of fragmented rRNA, which still gives rise to a rRNA background using the methods in the art. Still further, the methods in the art do not remove sufficient quantities of all of the sequence exhibited by the rRNA molecules, so the rRNA background is high when the sample is used for modern analysis methods, such as for generating tagged sequencing templates from RNA for use in next-generation sequencing (e.g., for so-called "digital" gene expression methods). For example, it has been reported that more than half of the sequence reads can be for rRNA sequences, even after one or more rounds of rRNA removal using commercial methods known in the art (e.g., using RiboMinus™, Life Technologies, Carlsbad, Calif.). Another requirement of these existing methods is the need for a relatively large sample size, which is frequently prohibitive. Often, total RNA extracted from especially long-term stored cell/tissue samples is invariably very fragmented and limited in quantity. Thus, a method to simultaneously remove both fragmented and intact rRNA and to do so from a small sample size is needed.

The present invention addresses this need as it provides, for example, methods for the efficient removal of either completely fragmented or variably fragmented rRNA molecules, leaving the non-rRNA RNA transcripts generally unperturbed. Furthermore, the method operates independently of any "unique feature" of the non-ribosomal RNA transcripts such as, a poly(A) tail as in the case of eukaryotic mRNA and thus, presents no selection bias in the recovery of all non-ribosomal RNA transcripts. In certain embodiments to achieve these objectives, one or more affinity-tagged antisense rRNA representing substantially all of the full-length sequence of each rRNA in whole or in part (e.g., eukaryotic 28S, 26S, 25S, 18S, 5.8S and/or 5Ss and/or prokaryotic 23S, 16S and 5S) are synthesized and hybridized to their respective complementary rRNA sequences in the test sample, and the hybrids as well as any residual unhybridized affinity-tagged antisense rRNA molecules are then physically removed using affinity-tag-binding molecules (e.g., linked to a binding matrix), leaving the non-rRNA RNA transcripts unperturbed. Since substantially the entire (or the entire) sequence of at least one, and preferably each rRNA, is represented in the composition comprising affinity-tagged antisense rRNA molecules, any size fragments of the native rRNA contained in the samples are also able to form hybrids under the same hybridization conditions and are efficiently removed along with any intact rRNA sequences that may also be present.

In particular embodiments, in order to achieve efficient rRNA removal, a molar excess of the affinity-tagged antisense rRNA molecules is used in the hybridization reaction, which drives the hybrid formation process to completion. Excess affinity-tagged antisense rRNA molecules may also be removed since these molecules themselves may contribute to various types of background in different downstream methods or analyses. To accomplish this, the affinity-tagged antisense rRNA molecules preferably contain an optimal amount of affinity-tag molecules, and an appropriate amount of the binding matrix comprising the affinity-tag-binding molecules is used for removal of both rRNA-hybridized and unhybridized affinity-tagged antisense rRNA molecules. As described in the Examples, conditions were developed that allow the methods to be performed using samples comprising a broader dynamic range of total RNA than existing methods, including using samples comprising sub-microgram quantities of total RNA.

Exemplary rRNA Sequences and Primers

The present invention includes compositions comprising affinity-tagged antisense rRNA molecules corresponding to substantially all of at least one rRNA molecule. The present invention is not limited to compositions comprising antisense rRNA molecules that exhibit sequences that are exactly complementary to particular rRNA molecules in the sample, but instead includes compositions comprising antisense rRNA molecules that hybridize with or anneal to or complex with any rRNA molecules in the sample, whether or not said rRNA molecules are from the same organism.

Exemplary Embodiment

Described below is an exemplary embodiment that may be used to generate rRNA-depleted samples using affinity-tag-binding molecule linked microspheres (herein after "binding microspheres" or "microspheres"). This embodiment is not meant to limit the present invention and instead is simply an exemplary embodiment.

Wash the binding microspheres and suspend in solution (20 mM Tris-HCl pH 7.5, 1 M NaCl, 1 mM EDTA and 0.0005% RNase-Free Triton-X100). Allow the binding microspheres to reach room temperature. Vigorously vortex the microspheres for 20 seconds to produce a homogeneous suspension. For each reaction, pipette 25 µl of the resuspended microspheres into a microsphere wash tube. Centrifuge the dispensed microspheres at 10,000 rpm in a bench top microcentrifuge for 3 minutes. Carefully pipette off and discard the supernatant, without disturbing the microsphere pellet. Wash the microspheres by adding 1 volume of wash solution (20 mM Tris-HCl pH 7.5, 1 M NaCl and 1 mM EDTA) equal to the original volume of microspheres (e.g., add 25 µl of wash solution for every 25 µl of microspheres) to the tube. Resuspend the microspheres by vigorous vortex mixing. Centrifuge the tube at 10,000 rpm for 3 minutes in a bench top microcentrifuge. Carefully pipette off and discard the supernatant, without disturbing the microsphere pellet. Repeat the wash, resuspension, centrifuge, and pipetting steps.

Resuspend the microspheres in 1 volume resuspension solution. For example, add 25 µl of resuspension solution for every 25 µl of microspheres that were originally used. Resuspend the microspheres by vigorous vortex mixing to produce a homogeneous suspension. Add 0.25 µl of Script-Guard™ RNase Inhibitor (EPICENTRE, Madison, Wis.) to the tube for every 25 µl of resuspended microspheres and store them at room temperature.

For a sample containing, for example, 50 ng-1 ug to total RNA (e.g., human, mouse, or rat), in a 0.2-ml thin-walled microcentrifuge tube, combine: 10× reaction buffer (0.5M Tris-HCl pH7.5 and 1 M NaCl), a total RNA sample, a rRNA removal solution (1.2 pmoles each of affinity-tagged antisense rRNA molecules corresponding to 28S, 18S, 5.8S and 5S human rRNA molecules), and RNase-free water. Gently mix the reaction(s) and incubate at 68° C. for 10 minutes. Remove the reaction tube(s) to room temperature and incubate for at least 15 minutes.

Resuspend the washed microspheres from above by pipetting up and down. For each sample, pipette 25 µl of the microspheres to a new RNase-free 1.5-ml microcentrifuge tube. Add the room temperature total RNA sample to the appropriate tube containing the microspheres. Mix each thoroughly by pipetting the tube contents up and down. Incubate each tube at room temperature for 15 minutes with occasional (every 3-4 minutes) mixing by gentle vortex (low setting) for 5 seconds. Place the tube at 37° C. for 5 minutes. Immediately centrifuge the tube at 14,000 rpm in a microcentrifuge for 5 minutes at room temperature. Carefully pipette off each supernatant, which contains the rRNA-depleted sample, to an RNase-free 1.5-ml microcentrifuge tube. If there are microspheres still visible in the sample, and ethanol precipitation is desired to be used, repeat the above procedure. The rRNA-depleted sample can, for example, be purified by ethanol precipitation or column method.

For ethanol precipitation, adjust the volume of each sample to 180 µl using RNase-free water. Add 18 µl of 3M Sodium Acetate to each tube. Add 2 µl of Glycogen (10 mg/ml) to each tube and mix by gentle vortex. Add 3 volumes (600 µl) of ice cold 100% ethanol to each tube and mix thoroughly by gentle vortex. Place the tubes at −20° C. for at least 1 hour. Centrifuge the tubes at >10,000×g in a microcentrifuge for 30 minutes. Carefully remove and discard the supernatant. Wash the pellet with ice cold 70% ethanol and centrifuge at >10,000×g for 5 minutes. Carefully remove and discard the supernatant. Repeat the ethanol and centrifuge step. Centrifuge briefly to collect any residual supernatant. Carefully remove and discard the supernatant and allow the pellet to air dry at room temperature for 5 minutes. Dissolve the pellet in the desired volume of RNase-free water or buffer.

For column purification, the RNA Clean & Concentrator™-5 Column (Zymo Research; Catalog Numbers R1015, R1016) can be used to used to purify the rRNA-depleted RNA sample. If using the RNA Clean & Concentrator-5 Column, follow the manufacturer's procedure entitled "To recover total RNA including small RNAs". The eluted RNA can be used immediately of stored at −70° C. to −80° C.

Sequencing Technologies

Purified RNA samples generated in accordance with the present invention can be sequenced using any type of suitable sequencing technology. The present invention is not limited by the type of sequencing method employed. Exemplary sequencing methods are described below.

Illustrative non-limiting examples of nucleic acid sequencing techniques include, but are not limited to, chain terminator (Sanger) sequencing and dye terminator sequencing. Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A set of methods referred to as "next-generation sequencing" techniques have emerged as alternatives to Sanger and dye-terminator sequencing methods (Voelkerding et al., *Clinical Chem.*, 55: 641-658, 2009; MacLean et al., *Nature Rev. Microbiol.*, 7: 287-296; each herein incorporated by reference in their entirety). Most current methods describe the use of next-generation sequencing technology for de novo sequencing of whole genomes to determine the primary nucleic acid sequence of an organism. In addition, targeted re-sequencing (deep sequencing) allows for sensitive mutation detection within a population of wild-type sequence. Some examples include recent work describing the identification of HIV drug-resistant variants as well as EGFR mutations for determining response to anti-TK therapeutic drugs. Recent publications describing the use of bar code primer sequences permit the simultaneous sequencing of multiple samples during a typical sequencing run including, for example: Margulies, M. et al. "Genome Sequencing in Microfabricated High-Density Picoliter Reactors", Nature, 437, 376-80 (2005); Mikkelsen, T. et al. "Genome-Wide Maps of Chromatin State in Pluripotent and Lineage-Committed Cells", Nature, 448, 553-60 (2007); McLaughlin, S. et al. "Whole-Genome Resequencing with Short Reads: Accurate Mutation Discovery with Mate Pairs and Quality Values", ASHG Annual Meeting (2007); Shendure J. et al. "Accurate Multiplex Polony Sequencing of an Evolved Bacterial Genome", Science, 309, 1728-32 (2005); Harris, T. et al. "Single-Molecule DNA Sequencing of a Viral Genome", Science, 320, 106-9 (2008); Simen, B. et al. "Prevalence of Low Abundance Drug Resistant Variants by Ultra Deep Sequencing in Chronically HIV-infected Antiretroviral (ARV) Naïve Patients and the Impact on Virologic Outcomes", 16th International HIV Drug Resistance Workshop, Barbados (2007); Thomas, R. et al. "Sensitive Mutation Detection in Heterogeneous Cancer Specimens by Massively Parallel Picoliter Reactor Sequencing", Nature Med., 12, 852-855 (2006); Mitsuya, Y. et al. "Minority Human Immunodeficiency Virus Type 1 Variants in Antiretroviral-Naïve Persons with Reverse Transcriptase Codon 215

Revertant Mutations", J. Vir., 82, 10747-10755 (2008); Binladen, J. et al. "The Use of Coded PCR Primers Enables High-Throughput Sequencing of Multiple Homolog Amplification Products by 454 Parallel Sequencing", PLoS ONE, 2, e197 (2007); and Hoffmann, C. et al. "DNA Bar Coding and Pyrosequencing to Identify Rare HIV Drug Resistance Mutations", Nuc. Acids Res., 35, e91 (2007), all of which are herein incorporated by reference.

Compared to traditional Sanger sequencing, next-gen sequencing technology produces large amounts of sequencing data points. A typical run can easily generate tens to hundreds of megabases per run, with a potential daily output reaching into the gigabase range. This translates to several orders of magnitude greater than a standard 96-well plate, which can generate several hundred data points in a typical multiplex run. Target amplicons that differ by as little as one nucleotide can easily be distinguished, even when multiple targets from related species or organisms are present. This greatly enhances the ability to do accurate genotyping. Next-gen sequence alignment software programs used to produce consensus sequences can easily identify novel point mutations, which could result in new strains with associated drug resistance. The use of primer bar coding also allows multiplexing of different patient samples within a single sequencing run.

Next-generation sequencing (NGS) methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen and Pacific Biosciences, respectively.

In pyrosequencing (Voelkerding et al., *Clinical Chem.*, 55: 641-658, 2009; MacLean et al., *Nature Rev. Microbiol.*, 7:287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $1 \times 10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. No. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color and thus identity of each probe corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing in employed (see, e.g., Astier et al., J Am Chem Soc. 2006 Feb. 8; 128(5):1705-10, herein incorporated by reference). The theory behind nanopore sequencing has to do with what occurs when the nanopore is immersed in a conducting fluid and a potential (voltage) is applied across it: under these conditions a slight electric current due to conduction of ions through the nanopore can be observed, and the amount of current is exceedingly sensitive to the size of the nanopore. If DNA molecules pass (or part of the DNA molecule passes) through the nanopore, this can create a change in the magnitude of the current through the nanopore, thereby allowing the sequences of the DNA molecule to be determined.

HeliScope by Helicos BioSciences (Voelkerding et al., *Clinical Chem.*, 55: 641-658, 2009; MacLean et al., *Nature Rev. Microbiol.*, 7:287-296; 7,169,560; U.S. Pat. No. 7,282, 337; 7,482,120; 7,501,245; U.S. Pat. No. 6,818,395; 6,911, 345; 7,501,245; each herein incorporated by reference in their entirety) is the first commercialized single-molecule sequencing platform. This method does not require clonal amplification. Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run. Other emerging single molecule sequencing methods real-time sequencing by synthesis using a VisiGen platform (Voelkerding et al., *Clinical Chem.*, 55: 641-658, 2009; 7,329,492; U.S. patent application Ser. No. 11/671, 956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition. Another real-time single molecule sequencing system developed by Pacific Biosciences (Voelkerding et al., *Clinical Chem.*, 55: 641-658, 2009; MacLean et al., *Nature Rev. Microbiol.*, 7: 287-296; 7,170,050; U.S. Pat. No. 7,302, 146; 7,313,308; 7,476,503; all of which are herein incorporated by reference) utilizes reaction wells 50-100 nm in diameter and encompassing a reaction volume of approximately 20 zeptoliters ($10 \times 10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

Binding Matrix Solid Supports

The binding matrix employed in the present invention may be any surface or solid support to which the affinity-tag-binding molecule can be attached and which does not exhibit substantial non-specific binding of the affinity-tagged antisense rRNA molecules. The present invention is not limited to any one solid support. In some embodiments, polystyrene plates containing either 96 or 384 wells are employed. In some embodiments, streptavidin (SA) coated 96-well or 384-well microtiter plates (Boehringer Mannheim Biochemicals, Indianapolis, Ind.) are used as solid supports. In some embodiments, particles or beads are employed. The particles can be made of any suitable material, including, but not limited to, latex. In some embodiments, minicolumns are employed. The columns may contain affinity-tag-binding molecules. In other embodiments, a BEADARRAY (Illumina, San Diego, Calif.) is employed. A variety of other solid supports are contemplated including, but not limited to, glass microscope slides, glass wafers, gold, silicon, microchips, and other plastic, metal, ceramic, or biological surfaces.

EXAMPLES

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims.

Example 1

Synthesis of Biotinylated Antisense rRNA Molecules Representing the Full-Length Sequences of Ribosomal RNA (rRNA) Molecules of Eukaryotes and Prokaryotes In order to synthesize antisense rRNA corresponding to the complete sequence of each rRNA molecule, PCR templates were made containing a phage promoter sequence in all but one case as follows.

Human 18S, 5.8S and 5S rRNA PCR Templates for In Vitro Synthesis of Antisense rRNA PCR amplicons representing the full-length 18S (Accession# NR_003286), 5.8S (Accession# U13369 REGION: 6623-6779) and 5S (Accession # NR_023363) rRNA sequences were synthesized. Each 100-µl PCR reaction comprised 20 pmoles of a forward primer, 20 pmoles of a reverse primer containing T7 RNA polymerase phage promoter sequence (shown in italics) and 5 ng random primed first-strand cDNA made from Universal Human Reference total RNA (Stratagene) under FailSafe PCR reaction conditions optimized as described by the manufacturer (EPICENTRE Biotechnologies). The PCR amplification reactions were performed for 25 cycles to 30 cycles depending on the primer pair and the PCR amplicons corresponding to the full-length 18S, 5.8S and 5S rRNA sequences and PCR products were purified using the Qiaquick PCR purification kit as recommended by the manufacturer (Qiagen). The following is a list of the respective forward and reverse primers used:

```
18S rRNA
forward primer (SEQ ID NO: 1: 5'-CCTACCTACCTGGTTGA
TCC)
and reverse primer (SEQ ID NO: 2: 5'-AATTCTAATACGACTCA
CTATAGGGAGAGATCCTTCCGCAGGTTCACCTAC).

5.8S rRNA
forward primer (SEQ ID NO: 3: 5'-CGACTCTTAGCGGTGGA
TCACTC)
and reverse primer (SEQ ID NO: 4: 5'-AATTCTAATACGACTCA
CTATAGGGAGAGATCCTTCCGCAGGTTCACCTAC)

5S rRNA
forward primer (SEQ ID NO: 5: 5'-GTCTACGGCCATACCAC
CCTGAA)
and reverse primer (SEQ ID NO: 6: 5'-AATTCTAATACGACTCA
CTATAGGGAGAAAGCCTACAGCACCCGGTATTC)
```

*Escherichia coli* 23S, 16S and 5S rRNA PCR Templates for In Vitro Synthesis of Antisense rRNA PCR amplicons representing the full-length 23S (Accession# EG30077), 16S (Accession# EG30084) and 5S (Accession # EG30070) rRNA sequences were synthesized. Each 100 µl PCR reaction comprised 20 pmoles of a forward primer, 20 pmoles of a reverse primer containing T7 RNA polymerase phage promoter sequence (shown in italics) and 5 ng random primed first-strand cDNA made from *E. coli* K-12 total RNA under FailSafe PCR reaction conditions optimized as described by the manufacturer (EPICENTRE Biotechnologies). The PCR amplification reactions were performed for 25 cycles to 30 cycles depending on the primer pair and the PCR amplicons corresponding to the full-length 23S, 16S and 5S rRNA sequences and PCR products were purified using the Qiaquick PCR purification kit as recommended by the manufacturer (Qiagen). The following is a list of the respective forward and reverse primers used:

23S rRNA

In order to efficiently amplify the complete 23S rRNA sequence, two pairs of primers were used whereby, the full-length 23S rRNA sequence was divided into approximately two equal segments. The 5' 23S rRNA segment comprised forward primer (SEQ ID NO: 7: 5'-AAGC-GACTAAGCGTACACGGTGGA) and reverse primer (SEQ ID NO: 8: 5'-AATTCTAATACGACTCAC-TATAGGGAGATTCCTGGAAGCAGG GCATTTGTTG) and the 3' 23S rRNA segment comprised forward primer (SEQ ID NO: 9: 5'-CAACAAATGCCCTGCTTCCAG-GAA) and reverse primer (SEQ ID NO: 10: 5'-AAT-TCTAATACGACTCACTATAGGGAGACACGGT-TCATTAGTACCGGTTAGCT).

```
16S rRNA
forward primer (SEQ ID NO: 11: 5'-AGAGTTTGATCCTGGC

TCAG)
and reverse primer (SEQ ID NO: 12: 5'-AATTCTAATACGACTC

ACTATAGGGAGAGGAGGTGATCCAACCGCAGGTT).

5S rRNA
forward primer (SEQ ID NO: 13: 5'-TGCCTGGCGGCAGTAG

CGCGGT)
and reverse primer (SEQ ID NO: 14: 5'-AATTCTAATACGACTC

ACTATAGGGAGATGCCTGGCAGTTCCCTACTCTC).
```

Each PCR amplicon (300 ng) representing the respective human or *E. coli* rRNA sequence was analyzed by ethidium bromide stained agarose gel electrophoresis as shown in FIG. 1A.

Human 28S Ribosomal RNA Clone

PCR amplification of the complete 28S rRNA (Accession# NR_003287) sequence was found not to be very efficient, especially for the approximately 1200-nt 5'-end sequence, even after dividing the full-length sequence into segments ranging from 1 Kb to 2 Kb. Thus, in order to generate the required template for in vitro synthesis of the 28S antisense rRNA, the 28S rRNA sequence was cloned into both a T7 phage promoter-containing plasmid (pSP73; Promega Corporation) and a SP6 phage promoter-containing plasmid (pSP64; Promega Corporation) using standard cloning methods and strategies (Maniatis et. al. (1982) *Molecular Cloning, A Laboratory Manual*. Cold Spring Harbor Laboratory, Cold Spring Harbor, N.Y. and information described by Maden et. al. (1987) Biochem. J. 246: 519-527.

In Vitro Synthesis of Biotinylated Antisense rRNA Molecules from the Respective PCR Templates for Human 18S, 5.8S and 5S and *E. coli* 23S, 16S and 5S rRNA Sequences Either an AmpliScribe™ T7 High Yield Transcription Kit or an AmpliScribe™ T7-FLASH Transcription Kit (EPICENTRE, Madison, Wis.) was used for in vitro transcription (IVT) reactions comprising 500 ng to 1000 ng of the respective templates (human 18S, 5.8S and 5S and *E. coli* 23S, 16S and 5S) were performed as described by the manufacturer (EPICENTRE Biotechnologies) with the following modification—the uridine triphosphate (UTP) was replaced with mixtures of biotin-16-UTP and UTP comprising 10%, 20%, 35%, 50% or 60% biotin-16-UTP. The IVT reactions were incubated at 37° C. for 4 to 6 hours and the DNA template used in each reaction was then digested with DNase I as recommended by the manufacturer. Each biotinylated antisense rRNA was subsequently purified using illustra RNAspin Mini columns as recommended by the manufacturer (GE Healthcare) and eluted in RNase-free water. Each purified antisense rRNA was treated with Baseline-Zero™ DNase I as recommended by the manufacturer (EPICENTRE Biotechnologies) to remove all traces of the DNA template used for transcription. The biotinylated antisense rRNA was again purified using illustra RNAspin Mini columns, eluted in RNase-free water and the RNA concentration determined by measuring the absorbance at 260 nm with a spectrophotometer. (Note: subsequent experiments showed that best results for generating rRNA-depleted samples with respect to 5.8S and 5S eukaryotic rRNA or 5S prokaryotic rRNA were obtained using at least about 75% biotin-16-UTP in the in vitro transcription reaction.)

Figure 1B:
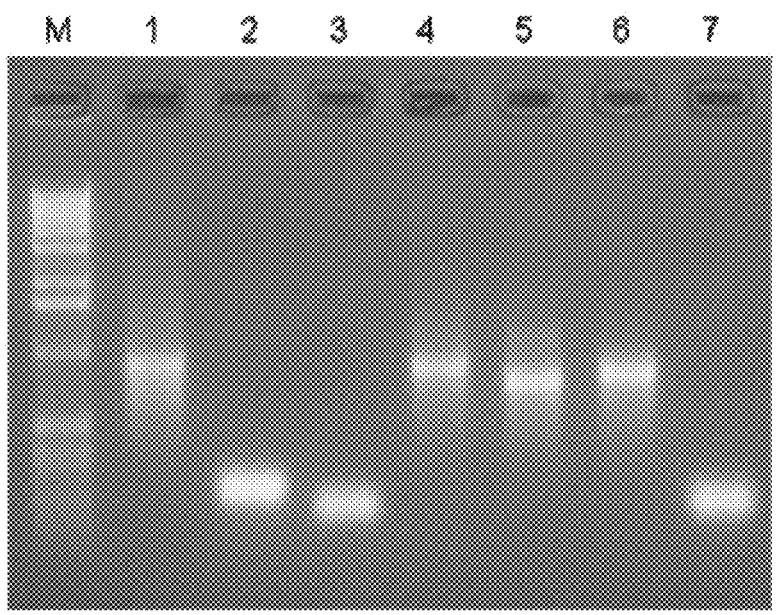
FIG. 1B shows an ethidium bromide stained agarose gel containing the following antisense sequences: Lane M—DNA molecular weight ladder; Lane 1—300 ng of human antisense 18S rRNA; Lane 2—300 ng of human antisense 5.8S rRNA; Lane 3—300 ng of human antisense 5S rRNA; Lane 4—300 ng of *E. coli* antisense 23S rRNA 5' segment; Lane 5—300 ng of *E. coli* antisense 23S rRNA 3' segment; Lane 6—300 ng of *E. coli* antisense 16S rRNA; and Lane 7—300 ng of *E. coli* antisense 5S rRNA.

Each purified antisense RNA (300 ng), representing the entire human or *E. coli* rRNA sequence, as analyzed by ethidium bromide stained agarose gel electrophoresis, is shown in FIG. 1B.

In Vitro Synthesis of Biotinylated Antisense rRNA from the Plasmid Templates for Human 28S rRNA Sequence Initially, 1 µg of the linearized T7-28S rRNA plasmid clone was used in an AmpliScribe™ T7 High Yield Transcription Kit for in vitro transcription (IVT) as described by the manufacturer (EPICENTRE Biotechnologies) with the following modification—a 1:1 mixture of bio-UTP:UTP instead of 100% UTP. Incubation was performed at 37° C. for 4 hours and the DNA template then removed by digesting with DNase I as recommended by the manufacturer (EPICENTRE Biotechnologies). An aliquot (300 ng) of the purified transcription reaction product was analyzed by gel electrophoresis. It was evident from the results (FIG. 1C, Lane 1) that very little, if any of the expected full-length antisense 28S rRNA was produced in the IVT reaction. Instead, RNA molecules ranging in size from low to high molecular weights were observed. Thus, it appeared that the T7 RNA polymerase was unable to efficiently transcribe the 28S DNA template.

Figure 1C:
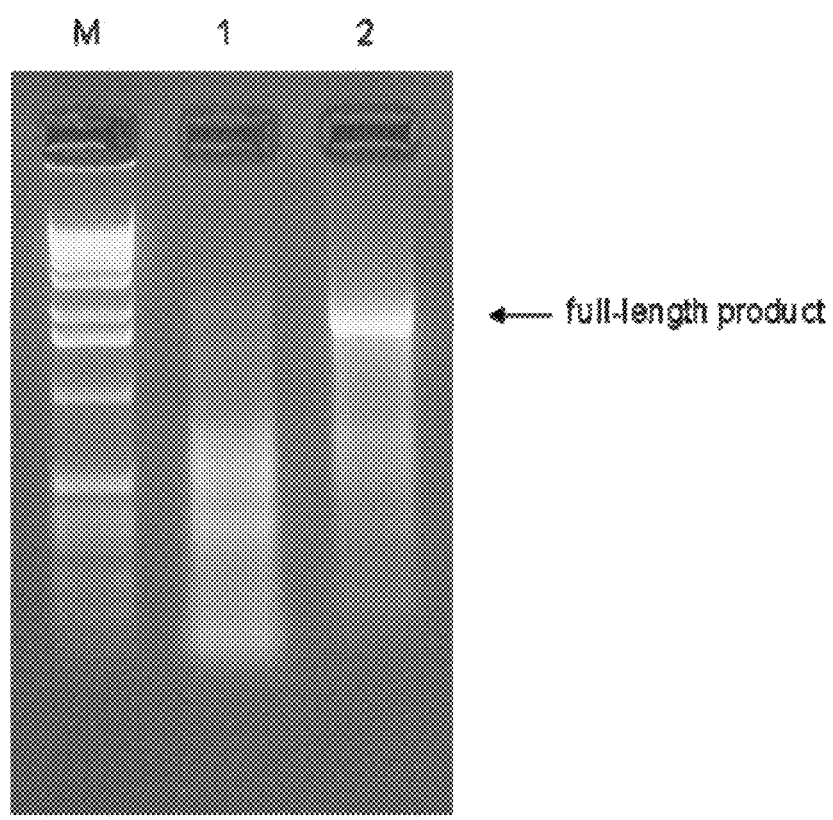
FIG. 1C shows an ethidium bromide stained agarose gel containing the following lanes: Lane M—DNA molecular weight ladder; Lane 1—300 ng of T7-based 28S biotinylated antisense rRNA; and Lane 2—300 ng of SP6-based 28S biotinylated antisense rRNA.

Next, 1 µg of the linearized SP6-28S rRNA plasmid clone was tested in a standard AmpliScribe™ SP6 High Yield Transcription Kit for in vitro transcription (IVT) as described by the manufacturer (EPICENTRE Biotechnologies) using a similar 1:1 mixture of bio-UTP and UTP. Incubation was performed at 37° C. for 4 hours and the DNA template then removed by digesting with DNase I as recommended by the manufacturer (EPICENTRE Biotechnologies). The biotinylated antisense rRNA produced was subsequently purified using illustra RNAspin Mini columns as recommended by the manufacturer (GE Healthcare) and eluted in RNase-free water. Thereafter, the purified antisense 28S rRNA was treated with Baseline-Zero™ DNase I as recommended by the manufacturer (EPICENTRE Biotechnologies) to remove all traces of the DNA template used for transcription. The biotinylated antisense rRNA was again purified using illustra RNAspin Mini columns, eluted in RNase-free water and the RNA concentration determined by measuring the absorbance at 260 nm with a spectrophotometer. An aliquot (300 ng) of the transcription reaction was analyzed by gel electrophoresis and it was evident from the results that the expected antisense 28S rRNA was produced in the SP6-IVT reaction (FIG. 1C, Lane 2).

Example 2

Removal of Biotinylated Antisense rRNA and Resulting Ds-rRNA Hybrids Formed Using *E. coli* Total RNA Using Streptavidin-Coated Microspheres

*E. coli* rRNA was used as the model to test the amount of ProActive® Streptavidin Coated Microspheres (Bangs Laboratories) needed to remove a fixed quantity biotinylated antisense rRNA from solution. The streptavidin-coated microspheres were washed and resuspended in the bind/wash buffer as recommended by the manufacturer (Bangs Laboratories). *E. coli* biotinylated antisense rRNA materials synthesized using 35% biotin-UTP as described in Example 1 were used to prepare a mixture comprising one microgram each of the 23S rRNA 5' segment, the 23S rRNA 3' segment and the full-length 16S rRNA in a 4-μl volume of RNase-free water. Each 4-μl biotinylated antisense rRNA mixture would represent at least a >2-fold molar excess when mixed with one microgram of native *E. coli* total RNA, which concentration was selected to drive the hybridization of the sense and antisense rRNA to completion or near completion when mixed together.

The amount of streptavidin-coated microspheres required to efficiently remove the added biotinylated antisense rRNA added to a hybridization reaction was determined. Three 4-μl aliquots of the *E. coli* biotinylated antisense rRNA mixture were prepared in 0.2 ml microcentrifuge tubes to a final reaction volume of 20 μl comprising 1× hybridization buffer (50 mM Tris-HCl, pH7.5 and 100 mM NaCl). The reactions were incubated at 68° C. for 5 minutes and then at room temperature for 15 minutes. Reactions #1 and #2 were each then added to a fresh 1.5-ml microcentrifuge tube containing 20 μl of the washed and resuspended streptavidin-coated microspheres. Control reaction #3 was added to a fresh 1.5-ml microcentrifuge tube with only 20 μl bind/wash buffer. All reactions were further incubated at room temperature for 15 minutes with occasional gentle mixing (3-4 minutes) in order to allow formation of the biotin-streptavidin complex. The biotinylated antisense rRNA remaining in solution following capture by the microspheres was then purified using RNA Clean-up Kit™-5 columns as recommended by the manufacturer (ZYMO Research). Reactions #1 and #3 were added directly in the ZYMO RNA Clean-up procedure whereas, reaction #2 was first spun at 12,000 rpm for 5 minutes using a benchtop centrifuge to pellet the microspheres and the supernatant removed and then added to the ZYMO RNA Clean-up procedure. Each RNA sample was eluted in 10 μl RNase-free water and a 5-μl aliquot analyzed by ethidium bromide stained agarose gel electrophoresis as shown in FIG. 2A.

Figure 2A:
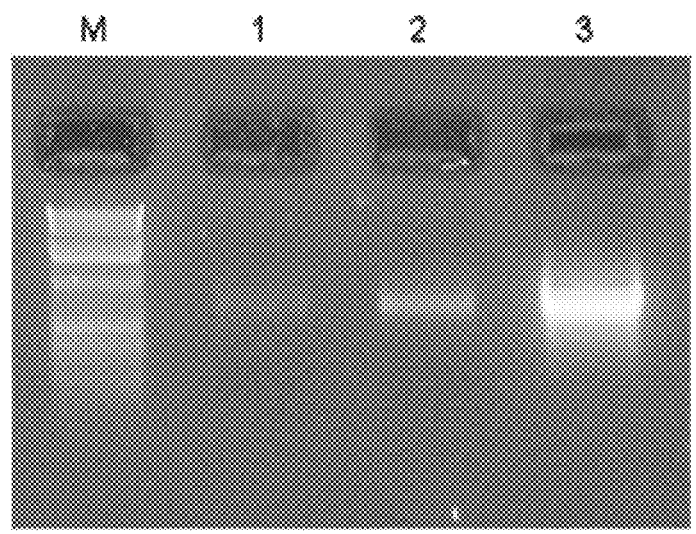
FIG. 2A shows the following: Lane M—DNA molecular weight ladder; Lane 1—Biotinylated antisense rRNA following purification with microspheres directly on column; Lane 2—Biotinylated antisense rRNA following purification from supernatant after removal of microspheres; and Lane 3—Biotinylated antisense rRNA control.

FIG. 2A, lanes 1 and 2 show the residual biotinylated antisense rRNA following binding to the streptavidin coated microspheres compared to the control (Lane 3). The amount of antisense RNA remaining was more pronounced in Lane 2 where the microspheres were removed prior to the ZYMO RNA clean-up procedure. While unclear, it is possible that adding the hybridization reaction mixture with the microspheres directly to the RNA purification column reduced the binding capacity of the column resulting in a further loss of the biotinylated antisense RNA. Nevertheless, it was evident from this experiment that 20 μl of the streptavidin coated microspheres was insufficient to remove the entire amount of biotinylated antisense rRNA used.

Thus, an additional 20 μl of washed microspheres was tested to determine if it would be sufficient to remove the 4 μl of biotinylated antisense rRNA. Four reactions, each comprising 4 μl of the *E. coli* biotinylated antisense rRNA were prepared in 1× hybridization buffer to a final volume of 20 μl. The reactions were incubated at 68° C. for 5 minutes and then at room temperature for 15 minutes. Each of reactions #2 and #3 was added to a fresh 1.5-ml microcentrifuge tube containing 20 μl of the washed and resuspended streptavidin-coated microspheres. Reaction #4 was added to a fresh 1.5-ml microcentrifuge tube containing 40 μl of the washed and resuspended streptavidin-coated microspheres. Control reaction #1 was added to a fresh 1.5-ml microcentrifuge tube with only bind/wash buffer. The reactions were further incubated at room temperature for 15 minutes with occasional gentle mixing (3-4 minutes) in order to allow formation of the biotin-streptavidin complex. The reactions were spun at 12,000 rpm for 5 minutes using a benchtop centrifuge to pellet the microspheres and each supernatant transferred to a fresh 1.5-ml microcentrifuge tubes. To the supernatant of reaction #3, an additional 20 μl of the washed streptavidin-coated microspheres was added and again incubated at room temperature with occasional gentle mixing (3-4 minutes). Reaction #3 was centrifuged at 12,000 rpm for 5 minutes once more and the supernatant transferred to a fresh 1.5-ml microcentrifuge tube. The biotinylated antisense RNA contained in each of the four reactions was purified using the ZYMO RNA Clean-up procedure and eluted in 10 μl RNase-free water. The entire eluate for each was analyzed by ethidium bromide stained agarose gel electrophoresis as shown in FIG. 2B.

FIG. 2B, lane 2 again shows that biotinylated antisense rRNA is not completely removed when only 20 μl of microspheres is used. However, when either 20 μl of microspheres followed by a second 20 μl of microspheres or 40 μl of microspheres was used, there appears to be complete removal of the added biotinylated antisense rRNA (Lane 3 and Lane 4, respectively). Thus, the one treatment with 40 μl of microspheres was generally preferred since it required fewer steps.

Figure 2B:
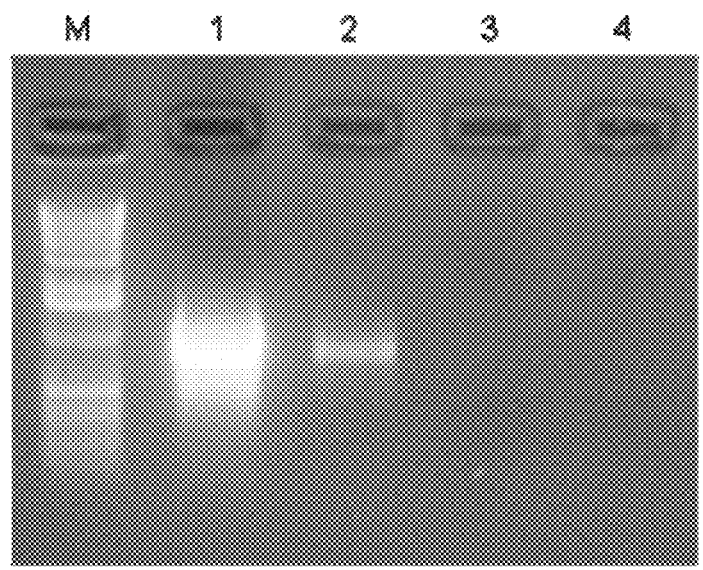
FIG. 2B shows the following: Lane M—DNA molecular weight ladder; Lane 1—Biotinylated antisense rRNA control; Lane 2—Biotinylated antisense rRNA following purification after 20 μl of microspheres; Lane 3—Biotinylated antisense rRNA following purification after 2×20 μl of microspheres; and Lane 4—Biotinylated antisense rRNA following purification after 40 μl of microspheres

Next, the amount of microspheres used as described in FIG. 2B was tested to determine if it was also sufficient to efficiently remove the double-stranded ribosomal RNA (ds-rRNA) hybrids formed after annealing the biotinylated antisense rRNA and the native rRNA contained in total RNA. Firstly, in order to demonstrate the formation of the ds-rRNA hybrid, 500 ng of *E. coli* total RNA was mixed with 4 μl of the *E. coli* biotinylated antisense rRNA in a reaction comprising 1× hybridization buffer in a final volume of 20 μl. The reaction was incubated at 68° C. for 5 minutes and then at room temperature for 15 minutes, purified using the ZYMO RNA Clean-up procedure and eluted in 10 μl RNase-free water. A 5-μl aliquot was analyzed by ethidium bromide stained agarose gel electrophoresis along with equivalent amounts of the individual *E. coli* total RNA and biotinylated antisense rRNA as shown in FIG. 2C. FIG. 2C, lane 3 shows the efficient formation of the ds-rRNA hybrids compared to the individual sense and antisense RNA samples (Lanes 1 and 2, respectively).

Next, the removal of the ds-rRNA hybrids was tested using the quantities of washed microspheres described in FIG. 2B. Three reactions (#1, #2 and #3), each comprising 500 ng of E. coli total RNA and 4 µl of the E. coli biotinylated antisense rRNA in 1× hybridization buffer in a final volume of 20 µl were prepared, along with two control reactions—one containing only the E. coli biotinylated antisense rRNA (#4) and the other, only the E. coli total RNA (#5). The reactions were incubated at 68° C. for 5 minutes and then at room temperature for 15 minutes. Reactions #1 and #3 were each added to a fresh 1.5-ml microcentrifuge tube containing 20 µl of the washed and resuspended streptavidin-coated microspheres. Reactions #2 and #4 were each added to a fresh 1.5-ml microcentrifuge tube containing 40 µl of the washed and resuspended streptavidin-coated microspheres. Control reaction #5 was added to a fresh 1.5-ml microcentrifuge tube containing only bind/wash buffer. The reactions were further incubated at room temperature for 15 minutes with occasional gentle mixing (3-4 minutes) in order to allow formation of the biotin-streptavidin complex. The reactions were spun at 12,000 rpm for 5 minutes using a benchtop centrifuge to pellet the microspheres and each supernatant transferred to a fresh 1.5-ml microcentrifuge tubes. To the supernatant of reaction #3, an additional 20 µl of the washed streptavidin-coated microspheres was added and incubated at room temperature with occasional gentle mixing (3-4 minutes). Reaction #3 was again centrifuged at 12,000 rpm for 5 minutes and the supernatant transferred to a fresh 1.5-ml microcentrifuge tube. The RNA contained in each of the five reactions was purified using the ZYMO RNA Clean-up procedure and eluted in 10 µl RNase-free water. A 5-µl aliquot of each was analyzed by ethidium bromide stained agarose gel electrophoresis as shown in FIG. 2D. In addition, 250 ng of untreated E. coli total RNA was run as a control.

FIG. 2D, Lane 1 shows the residual ds-rRNA when only 20 µl of microspheres was used. However, with either 2×20 µl (Lane 2) or 1×40 µl of microspheres (Lane 3), the ds-rRNA hybrids were no longer visible indicating that the biotinylated antisense rRNA was capable of annealing to its complementary sense rRNA sequences and facilitate their removal by the streptavidin microspheres. The quantity of E. coli total RNA did not appear to be affected by the addition of 40 µl of microspheres (Lane 5) when compared to a similar amount of untreated E. coli total RNA (Lane 6). Thus, it was evident that 40 µl of microspheres was sufficient to remove either the added biotinylated antisense rRNA or the resulting ds-rRNA hybrids formed after hybridization of the biotinylated antisense rRNA to the rRNA.

Example 3

Effect of Using Different Levels of Biotin-UTP for Synthesis of Biotinylated Antisense rRNA and its Removal with the Streptavidin Coated Microspheres The experiments described in Example 2 above used biotinylated antisense rRNA synthesized using a UTP:biotin-UTP mixture comprising 35% biotin-UTP. For the amount of antisense rRNA used in the hybridization reaction, 40 µl of the strepavidin microspheres was needed for its efficient removal. Thus, it was thought that antisense rRNA made with lesser amounts of biotin-UTP should require less streptavidin microspheres for its quantitative removal, which would result in an overall reduction in the cost associated with the amount of both the biotin-UTP and microspheres required. Biotinylated antisense 16S and 23S rRNA were prepared using either 10% or 20% biotin-UTP solutions as described above in Example 1 and standard 4-µl mixtures of the respective biotinylated antisense rRNA were then made. The percentage of biotin-UTP used in the in vitro transcription reaction for its synthesis is used to refer to the biotinylated antisense rRNA product; for example, if the percentage of biotin-UTP used in the in vitro transcription reaction is 10%, with the remaining 90% being UTP, the product is referred to herein as 10% biotinylated antisense rRNA, even though the percentage of biotin-UTP nucleotides incorporated into the product may be less than 10% compared to the UTP nucleotides incorporated into the product.

Two sets of three reactions each comprising 4 µl of either the 10% (reaction #1, #2 and #3) or 20% (reactions #4, #5 and #6) biotinylated antisense rRNA mixture were prepared in a final volume of 20 µl in 1× hybridization buffer. The reactions were incubated at 68° C. for 5 minutes and then at room temperature for 15 minutes. Reactions #2 and #5 were each transferred to a fresh 1.5-ml microcentrifuge tube containing 20 µl of washed streptavidin microspheres and reactions #3 and #6 were each transferred to a fresh 1.5-ml microcentrifuge tube containing 40 µl of washed streptavidin microspheres. Reactions #1 and #4 were each transferred to a fresh 1.5-ml microcentrifuge tubes containing 40 µl of bind/wash buffer. The reactions were further incubated at room temperature for 15 minutes with occasional gentle mixing (3-4 minutes) in order to allow formation of the biotin-streptavidin complex. The reactions were spun at 12,000 rpm for 5 minutes on a benchtop centrifuge and the supernatant transferred to fresh 1.5-ml microcentrifuge tubes. Any biotinylated antisense rRNA remaining in the supernatants were purified using the ZYMO RNA Clean-up procedure and eluted in 10 µl RNase-free water. The entire amount of each purified sample was analyzed by ethidium bromide stained agarose gel electrophoresis as shown in FIG. 3A.

Figure 3A:
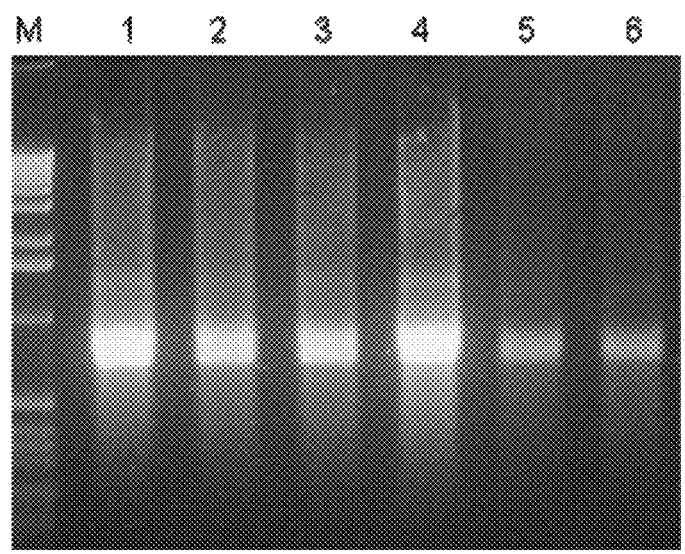
FIG. 3A shows the following: Lane M—DNA molecular weight ladder; Lane 1—10% biotinylated antisense rRNA minus microspheres; Lane 2—10% biotinylated antisense rRNA plus 20 μl microspheres; Lane 3—10% biotinylated antisense rRNA plus 40 μl microspheres; Lane 4—20% biotinylated antisense rRNA minus microspheres; Lane 5—20% biotinylated antisense rRNA plus 20 μl microspheres; and Lane 6—20% biotinylated antisense rRNA plus 40 μl microspheres.

FIG. 3A, Lanes 1 and 4 show the 10% and 20% biotinylated antisense rRNA not treated with microspheres, respectively. Lanes 2 and 3 show the 10% biotinylated antisense rRNA treated with 20 µl and 40 µl of microspheres, respectively. Lanes 5 and 6 show the 20% biotinylated antisense rRNA treated with 20 µl and 40 µl of microspheres, respectively. Clearly, there was a significant amount of both the 10% and 20% biotinylated antisense rRNA remaining independent of either 20 µl or 40 µl of microspheres used (Lanes 2, 3, 5 and 6). Nevertheless, the 20% condition (Lanes 5 and 6) was clearly better than the 10% condition (Lanes 2 and 3). Thus, it appeared that using these lower levels of biotin-UTP were used to synthesize the biotinylated rRNA, at least some of the antisense rRNA product synthesized may not contain sufficient biotin molecules to facilitate its removal by the streptavidin microspheres.

Thus, the question arose as to whether the 35% biotin-UTP used in Example 2 was the optimal concentration to ensure that all antisense rRNA synthesized contained sufficient biotin molecules for its subsequent removal by the streptavidin beads. To answer this question, the following experiment tested biotinylated antisense rRNAs made as described in Example 1 using either 50% or 60% biotin-UTP solutions. The standard 4-µl mixture of the respective biotinylated antisense 16S and 23S rRNA synthesized using the 50% and 60% levels of biotin-UTP was then made. The standard 4 µl-mixture of the 35% biotinylated antisense rRNA included as a control.

Three sets of two reactions, each comprising 4 µl of the 35% (reactions #1 and #2) or 50% (reactions #3 and #4) or 60% (reactions #5 and #6) biotinylated antisense rRNA mixture were prepared in a final volume of 20 µl in 1× hybridization buffer. The reactions were incubated at 68° C. for 5 minutes and then at room temperature for 15 minutes. Reactions #2, #4 and #6 were each transferred to a fresh 1.5-ml microcentrifuge tube containing 40 µl of washed streptavidin microspheres and reactions #1, #3 and #5 were each transferred to a fresh 1.5-ml microcentrifuge tube containing 40 µl of bind/wash buffer. All reactions were further incubated at room temperature for 15 minutes with occasional gentle mixing (3-4 minutes) in order to allow formation of the biotin-streptavidin complex. The reactions were spun at 12,000 rpm for 5 minutes on a benchtop centrifuge and the supernatant transferred to fresh 1.5-ml microcentrifuge tubes. Any biotinylated antisense rRNA remaining in the supernatants were purified using the ZYMO RNA Clean-up procedure and eluted in 13.5 µl RNase-free water. Fifty percent of each purified sample was analyzed by ethidium bromide-stained agarose gel electrophoresis as shown in FIG. 3B.

Figure 3B:
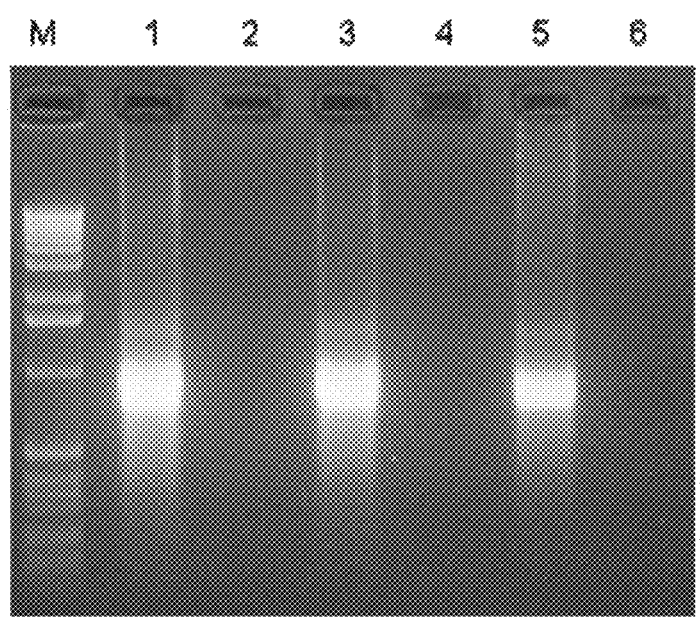
FIG. 3B shows the following: Lane M—DNA molecular weight ladder; Lane 1—35% biotinylated antisense rRNA minus streptavidin microspheres; Lane 2—35% biotinylated antisense rRNA plus streptavidin microspheres; Lane 3—50% biotinylated antisense rRNA minus streptavidin microspheres; Lane 4—50% biotinylated antisense rRNA plus streptavidin microspheres; Lane 5—60% biotinylated antisense rRNA minus streptavidin microspheres; and Lane 6—60% biotinylated antisense rRNA plus streptavidin microspheres.

FIG. 3B, Lanes 1, 3 and 5 show the biotinylated antisense rRNA remaining in the absence of any microspheres for the 35%, 50% and 60% biotin-UTP samples, respectively. With the addition of 40 µl of streptavidin microspheres, there was no biotinylated antisense rRNA visibly remaining in any of the corresponding reactions (Lanes 2, 4 and 6). It was not possible to observe any differences in the performance of the 35%, 50% and 60% biotinylated antisense rRNA samples following treatment with 40 µl of the streptavidin microspheres by agarose gel analysis.

In order to further determine if there was a difference between the use of the 35%, 50% and 60% biotinylated antisense rRNA, the remaining half of each reaction was converted to first-strand cDNA in a standard reverse transcriptase reaction containing random hexamers and purified using the Qiaquick PCR purification kit as recommended by the manufacturer (Qiagen). A 5-µl aliquot of each was then used in separate PCR amplification reactions containing primers specific to the terminal 5' and 3' regions of 23S (SEQ ID NO: 15: 5'-GACGTGCTAATCTGCGATAAGC, SEQ ID NO: 16: 5'-ATGGATTCAGTTAATGATAGTGTGTCG, SEQ ID NO: 17: 5'-CTGAAAGCATCTAAGCAC-GAAACTTGC and SEQ ID NO: 18: 5'-CCTAT-CAACGTCGTCGTCTTCAAC) and 16S (SEQ ID NO: 19: 5'-GCCTAACACATGCAAGTCGAAC, SEQ ID NO: 20: 5'-AGCTACCGTTTCCAGTAGTTATCC, SEQ ID NO: 21: 5'-CGGAATCGCTAGTAATCGTGGAT and SEQ ID NO: 22: 5'-TCCCGAAGGTTAAGCTACCTACTT) rRNAs for 20 PCR cycles. PCR amplification is notably more sensitive than ethidium bromide agarose gel analysis and should therefore better demonstrate any differences between the removal efficiencies of the 35%, 50% and 60% biotinylated antisense rRNA by the microspheres. The results are shown in FIG. 3C.

Figure 3C:
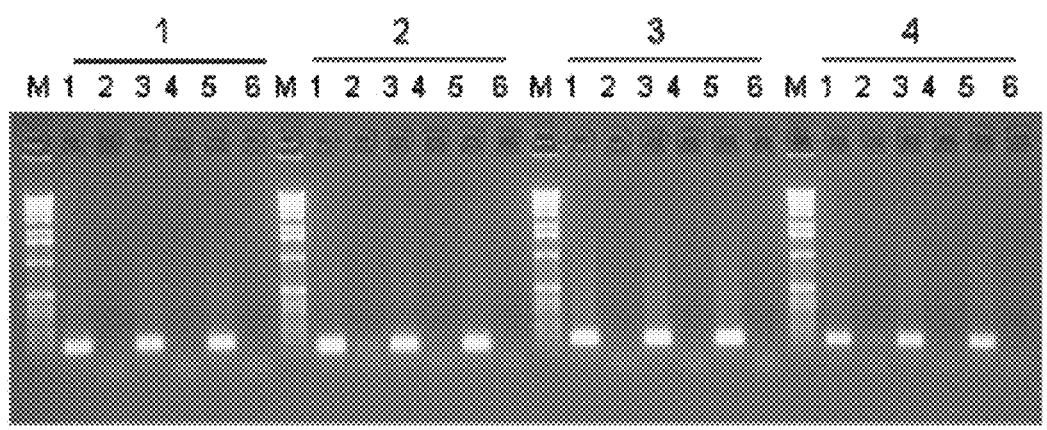
FIG. 3C shows the following: Lane M—DNA molecular weight ladder; Lane 1—PCR of 35% biotinylated antisense rRNA minus streptavidin microspheres; Lane 2—PCR of 35% biotinylated antisense rRNA plus streptavidin microspheres; Lane 3—PCR of 50% biotinylated antisense rRNA minus streptavidin microspheres; Lane 4—PCR of 50% biotinylated antisense rRNA plus streptavidin microspheres; Lane 5—PCR of 60% biotinylated antisense rRNA minus streptavidin microspheres; and Lane 6—PCR of 60% biotinylated antisense rRNA plus streptavidin microspheres. Panel 1 shows 5'-23S rRNA primers. Panel 2 shows 3'-23S rRNA primers. Panel 3 shows 5'-16S rRNA primers. Panel 4 shows 3'-16S rRNA primers.

FIG. 3C, Lanes 1, 3 and 5 show the expected PCR amplicons for the 5' 23S rRNA (Panel 1), 3' 23S rRNA (Panel 2), 5' 16S rRNA (Panel 3) and 3' 16S rRNA (Panel 4) with the 35%, 50% and 60% biotinylated antisense rRNA mixtures, respectively. Lanes 2, 4 and 6 show the corresponding PCR reaction products following the use of the streptavidin microspheres. As seen in Lane 2 (Panels 2 and 4), residual carryover of 35% biotinylated antisense rRNA resulted in still some specific PCR-amplified products that were not observed with the 50% and 60% biotinylated antisense rRNA materials. Both the 50% and 60% biotinylated antisense rRNA materials behaved similarly and thus, the 50% condition was selected.

Example 4

Removal of the 23S and 16S rRNA from Another Prokaryotic Species (*Lactobacillus plantarum*) Using the *E. coli* Biotinylated Antisense 23S and 16S rRNA Mixture In order to test if the *E. coli* biotinylated antisense rRNA mixture would be capable of removing the 23S and 16S rRNA sequences exhibited by a relatively diverse prokaryotic species, total RNA from *Lactobacillus plantarum*, which shares approximately 80% homology with *E. coli* 16S and 23S rRNA was used. In one reaction, 500 ng of *L. plantarum* total RNA was mixed with 4 µl of the *E. coli* biotinylated antisense rRNA mixture described in Example 2 above in 1× hybridization buffer in a final volume of 20 µl. A second reaction to serve as a control contained everything as the first reaction minus the *E. coli* biotinylated antisense rRNA mixture. The reactions were incubated at 68° C. for 10 minutes and then at room temperature for 15 minutes. Each reaction was then added to a fresh 1.5-ml microcentrifuge tube containing 50 µl of washed and resuspended streptavidin-coated microspheres. The reactions were further incubated at room temperature for 15 minutes with occasional gentle mixing (3-4 minutes) in order to allow for formation of the biotin-streptavidin complex. The reactions were then spun at 12,000 rpm for 5 minutes using a benchtop centrifuge to pellet the microspheres, the supernatant removed and the RNA purified using the ZYMO RNA Clean-up procedure. Each RNA sample was eluted in 13.5 µl RNase-free water and 50% of each analyzed by ethidium bromide stained agarose gel electrophoresis as shown FIG. 4.

Figure 4:
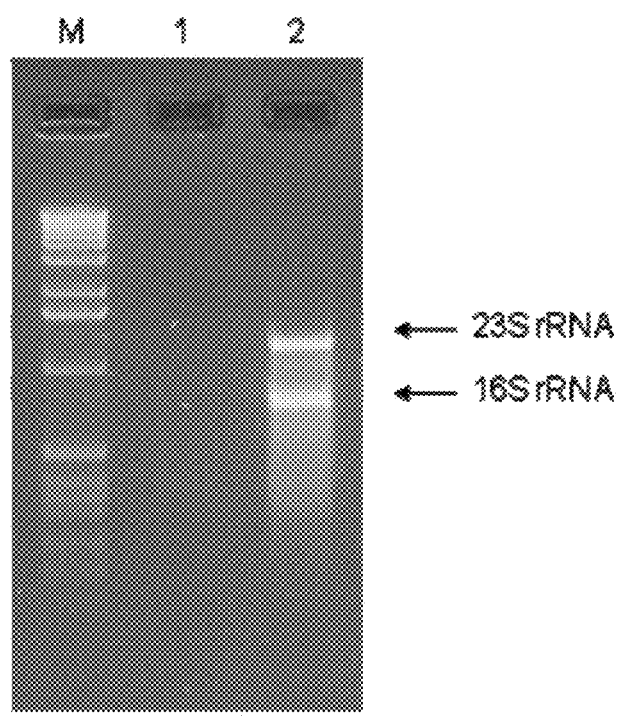
FIG. 4 shows the following: Lane M—DNA molecular weight ladder; Lane 1—*L. plantarum* total RNA plus *E. coli* biotinylated antisense rRNA mixture subtraction; and Lane 2—*L. plantarum* total RNA minus *E. coli* biotinylated antisense rRNA mixture subtraction.

FIG. 4, Lane 1 compared to Lane 2 shows that both the 16S and 23S rRNA bands for *L. plantarum* were no longer visible following subtraction with the *E. coli* biotinylated antisense rRNA mixture indicating that they were efficiently subtracted as well even though the rRNA sequences were only 80% homologous.

Example 5

Removal of 23S, 16S and 5S rRNA from a Range of Inputs of *E. coli* Total RNA Using the *E. coli* Biotinylated Antisense rRNA Mixture An *E. coli* biotinylated antisense rRNA mixture was prepared, now containing 23S, 16S and 5S antisense rRNA, and the following reactions for generating rRNA-depleted samples and control reactions were set up as shown in Table 1, and were performed in duplicate in a final volume of 20 µl in 1× hybridization buffer:

TABLE 1

| Reaction # | *E. Coli* total RNA Inputs | *E. coli* biotinylated antisense rRNA mixture (23S, 16S, 5S) | Streptavidin coated microspheres |
|---|---|---|---|
| 1, 2 | 50 ng | 2 µl | 25 µl |
| 3, 4 | 100 ng | 2 µl | 25 µl |
| 5, 6 | 500 ng | 4 µl | 50 µl |
| 7, 8 | 1000 ng | 4 µl | 50 µl |
| 9, 10 | 2500 ng | 8 µl | 100 µl |

TABLE 1-continued

| Reaction # | E. Coli total RNA Inputs | E. coli biotinylated antisense rRNA mixture (23S, 16S, 5S) | Streptavidin coated microspheres |
|---|---|---|---|
| 11, 12 | 5000 ng | 10 µl | 125 µl |
| 13, 14 | 500 ng | — | 50 µl |

The reactions were incubated at 68° C. for 10 minutes and then at room temperature for 15 minutes. Each reaction was then added to a fresh 1.5-ml microcentrifuge tube containing the appropriate quantity of washed and resuspended streptavidin-coated microspheres. The reactions were further incubated at room temperature for 15 minutes with occasional gentle mixing (3-4 minutes) in order to allow for formation of the biotin-streptavidin complex. The reactions were then spun at 12,000 rpm for 5 minutes using a benchtop centrifuge to pellet the microspheres and the supernatant removed and the RNA purified using the ZYMO RNA Clean-up procedure. Each RNA sample was eluted in 13.5 µl RNase-free water. The entire RNA sample for each was then converted to first-strand cDNA in a standard reverse transcriptase reaction containing random hexamers and purified using the Qiaquick PCR purification kit as recommended by the manufacturer (Qiagen). A 5-µl aliquot of each first-strand cDNA sample was used in separate PCR amplification reactions containing primers specific to the terminal 5' regions of 23S (SEQ ID NO: 15 and SEQ ID NO: 16) and 16S rRNA (SEQ ID NO: 19 and SEQ ID NO: 20), the complete 5S rRNA (SEQ ID NO: 13 and SEQ ID NO: 23: 5'-TGCCTGGCAGTTCCCTACTCTC) and the ompA mRNA (SEQ ID NO: 24: 5'-ACCAGGTTAACCCGTATGT-TGGCT and SEQ ID NO: 25: 5'-ACCGATGTTGTTGGTC-CACTGGTA) for 20 cycles. A control reaction minus template was also performed for each primer pair. A 5-µl aliquot of each PCR reaction was analyzed by ethidium bromide stained agarose gel electrophoresis as shown in FIG. 5.

Figure 5:
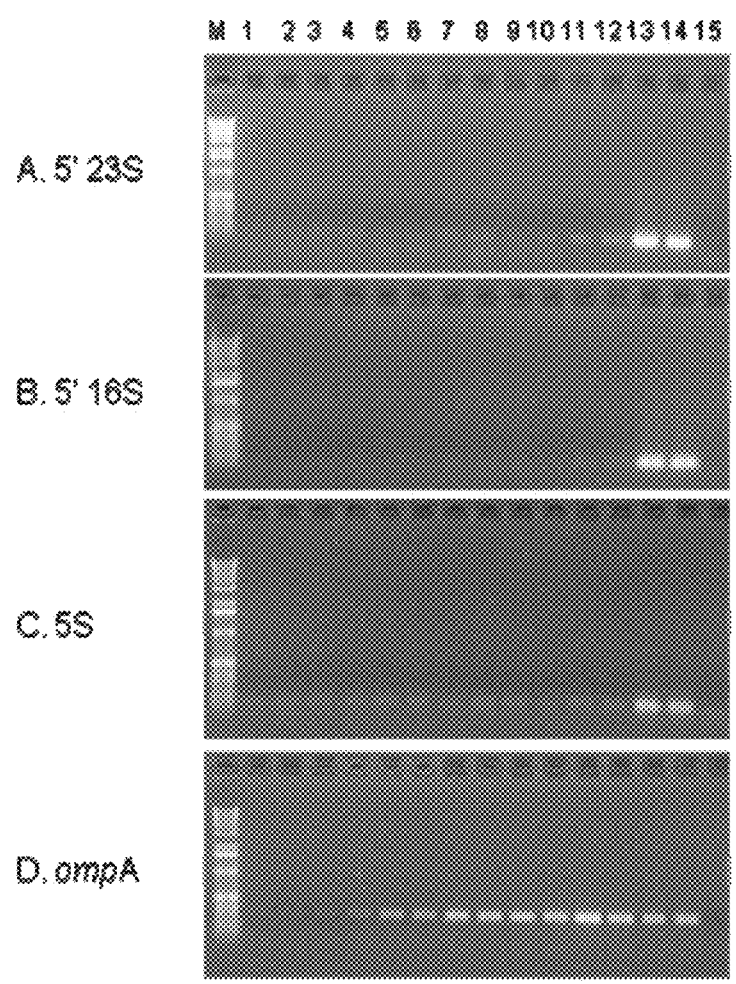
FIG. 5, panels A-D, showing the following: Lane M—DNA molecular weight ladder; Lanes 1, 2—PCR result for 50 ng input *E. coli* total RNA plus subtraction; Lanes 3,4—PCR result for 100 ng input *E. coli* total RNA plus subtraction; Lanes 5, 6—PCR result for 500 ng input *E. coli* total RNA plus subtraction; Lanes 7,8—PCR result for 1000 ng input *E. coli* total RNA plus subtraction; Lanes 9,10—PCR result for 2500 ng input *E. coli* total RNA plus subtraction; Lanes 11,12—PCR result for 5000 ng input *E. coli* total RNA plus subtraction; Lanes 13,14—PCR result for 500 ng input *E. coli* total RNA minus subtraction; and Lane 15—PCR result for no template control reaction. Panel 5A shows 5'-23S rRNA RT-PCR. Panel 5B shows 5'-16S rRNA RT-PCR. Panel 5C shows 5S rRNA RT-PCR. Panel 5D shows ompA mRNA RT-PCR.

FIG. 5, Lanes 1-12 show excellent reduction in the amount of 23S (Panel A), 16S (Panel B) and 5S (Panel C) rRNA sequences contained in the different inputs of E. coli total RNA in duplicate. Whereas, the ompA mRNA (Panel D) transcripts was still clearly detected in all samples and appeared to be unperturbed compared to the corresponding non-subtracted samples (Lanes 7 and 8 versus Lane 13 and 14). Clearly, this method for rRNA subtraction appears to be applicable across a broad range of total RNA inputs with at least a 100-fold dynamic range in this example.

Example 6

Subtraction of Fragmented E. coli 23S, 16S and 5S rRNA Sequences Using the E. coli Biotinylated Antisense rRNA Mixture Ten micrograms of E. coli total RNA was fragmented in 1× fragmentation buffer (Ambion) at 65° C. for 3 minutes. The fragmented RNA was purified using the ZYMO RNA Clean-up procedure, eluted in 200 RNase-free water and the concentration determined by measuring the absorbance at 260 nm with a spectrophotometer. A 300 ng aliquot of the fragmented RNA compared to the intact RNA was analyzed by ethidium bromide stained agarose gel electrophoresis as shown in FIG. 6A.

Figure 6A:
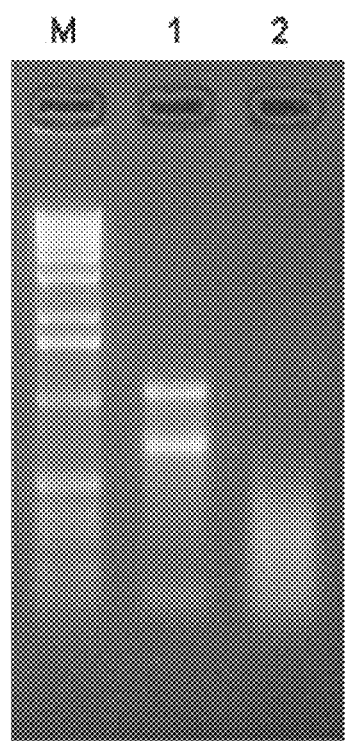
FIG. 6A shows the following: Lane M—DNA molecular weight ladder; Lane 1—300 ng intact *E. coli* total RNA; and Lane 2—300 ng fragmented *E. coli* total RNA.

FIG. 6A, Lane 1 shows the intact E. coli total RNA and Lane 2 shows the corresponding fragmented total RNA. The intact 23S and 16S rRNA bands were no longer visible in the fragmented sample contained in Lane 2.

Next, ribosomal RNA subtraction was applied to a 2.5 µg sample of the fragmented E. coli total RNA sample comparing it to a similar amount of intact E. coli total RNA. The following four reactions were assembled—reactions #1 and #2 contained 2.5 µg of intact E. coli total RNA each and reactions #3 and #4 contained 2.5 µg of the fragmented E. coli total RNA each. Next, to each of reactions #2 and #4, 8 µl of the E. coli biotinylated antisense rRNA mixture was added and the final reaction volume adjusted to 40 µl in 1× hybridization buffer. The reactions were incubated at 68° C. for 10 minutes and then at room temperature for 15 minutes. Each reaction was transferred to a fresh 1.5-ml microcentrifuge tube containing 50 µl of washed streptavidin microspheres. The reactions were further incubated at room temperature for 15 minutes with occasional gentle mixing (3-4 minutes) in order to allow for formation of the biotin-streptavidin complex. The reactions were spun at 12,000 rpm for 5 minutes on a benchtop centrifuge and each supernatant transferred to a fresh 1.5-ml microcentrifuge tube. The RNA contained in the supernatants were purified using the ZYMO RNA Clean-up procedure and eluted in 13.5 µl RNase-free water. Fifty percent of each purified sample was analyzed by ethidium bromide stained agarose gel electrophoresis and Northern blot analysis as shown in FIG. 6B.

Figure 6B:
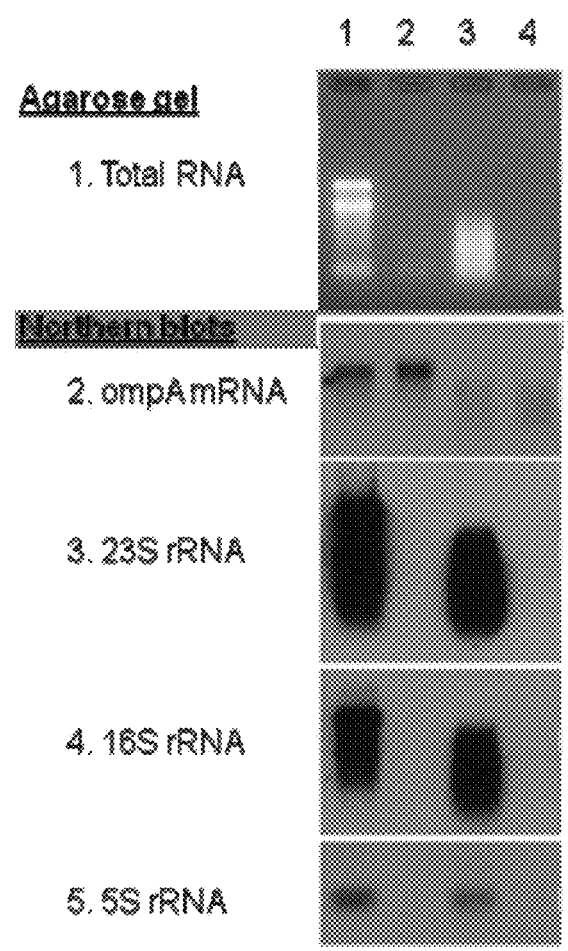
FIG. 6B shows the following: Lane M—DNA molecular weight ladder; Lane 1—Intact *E. coli* total RNA minus subtraction; Lane 2—Intact *E. coli* total RNA plus subtraction; Lane 3—Fragmented *E. coli* total RNA minus subtraction; and Lane 4—Fragmented *E. coli* total RNA plus subtraction. Panel 1 shows an ethidium bromide stained agarose gel. Panel 2 shows ompA mRNA Northern blot. Panel 3 shows 23S rRNA Northern blot. Panel 4 shows 16S rRNA Northern blot. Panel 5 shows 5S rRNA Northern blot.

FIG. 6B, Panel 1 (Lanes 2 and 4) show the RNA remaining following rRNA subtraction. In the case of the intact total RNA, it is clearly evident that the 23S and 16S rRNA bands are removed (Lane 2 versus Lane 1). Whereas, for the fragmented total RNA, there is an overall reduction in the amount of RNA following subtraction as would be expected if the fragments of rRNA were also subtracted (Lanes 4 versus Lane 3). The Northern blot analysis for ompA mRNA (Panel 2) and 23S (Panel 3), 16S (Panel 4) and 5S (Panel 5) rRNA clearly show similar and excellent subtraction of the different rRNA sequences in both the intact total RNA (Panel 3, 4, and 5—Lane 2) and fragmented total RNA (Panel 3, 4, and 5—Lane 4) compared to the respective non-subtracted samples (Panel 3, 4, and 5—Lane 1 and 3). At the same time, the amount of ompA mRNA sequence appears to be unperturbed by the subtraction process for both the intact total RNA (Panel 2—Lane 2 versus Lane 1) and the fragmented total RNA (Panel 2—Lane 4 versus Lane 3).

In addition, the remaining 50% of each purified RNA sample was converted to first-strand cDNA in a standard reverse transcriptase reaction containing random hexamers and purified using the Qiaquick PCR purification kit as recommended by the manufacturer (Qiagen). A 5-µl aliquot of each was then used in separate PCR amplification reactions containing primers specific to the terminal 5' regions of 23S (SEQ ID NO: 15 and SEQ ID NO: 16) and 16S rRNA (SEQ ID NO: 19 and SEQ ID NO: 20), the complete 5S rRNA (SEQ ID NO: 13 and SEQ ID NO: 23) and the ompA mRNA (SEQ ID NO: 24 and SEQ ID NO: 25) for 20 cycles. A 5-µl aliquot of each PCR reaction was analyzed by ethidium bromide stained agarose gel electrophoresis as shown in FIG. 6C.

Figure 6C:
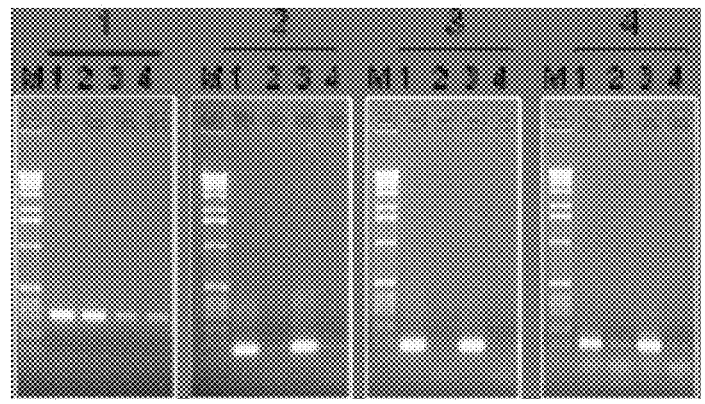
FIG. 6C shows the following: Lane M—DNA molecular weight ladder; Lane 1—Intact *E. coli* total RNA minus subtraction; Lane 2—Intact *E. coli* total RNA plus subtraction; Lane 3—Fragmented *E. coli* total RNA minus subtraction; and Lane 4—Fragmented *E. coli* total RNA plus subtraction. Panel 1 shows ompA RT-PCR. Panel 2 shows 23S rRNA 5' RT-PCR. Panel 3 shows 16S rRNA 5' RT-PCR. Panel 4 shows 5S rRNA RT-PCR.

FIG. 6C shows that by RT-PCR analysis, there was excellent subtraction of 23S (Panel 2), 16S (Panel 3) and 5S rRNA (Panel 4) for both the intact (Lane 2 versus Lane 1) and the fragmented (Lane 4 versus Lane 3) E. coli total RNA. Whereas, the ompA mRNA was equally preserved in both cases before and after subtraction (Panel 1).

Example 7

Specific Hybridization of Human, Mouse and Rat 28S and 18S rRNA to Human Biotinylated Antisense 28S and 18S rRNA, and their Removal with Streptavidin Microspheres

Intact total RNA (500 ng) samples for human (reactions #4 and #5), mouse (reactions #7 and #8) and rat (reactions #10 and #11) were mixed with either 2.1 µg of biotinylated antisense 28S rRNA or 1.0 µg of biotinylated antisense 18S rRNA in 1× hybridization buffer in a final volume of 20 µl. Corresponding intact total RNA samples (reactions #3, #6 and #9) and biotinylated antisense rRNA alone (#1 and #2) were included as controls. All reactions were incubated at 68° C. for 10 minutes followed by room temperature for 15 minutes. The RNA contained in each sample was then purified using the ZYMO RNA Clean-up procedure and eluted in 13.5 µl RNase-free water. The entire sample for each was analyzed by ethidium bromide stained agarose gel electrophoresis as shown in FIG. 7A.

Figure 7A:
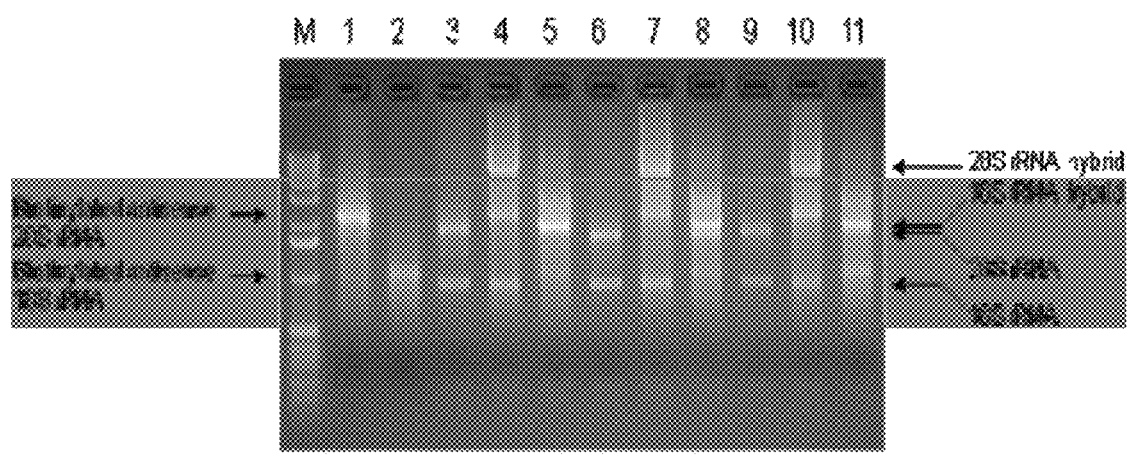
FIG. 7A shows the following: Lane M—DNA molecular weight ladder; Lane 1—biotinylated antisense 28S rRNA; Lane 2—biotinylated antisense 18S rRNA; Lane 3—Human total RNA; Lane 4—Human total RNA plus biotinylated antisense 28S rRNA; Lane 5—Human total RNA plus biotinylated antisense 18S rRNA; Lane 6—Mouse total RNA; Lane 7—Mouse total RNA plus biotinylated antisense 28S rRNA; Lane 8—Mouse total RNA plus biotinylated antisense 18S rRNA; Lane 9—Rat total RNA; Lane 10—Rat total RNA plus biotinylated antisense 28S rRNA; and Lane 11—Rat total RNA plus biotinylated antisense 18S rRNA.

FIG. 7A, Lanes 1 and 2 show the individual biotinylated antisense 23S and 18S rRNA, respectively. Lanes 3, 6 and 9 show the individual intact total RNA corresponding to human, mouse and rat, respectively. Lanes 4, 7 and 10 show the human, mouse and rat total RNA samples, respectively following hybridization to the biotinylated antisense 28S rRNA. Clearly, the 28S rRNA band in the different total RNA samples have hybridized to its complementary antisense rRNA since it now migrates with a high molecular weight higher whereas, the 18S rRNA remained unperturbed. When the different total RNA samples were then hybridized to the biotinylated antisense 18S rRNA, clearly the 18S rRNA band now migrated with a higher molecular weight (Lane 5, 8 and 11) and now, the 28S band was unperturbed. It's evident from these results that each biotinylated antisense rRNA was hybridizing specifically to its complementary target and equally well for human, mouse and rat that share at least 99% sequence homology.

Next, a biotinylated antisense rRNA mixture for human comprising approximately 1.2 pmoles each of 28S and 18S antisense rRNA in a final volume of 4 µl of RNase-free water was prepared using the in vitro synthesized RNA made as described in Example 1. Intact total RNA (2.5 µg) from human (HeLa), mouse (3T3) and rat (NRK) were each mixed with 8 µl of the biotinylated antisense rRNA solution in 1× hybridization buffer in a final volume of 40 µl. A control reaction containing only 2.5 µg of the corresponding intact total RNA was also included. The reactions were incubated at 68° C. for 10 minutes followed by room temperature for 15 minutes. Each reaction was transferred to a fresh 1.5-ml microcentrifuge tube containing 100 µl of washed streptavidin microspheres, respectively. The reactions were further incubated at room temperature for 15 minutes with occasional gentle mixing (3-4 minutes) in order to allow formation of the biotin-streptavidin complex and then 37° C. for 5 minutes. The reactions were spun at 14,000 rpm for 5 minutes on a benchtop centrifuge and each supernatant transferred to a fresh 1.5-ml microcentrifuge tube. The RNA contained in the supernatants were purified using the ZYMO RNA Clean-up procedure and eluted in 13.5 µl RNase-free water. Fifty percent of each purified RNA sample was analyzed by ethidium bromide stained agarose gel electrophoresis as shown in FIG. 7B.

Figure 7B:
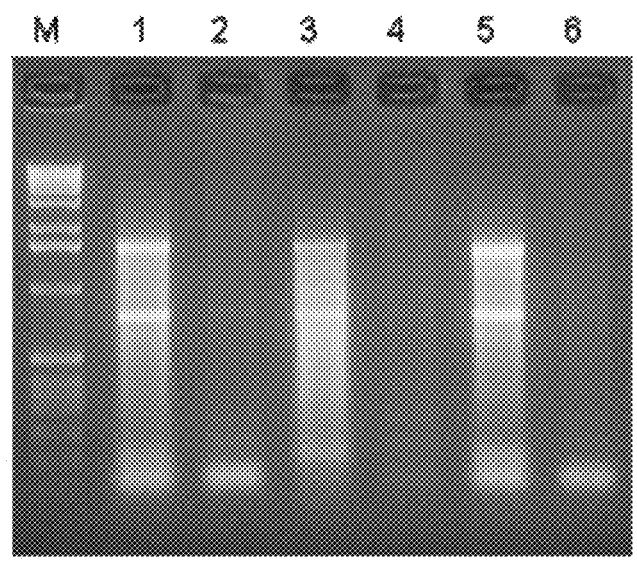
FIG. 7B shows the following: Lane M—DNA molecular weight ladder; Lane 1—Human total RNA (HeLa) minus subtraction; Lane 2—Human total RNA (HeLa) plus subtraction; Lane 3—Mouse total RNA (3T3) minus subtraction; Lane 4—Mouse total RNA (3T3) plus subtraction; Lane 5—Rat total RNA (NRK) minus subtraction; and Lane 6—Rat total RNA (NRK) plus subtraction.

FIG. 7B, Lanes 1, 3 and 5 show the individual total RNA without any 28S and 18S rRNA subtraction, whereas, Lanes 2, 4, and 6 show the corresponding RNA remaining following 28S and 18S rRNA subtraction. It is clear from these results that a majority of the 28S and 18S rRNA bands were removed following the subtraction procedure as described.

Example 8

Subtraction of 28S, 18S, 5.8S and 5S rRNA from Varying Amounts of Intact Human Total RNA Using a Human Biotinylated Antisense rRNA Mixture

A biotinylated antisense rRNA mixture for human comprising approximately 1.2 pmoles each of 28S, 18S, 5.8S and 5S antisense rRNA in a final volume of 4 µl of RNase-free water was prepared using the in vitro synthesized RNA made as described in Example 1. Ribosomal RNA subtraction reactions comprising 100 ng (reaction #1), 500 ng (reaction #2) and 5.0 µg (reaction #3) of intact HeLa total RNA with 2 µl, 4 µl and 8 µl of the biotinylated human antisense rRNA mixture, respectively were prepared in 1× hybridization buffer in a final volume of 20 µl. A control reaction (reaction #4) with only 500 ng of the intact HeLa total RNA was also included. The reactions were incubated at 68° C. for 10 minutes followed by room temperature for 15 minutes. Each reaction was transferred to a fresh 1.5-ml microcentrifuge tube containing 25 µl, 50 µl, 125 µl and 50 µl of washed streptavidin microspheres, respectively. The reactions were further incubated at room temperature for 15 minutes with occasional gentle mixing (3-4 minutes) in order to allow formation of the biotin-streptavidin complex and then 37° C. for 5 minutes. The reactions were spun at 14,000 rpm for 5 minutes on a benchtop centrifuge and each supernatant transferred to a fresh 1.5-ml microcentrifuge tube. The RNA contained in the supernatants were purified using the ZYMO RNA Clean-up procedure and eluted in 13.5 µl RNase-free water. Next, each purified RNA sample was converted to first-strand cDNA in a standard reverse transcriptase reaction containing random hexamers and purified using the Qiaquick PCR purification kit as recommended by the manufacturer (Qiagen). A 5-µl aliquot of each was then used in separate PCR amplification reactions containing primers specific to the terminal 5' and 3' regions of 28S (SEQ ID NO: 26: 5'-CTCAGTAACGGCGAGT-GAAC, SEQ ID NO: 27: 5'-GCCTCGATCA-GAAGGACTTG, SEQ ID NO: 28: 5'-TACCACAGGGA TAACTGGCT and SEQ ID NO: 29: 5'-TAGGAAGAGC-CGACATCGAA) and 18S rRNA (SEQ ID NO: 30: 5'-CCTACCTGGTTGATCCTGCC, SEQ ID NO: 31: 5'-CCAAGTAGGAGAGGAGCGAG, SEQ. ID. No. 32: 5'-CCCAGTAAGTGC GGGTCATA and SEQ ID NO: 33: 5'-TCACTAAACCATCCAATCGGTAGTA) the complete 5.8S rRNA (SEQ ID NO: 3 and SEQ ID NO: 34: 5'-GATC-CTTCCGCAGGT TCACCTAC), the complete 5S rRNA (SEQ ID NO: 5 and SEQ ID NO: 35: 5'-AAGCCTACAG-CACCCGGTATTC) and 5' GAPDH mRNA (SEQ ID NO: 36: 5'-TCGACAGTCAGCCGCATCTTCTTT and SEQ ID NO: 37: 5'-ACCAAATCCGTTG ACTCCGACCTT) for 20 cycles. A control reaction for each primer pair minus template was included. A 5-µl aliquot of each PCR reaction was analyzed by ethidium bromide stained agarose gel electrophoresis shown in FIG. 8.

Figure 8:
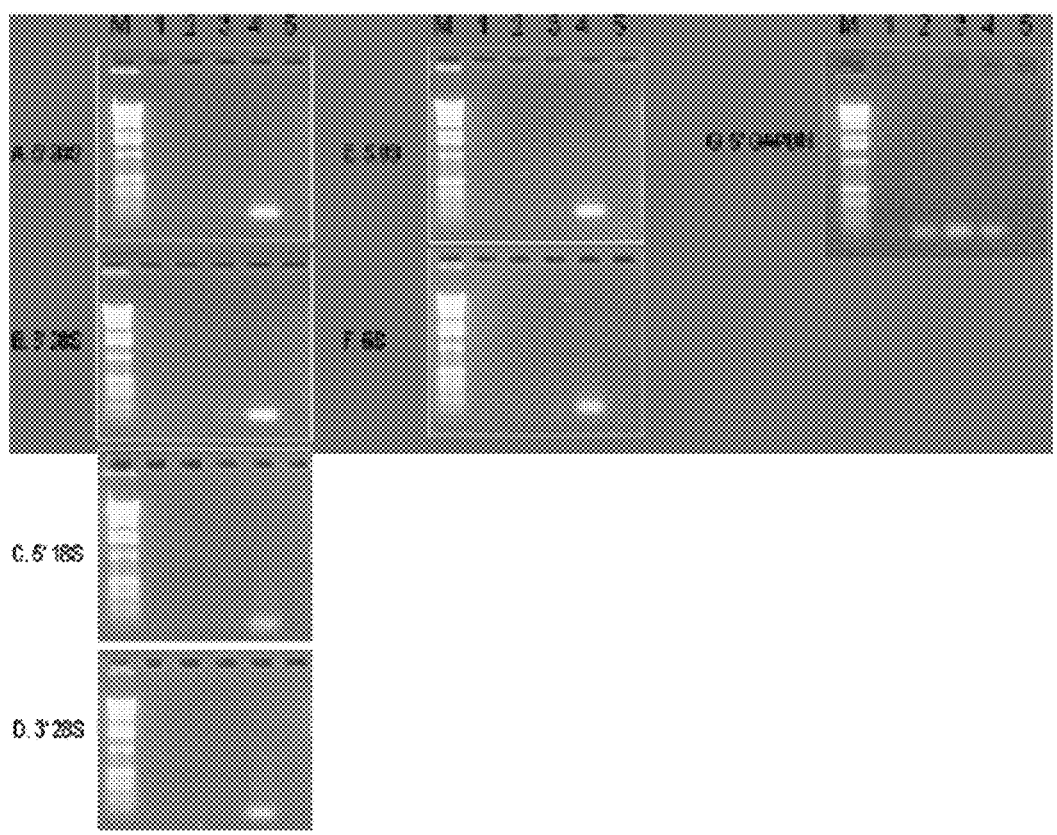
FIG. 8 shows the following: Lane M—DNA molecular weight ladder; Lane 1—PCR result for 100 ng input human total RNA plus subtraction; Lane 2—PCR result for 500 ng input human total RNA plus subtraction; Lane 3—PCR result for 5.0 μg input human total RNA plus subtraction; Lane 4—PCR result for 500 ng input human total RNA minus subtraction; and Lane 5—PCR result for no template control reaction. Panel A shows 5' 28S rRNA RT-PCR. Panel B shows 3' 28S rRNA RT-PCR. Panel C shows 5' 18S rRNA RT-PCR. Panel D shows 3' 18S rRNA RT-PCR. Panel E shows 5.8S rRNA RT-PCR. Panel F shows 5S rRNA RT-PCR. Panel G shows 5' GAPDH mRNA RT-PCR.

FIG. 8, Lanes 1, 2 and 3 show the RT-PCR results for 28S rRNA (Panel A), 18S rRNA (Panel B), 5.8S rRNA (Panel C), 5S rRNA (Panel D) and GAPDH mRNA (Panel E) for the 100 ng, 500 ng and 5.0 µg inputs of total RNA subtracted with the biotinylated human antisense rRNA mixture, respectively. Lane 4 shows the PCR for the 500 ng non-subtracted total RNA input. It is evident from the results that there is excellent subtraction over a broad range of total RNA inputs for the different ribosomal RNA sequences using the biotinylated antisense rRNA mixture (Lanes 1, 2 and 3 versus Lane 4).

Example 9

Subtraction of Human rRNA Sequences Exhibited by Various Levels of Fragmented Human Total RNA HeLa intact total RNA was fragmented in 1× fragmentation buffer (Ambion) for 1, 2 and 3 minutes. The RNA samples were purified using the ZYMO RNA Clean-up procedure, eluted RNase-free water and the concentration determined at an absorbance of 260 nm using a spectrophotometer.

Duplicate reactions comprising either 2.5 µg of the intact (reactions # and #2) or fragmented (reactions #3, #4, #5, #6, #7 and #8) total RNA samples were prepared in 1× hybridization buffer. To one of each duplicate reaction (#2, #4, #6 and #8), 8 µl of the biotinylated human antisense rRNA mixture was added and the final volume for each reaction adjusted to 40 µl. The reactions were incubated at 68° C. for 10 minutes followed by room temperature for 15 minutes. Each reaction was transferred to a fresh 1.5-ml microcentrifuge tube containing 100 µl of washed streptavidin microspheres. The reactions were further incubated at room temperature for 15 minutes with occasional gentle mixing (3-4 minutes) in order to allow formation of the biotin-streptavidin complex and then 37° C. for 5 minutes. The reactions were spun at 14,000 rpm for 5 minutes on a benchtop centrifuge and each supernatant transferred to a fresh 1.5-ml microcentrifuge tube. The RNA contained in the supernatants were purified using the ZYMO RNA Clean-up procedure and eluted in 13.5 µl RNase-free water. Fifty percent of each purified RNA sample was analyzed by ethidium bromide stained gel electrophoresis as shown in FIG. 9A.

Figure 9A:
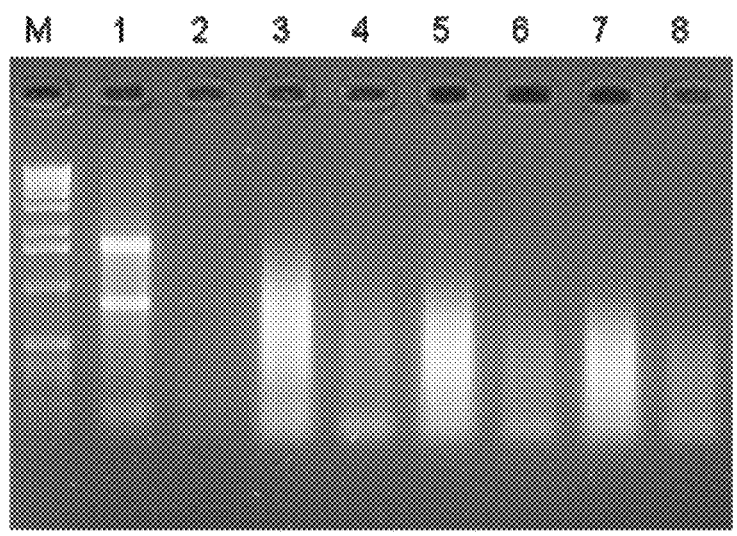
FIG. 9A shows the following: Lane M—DNA molecular weight ladder; Lane 1—Intact Hela total RNA minus subtraction; Lane 2—Intact HeLa total RNA plus subtraction; Lane 3—Fragmented (1 minute) Hela total RNA minus subtraction; Lane 4—Fragmented (1 minute) Hela total RNA plus subtraction; Lane 5—Fragmented (2 minute) Hela total RNA minus subtraction; Lane 6—Fragmented (2 minute) Hela total RNA plus subtraction; Lane 7—Fragmented (3 minute) Hela total RNA minus subtraction; and Lane 8—Fragmented (3 minute) Hela total RNA plus subtraction.

FIG. 9A, Lanes 4, 6 and 8, containing the fragmented total RNA and biotinylated antisense rRNA show a significant reduction in the amount of RNA as a result of subtraction compared to the respective controls (Lanes 3, 5 and 7). In Lane 2 compared to Lane 1 with the intact total RNA, the full-length rRNA bands were no longer visible.

Next, the remaining 50% of each purified RNA sample was converted to first-strand cDNA in a standard reverse transcriptase reaction containing random hexamers and purified using the Qiaquick PCR purification kit as recommended by the manufacturer (Qiagen). A 5-µl aliquot of each was then used in separate PCR amplification reactions containing primers specific to the terminal 5' regions of 28S (SEQ ID NO: 26 and SEQ ID NO: 27) and 18S rRNA (SEQ ID NO: 30 and SEQ ID NO: 31), the complete 5.8S rRNA (SEQ ID NO: 3 and SEQ ID NO: 34), the complete 5S rRNA (SEQ ID NO: 5 and SEQ ID NO: 35) and 5' GAPDH mRNA (SEQ ID NO: 36 and SEQ ID NO: 37) for 20 cycles. A control reaction minus template was also performed for each primer pair. A 5-µl aliquot of each PCR reaction was analyzed by ethidium bromide stained agarose gel electrophoresis shown in FIG. 9B.

Figure 9B:
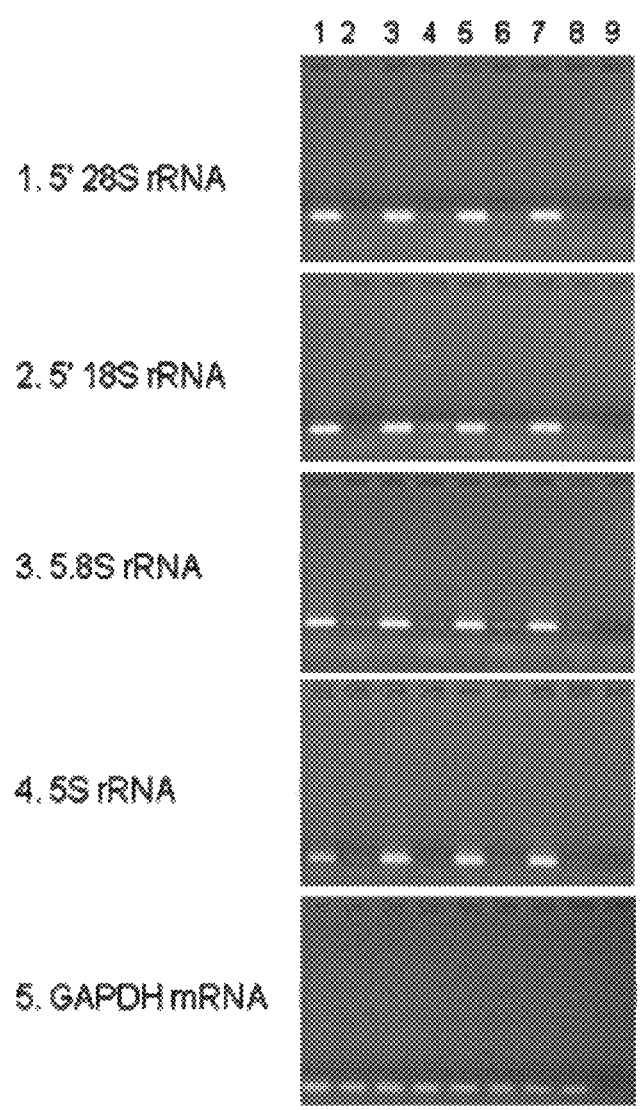
FIG. 9B shows the following: Lane 1—PCR result for intact HeLa total RNA minus subtraction; Lane 2—PCR result for intact HeLa total RNA plus subtraction; Lane 3—PCR result for fragmented (1 minute) HeLa total RNA minus subtraction; Lane 4—PCR result for fragmented (1 minute) HeLa total RNA plus subtraction; Lane 5—PCR result for fragmented (2 minute) HeLa total RNA minus subtraction; Lane 6—PCR result for fragmented (2 minute) HeLa total RNA plus subtraction; Lane 7—PCR result for fragmented (3 minute) HeLa total RNA minus subtraction; Lane 8—PCR result for fragmented (3 minute) HeLa total RNA plus subtraction; and Lane 9—PCR result for no template control reaction. Panel 1 shows 5' 28S rRNA. Panel 2 shows 5' 18S rRNA. Panel 3 shows 5.8S rRNA. Panel 4 shows 5S rRNA. Panel 5 shows 5' GAPDH mRNA

FIG. 9B, Lanes 2, 4, 6 and 8 show the PCR results for 28S rRNA (Panel 1), 18S rRNA (Panel 2), 5.8S rRNA (Panel 3), 5S rRNA (Panel 4) and GAPDH mRNA (Panel 5) for the intact, and fragmented (1, 2 and 3 minutes) total RNA, respectively following subtraction. The corresponding non-subtracted control reactions are shown in Lanes 1, 3, 5 and 7. It is evident from the results that there is excellent subtraction over a broad range of fragmented total RNA inputs similar to the intact total RNA for the different ribosomal RNA sequences using the biotinylated antisense rRNA mixture.

Example 10

Comparison of E. coli rRNA Subtraction Using the Method of the Present Invention and the MICROBExpress™ Method A kit that uses conserved rRNA (23S and 16S) oligonucleotide sequences to subtract the corresponding rRNA from inputs of 2 µg-10 µg from prokaryotic total RNA was purchased from Ambion for comparison to the exemplary methods in these Examples. An 15 µg aliquot of the intact control E. coli total RNA supplied in the MICROBExpress™ kit was first fragmented in 1× fragmentation buffer (Ambion) at 65° C. for 2 minutes, purified using the ZYMO RNA Clean-up procedure, eluted RNase-free water and the concentration determined at an absorbance of 260 nm using a spectrophotometer. An equal aliquot (2.5 µg) of either the intact or fragmented E. coli total RNA was then used in subtraction reactions following either the exemplary method described in Example 9 ("Exemplary Method") for the appropriate RNA samples or the MICROBExpress™ method exactly as described by the manufacturer (Ambion). Control reactions representing no rRNA subtraction were included for both methods. Each RNA sample was then purified by EtOH precipitation as described for the MICROBExpress™ procedure and resuspended in 12 µl RNase-free water. Fifty percent of each purified RNA sample was analyzed by ethidium bromide stained agarose gel electrophoresis and Northern blot as shown in FIG. 10A.

Figure 10A:
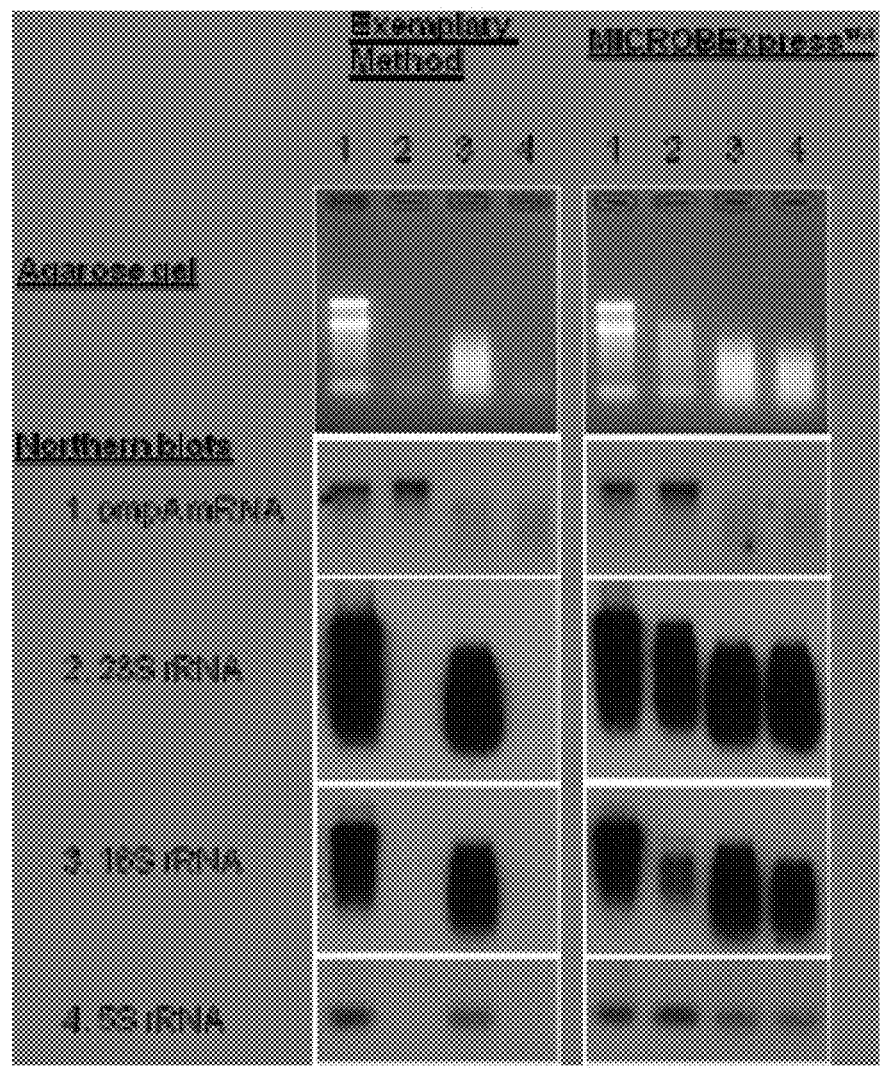
FIG. 10A shows the following: Lane M—DNA molecular weight ladder; Lane 1—Intact E. coli total RNA minus subtraction; Lane 2—Intact E. coli total RNA plus subtraction; Lane 3—Fragmented E. coli total RNA minus subtraction; and Lane 4—Fragmented E. coli total RNA plus subtraction. Panel 1 shows ompA mRNA. Panel 2 shows 23S rRNA. Panel 3 shows 16S rRNA. Panel 4 shows 5S rRNA.

FIG. 10A, Lanes 1, 2 and 3, 4 show the relative rRNA subtraction from intact and fragmented total RNA using the Exemplary Method and the MICROBExpress™ method for 23S rRNA (Panel 2), 16S rRNA (Panel 3) and 5S rRNA (Panel 4). Clearly, for both the intact and fragmented total RNA samples, the different rRNA sequences were subtracted significantly better using the Exemplary Method invention (Exemplary Method—Lanes 2 and 4) compared to the MICROBExpress method (MICROBExpress™ Panel—Lanes 2 and 4). It appears that even the control intact RNA supplied with the MICROBExpress™ contain a level of fragmented rRNA sequences that were clearly not removed by the MicrobExpress method (MICROBExpress™ Panel—Lane 2) but were clearly removed using the Exemplary Method described herein (Exemplary Method, Panel—Lane 2). In addition, Panel 1 shows that the ompA mRNA sequence remain unperturbed before and after subtraction for both methods.

Next, the remaining 50% of each purified RNA sample was converted to first-strand cDNA in a standard reverse transcriptase reaction containing random hexamers and purified using the Qiaquick PCR purification kit as recommended by the manufacturer (Qiagen). A 5-µl aliquot of each was then used in separate PCR amplification reactions containing primers specific to the terminal 5' region of 23S (SEQ ID NO: 15 and SEQ ID NO: 16) and 16S rRNA (SEQ ID NO: 19 and SEQ ID NO: 20) the complete 5S rRNA (SEQ ID NO: 13 and SEQ ID NO: 23) and ompA mRNA (SEQ ID NO: 24 and SEQ ID NO: 25) for 20 cycles. A 5-µl aliquot of each PCR reaction was analyzed by ethidium bromide stained agarose gel electrophoresis shown in FIG. 10B.

Figure 10B:
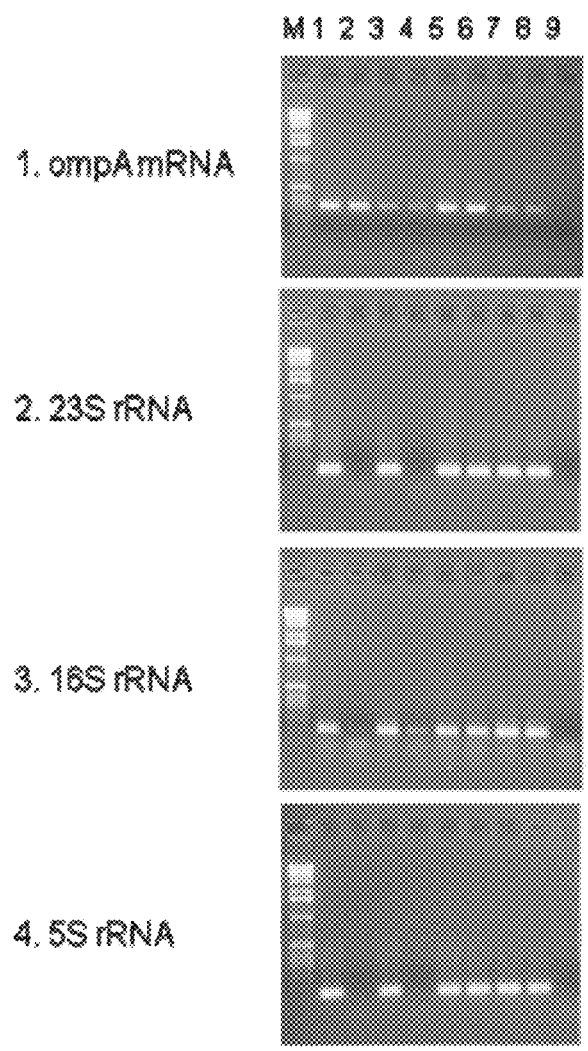
FIG. 10B shows the following: Lane M—DNA molecular weight ladder; Lane 1—PCR result for intact E. coli total RNA minus subtraction; Lane 2—PCR result for intact E. coli total RNA plus subtraction; Lane 3—PCR result for fragmented E. coli total RNA minus subtraction; and Lane 4—PCR result for fragmented E. coli total RNA plus subtraction. Panel 1 shows ompA mRNA. Panel 2 shows 23S rRNA. Panel 3 shows 16S rRNA. Panel 4 shows 5S rRNA.

FIG. 10B, Lanes 2 and 4 show the PCR results for 23S rRNA (Panel 2), 16S rRNA (Panel 3), 5S rRNA (Panel 4) and ompA mRNA (Panel 1) for the intact and fragmented *E. coli* total RNA, respectively following subtraction using the Exemplar Method and the MICROBExpress™ method. The corresponding non-subtracted control reactions are shown in Lanes 1 and 3. It is evident from the results that there is excellent subtraction of the different rRNA sequences exhibited by both the intact and fragmented total RNA samples using the Exemplary Method (Exemplary Method Panel) compared to the MICROBExpress™ method (MicroExpress Panel). In both cases though, the ompA mRNA was similarly maintained.

Example 11

Comparison of Human rRNA Subtraction Using an Exemplary Method Vs. The OLIGOTEX Poly A+ mRNA Purification Method A kit that uses oligonucleotide dT to isolate mRNA from eukaryotic total RNA was purchased from Qiagen for comparison to the Exemplary Method described in Example 9 above. When fragmented RNA was used, the RNA was first fragmented in 1× fragmentation buffer (Ambion) at 65° C. for 2 minutes. The intact or fragmented RNA was purified using the ZYMO RNA Clean-up procedure, eluted RNase-free water and the concentration determined at an absorbance of 260 nm using a spectrophotometer. An equal aliquot (2.5 µg) of either the intact or fragmented *E. coli* total RNA was then used in rRNA subtraction reactions using the Exemplary Method for the appropriate RNA samples or the Oligotex poly A+ mRNA purification method exactly as described by the manufacturer (Qiagen). Control reactions representing no rRNA subtraction were included for both methods. Each RNA sample was then purified by ethanol precipitation and resuspended in 12 µl RNase-free water. Fifty percent of each purified RNA sample was analyzed by ethidium bromide stained agarose gel electrophoresis as shown in FIG. 11A.

Figure 11A:
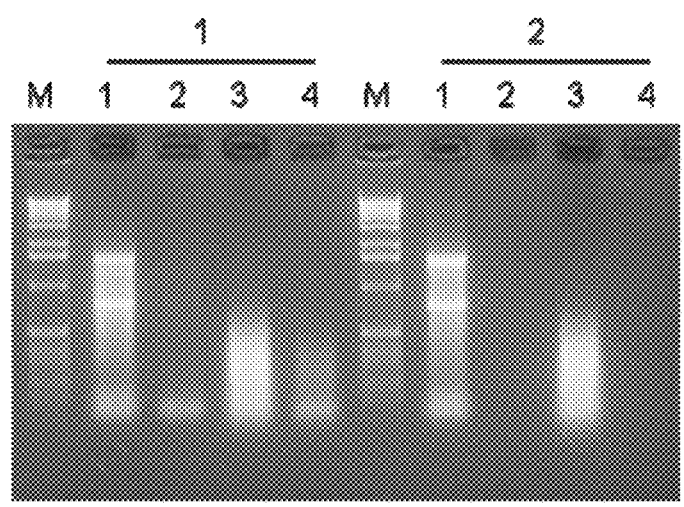
FIG. 11A shows the following: Lane M—DNA molecular weight ladder; Lane 1—Intact HeLa total RNA minus subtraction; Lane 2—Intact HeLa total RNA plus subtraction; Lane 3—Fragmented HeLa total RNA minus subtraction; and Lane 4—Fragmented HeLa total RNA plus subtraction. Panel 1 shows results of an exemplary method of the present invention. Panel 2 shows the results of the OLIGOTEX method.

FIG. 11A, Lanes 1, 2 and 3, 4 show the relative rRNA removal for intact and fragmented total RNA using the Exemplary Method and the OLIGOTEX poly A+ mRNA purification method. Clearly, for both the intact and fragmented total RNA samples, the different rRNA sequences were visibly removed using the Exemplary Method (Panel 1—Lanes 2 and 4) and the OLIGOTEX method (Panel 2—Lanes 2 and 4) compared to the respective controls (Panel 1—Lanes 1 and 3 and Panel 2—Lanes 1 and 3). In addition, it appears that there was very little mRNA visibly remaining following the OLIGOTEX method and all of the types of small RNA molecules (tRNA, miRNA etc.) appear to have been eliminated as well (Panel 2—Lanes 2 and 4).

Next, the remaining 50% of each purified RNA sample was converted to first-strand cDNA in a standard reverse transcriptase reaction containing random hexamers and purified using the Qiaquick PCR purification kit as recommended by the manufacturer (Qiagen). A 5-µl aliquot of each was then used in separate PCR amplification reactions containing primers specific to the terminal 5' and 3' regions of 28S (SEQ ID NO: 26, SEQ ID NO: 27, SEQ ID NO: 28 and SEQ ID NO: 29) and 18S rRNA (SEQ SEQ ID NO: 30, SEQ ID NO: 31, SEQ ID NO: 32 and SEQ ID NO: 33), the complete 5.8S rRNA (SEQ ID NO: 3 and SEQ ID NO: 34) and the complete 5S rRNA (SEQ ID NO: 5 and SEQ ID NO: 35) for 20 cycles. A 5-µl aliquot of each PCR reaction was analyzed by ethidium bromide stained agarose gel electrophoresis shown in FIG. 11B.

Figure 11B:
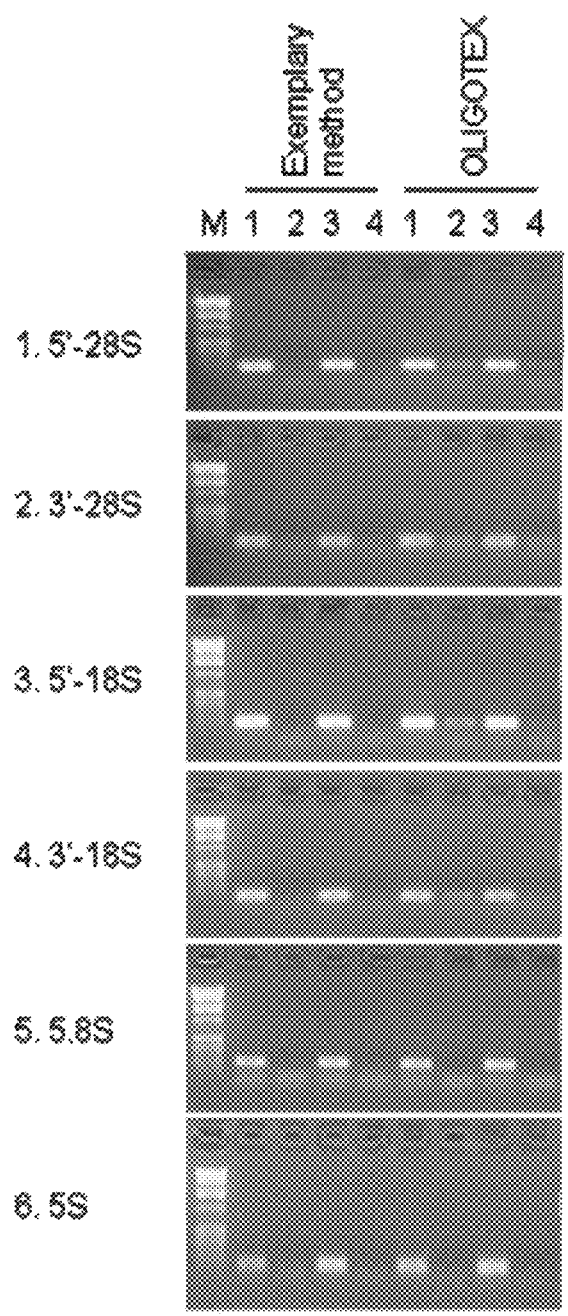
FIG. 11B shows the following: Lane M—DNA molecular weight ladder; Lane 1—PCR results for intact HeLa total RNA minus subtraction; Lane 2—PCR results for intact HeLa total RNA plus subtraction; Lane 3—PCR results for fragmented HeLa total RNA minus subtraction; and Lane 4—PCR results for fragmented HeLa total RNA plus subtraction. Panel 1 shows 5'-28S rRNA. Panel 2 shows 3'-28S rRNA. Panel 3 shows 5'-18S rRNA. Panel 4 shows 3'-18S rRNA. Panel 5 shows 5.8S rRNA. Panel 6 shows 5S rRNA.

FIG. 11B, Lanes 2 and 4 show the PCR results for 28S rRNA (Panels 1 and 2), 18S rRNA (Panel 3 and 4), 5.8S rRNA (Panel 5) and 5S rRNA (Panel 6) for the intact and fragmented HeLa total RNA, respectively following rRNA subtraction using the Exemplary Method and the OLIGOTEX method. The corresponding non-subtracted control reactions are shown in Lanes 1 and 3. It is evident from the results that there is overall excellent subtraction of the different rRNA sequences exhibited by both the intact and fragmented total RNA samples using the Exemplary Method (Exemplary Method Panel) and to the OLIGOTEX method (OLIGOTEX Panel). In fact, the Exemplary Method appears to be somewhat better than the OLIGOTEX method for both the 28S and 18S rRNA sequences (Panels 1-4) whereas, for the 5.8S and 5S rRNA sequences, the OLIGOTEX method appears to be slightly better (Panel E and F, respectively).

Figure 11C:
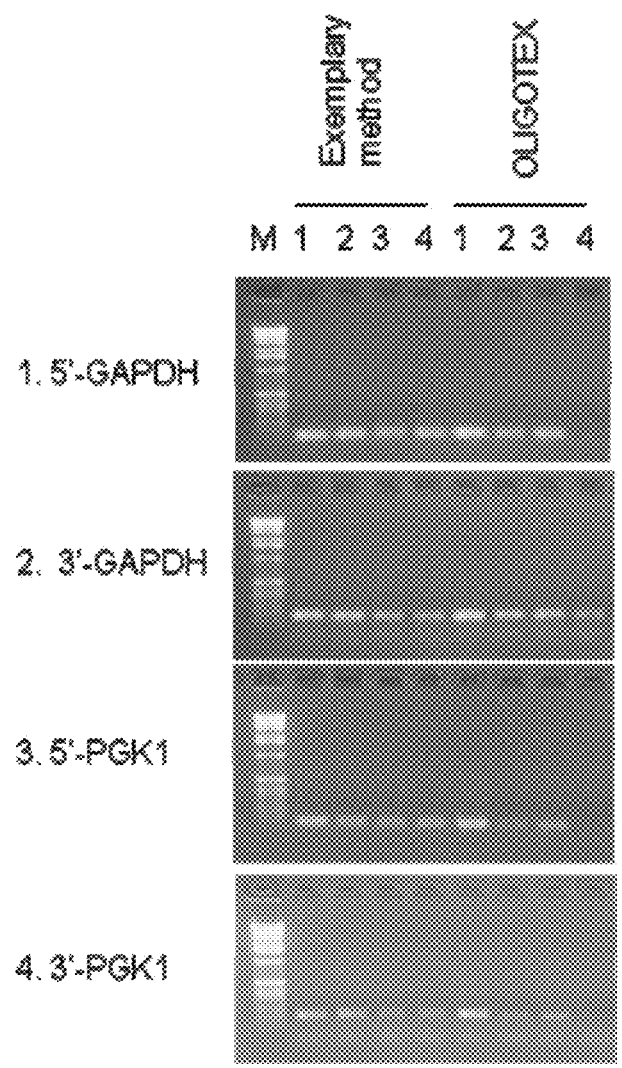
FIG. 11C shows the following: Lane M—DNA molecular weight ladder; Lane 1—PCR results for intact HeLa total RNA minus subtraction; Lane 2—PCR results for intact HeLa total RNA plus subtraction; Lane 3—PCR results for fragmented HeLa total RNA minus subtraction; and Lane 4—PCR results for fragmented HeLa total RNA plus subtraction. Panel 1 shows 5'-GAPDH. Panel 2 shows 3'-GAPDH. Panel 3 shows 5'-PGK1. Panel 4 shows 3'-PGK1.

In addition, PCR primers specific for the terminal 5' and 3' regions of GAPDH (SEQ ID NO: 36, SEQ ID NO: 37, SEQ ID NO: 38: 5'-CACAAGAGGAAGAGAGAGA CCCTCA and SEQ ID NO: 39: 5'-TTGATGGTACAT-GACAAGGTGCGG) and PGK1 (SEQ ID NO: 40: 5'-GAATCACCGACCTCTCTCCC, SEQ. ID. No. 41: 5'-CGACTCTCATAACGACCCGC, SEQ ID NO: 42: 5'-CCAGAGGTGACCACTTTCAA and SEQ ID NO: 43: 5'-ATGTGGAACAGAGCCTTCCTC) mRNA were used in PCR (GAPDH: 22 cycles and PGK1: 26 cycles) with the random primed cDNA templates and a 5-µl aliquot of each PCR reaction was analyzed by ethidium bromide stained agarose gel electrophoresis as shown in FIG. 11C. It is clearly evident from the PCR results that there is a reduction in the amount of mRNA for both GAPDH (Panels 1 and 2) and PGK 1 (Panels 3 and 4) in the OLIGOTEX method for both intact and fragmented total RNA (OLIGOTEX Panel, Lanes 2 and 4, respectively) compared to the non-rRNA-subtracted samples (OLIGOTEX Panel, Lanes 1 and 3, respectively), using the Exemplary Method (Exemplary Method Panel, Lanes 2 and 4). Furthermore, the Exemplary Method did not show any significant loss in the same mRNA sequences for both intact and fragmented total RNA (Exemplary Method Panel, Lanes 2 and 4, respectively) compared to the non-rRNA subtracted samples (Exemplary Method Panel, Lanes 1 and 3, respectively). In addition, the 5' regions of both GAPDH (Panel 1, Lane 4) and PGK1 (Panel 3, Lane 4) for the fragmented total RNA sample were lost with the OLIGOTEX method (OLigotex Panel) since the poly A tail was no longer present but not so for the Exemplary Method (Exemplary Method Panel, Lane 4 (Panel 1 and 3), respectively). Overall, these results demonstrate a clear benefit of the Exemplary Method compared to the OLIGOTEX method.

Figure 11D:
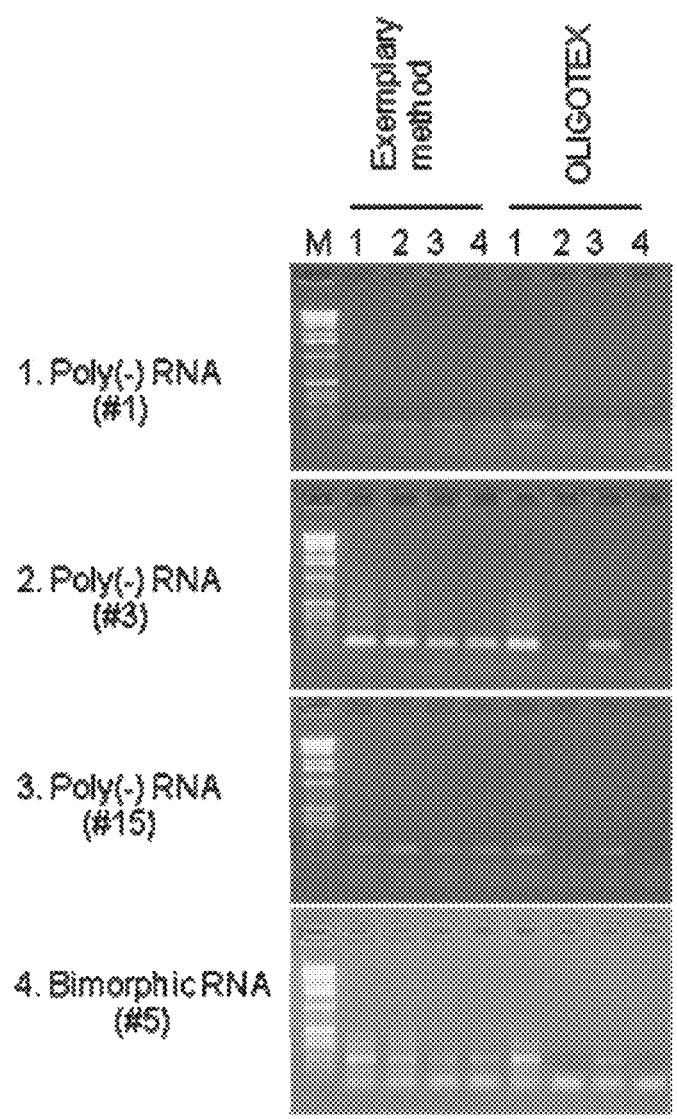
FIG. 11D shows the following: Lane M—DNA molecular weight ladder; Lane 1—PCR results for intact HeLa total RNA minus subtraction; Lane 2—PCR results for intact HeLa total RNA plus subtraction; Lane 3—PCR results for fragmented HeLa total RNA minus subtraction; and Lane 4—PCR results for fragmented HeLa total RNA plus subtraction. Panel 1 shows Poly A-RNA #1. Panel 2 shows Poly A-RNA #3. Panel 3 shows Poly A-RNA #15. Panel 4 shows Bimorphic RNA #5.

Next, PCR primers specific for Poly A- and bimorphic transcripts (SEQ ID NO: 44: 5'-CACGTTTTCTCAGCT-GCTTG and SEQ ID NO: 45: 5'-TTCACCTTTTCATC CAAGGC for transcript #1, SEQ ID NO: 46: 5'-GTGTG-GTGGTGTGTGCCTAT and SEQ ID NO: 47: 5'-GAGA-CATGGTCTTGCTCCGT for transcript #3, SEQ ID NO: 48: 5'-TAGCTCAGTGGTAGAGCGCA and SEQ ID NO: 49: 5'-GATTTGCTCAGCA GCACGTA for transcript #15 and SEQ ID NO: 50: 5'-CACTTGGGGACACTTTCCAG and SEQ ID NO: 51: 5'-TCAGGGAAAATGAGCCAATC for bimorphic transcript #5 (Poly A-Transcripts Expressed in HeLa Cells Qingfa Wu et. al. (July 2008). PLoS One (www followed by "plosone.org/article/info:doi/10.1371/journal. pone.0002803")) were used in PCR with the random primed cDNA templates (36, 22, 28 and 38 cycles, respectively) and a 5-µl aliquot of each PCR reaction was analyzed by ethidium bromide stained agarose gel electrophoresis as shown in FIG. 11D. It is clearly evident from the PCR results that the poly A- and biomorphic transcripts were no longer present following the OLIGOTEX mRNA purification method for both intact and fragmented total RNA (OLIGO-TEX Panel, Lanes 2 and 4, respectively) whereas, these sequences were maintained following rRNA subtraction using the Exemplary Method for both intact and fragmented total RNA (Exemplary Method PANEL, Lane 2 and 4, respectively). These results point to another clear benefit of the rRNA subtraction methods described in this application for maintaining a broader spectrum of transcripts allowing for better representation of the cellular content.

Example 12

Comparison of Human rRNA Subtraction Using an Exemplary Method of the Present Invention Vs. The RiboMinus™ Eukaryote Kit for RNA-Seq A kit (RiboMinus™ Eukaryote Kit for RNA-Seq) that uses two conserved oligonucleotide sequences for each of 28S, 18S, 5.8S and 5S rRNA to subtract the corresponding rRNA from inputs of 2 µg-10 µg from eukaryotic total RNA was purchased from InVitrogen (Burlington, ON) for comparison to an examplary method of the present invention. When fragmented total RNA was used, the initial total RNA was first fragmented in 1× fragmentation buffer (Ambion, Austin, Tex.) at 65° C. for 2 minutes. The intact or fragmented total RNA was purified using the ZYMO RNA Clean-up procedure, eluted RNase-free water and the concentration determined at an absorbance of 260 nm using a spectrophotometer. An equal aliquot (2.5 µg) of either the intact or fragmented HeLa total RNA was then used in rRNA subtraction reactions using the Exemplary Method for the appropriate RNA samples or the RiboMinus™ Eukaryote Kit for RNA-Seq method exactly as described by the manufacturer (InVitrogen). Control reactions representing no rRNA subtraction were included for both methods. Each RNA sample was then purified by ethanol precipitation and resuspended in 12 µl RNase-free water. Fifty percent of each purified RNA sample was analyzed by ethidium bromide stained agarose gel electrophoresis as shown in FIG. 12A.

Figure 12A:
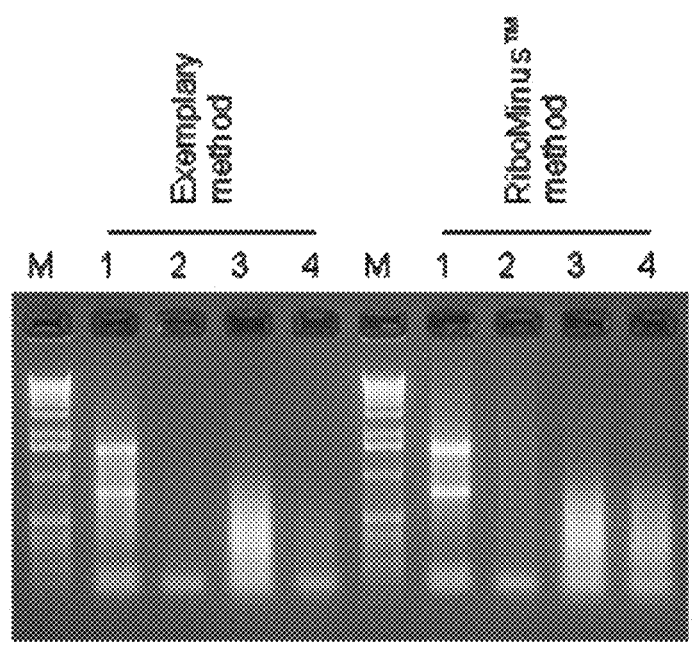
FIG. 12A shows the following: Lane M—DNA molecular weight ladder; Lane 1—Intact HeLa total RNA minus subtraction; Lane 2—Intact HeLa total RNA plus subtraction; Lane 3—Fragmented HeLa total RNA minus subtraction; and Lane 4—Fragmented HeLa total RNA plus subtraction.

FIG. 12A, Lanes 1, 2 and 3, 4 show the relative rRNA removal for intact and fragmented total RNA using the Exemplary Method and the RiboMinus™ Eukaryote Kit for RNA-Seq method. Clearly, for both the intact and fragmented total RNA samples, the different rRNA sequences were visibly removed using the Exemplary Method (Exemplary method—Lanes 2 and 4) whereas for the RiboMinus™ Eukaryote Kit for RNA-Seq method, only the intact total RNA showed reduction of the rRNA sequences (RiboMinus™ method—Lanes 2) compared to the respective non-rRNA-subtracted samples (Exemplary method—Lanes 1 and 3 and RiboMinus™ method—Lane 1). There appeared to be only minimal reduction of the rRNA-subtracted fragmented total RNA sample using the RiboMinus™ Eukaryote Kit for RNA-Seq as judged by the ethidium bromide stained intensity (RiboMinus™ method—Lane 4) compared to the non-rRNA-subtracted sample (RiboMinus™ method—Lane 3) likely due to the fact that those ribosomal fragments that are not represented by the consensus oligonucleotide sequences in the kit would therefore not be removed.

Next, the remaining 50% of each purified RNA sample was converted to first-strand cDNA in a standard reverse transcriptase reaction containing random hexamers and purified using the Qiaquick PCR purification kit as recommended by the manufacturer (Qiagen). A 5-µl aliquot of each was then used in separate PCR amplification reactions containing primers specific to the terminal 5' and 3' regions of 28S (SEQ ID NO: 26, SEQ ID NO: 27, SEQ ID NO: 28 and SEQ ID NO: 29) and 18S rRNA (SEQ SEQ ID NO: 30, SEQ ID NO: 31, SEQ ID NO: 32 and SEQ ID NO: 33), the complete 5.8S rRNA (SEQ ID NO: 3 and SEQ ID NO: 34) and the complete 5S rRNA (SEQ ID NO: 5 and SEQ ID NO: 35) for 20 cycles. A 5-µl aliquot of each PCR reaction was analyzed by ethidium bromide stained agarose gel electrophoresis shown in FIG. 12B.

Figure 12B:
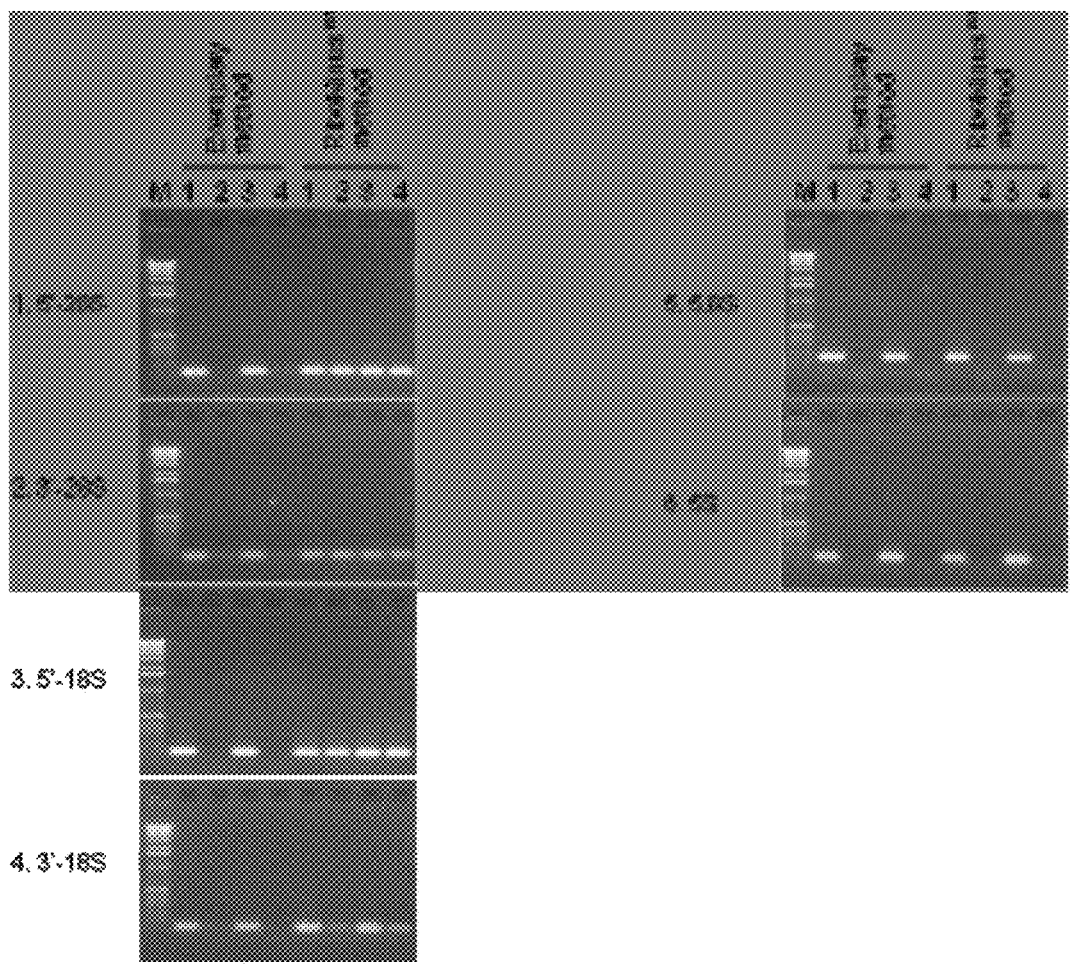
FIG. 12B shows Lane M—DNA molecular weight ladder; Lane 1—PCR results for intact HeLa total RNA minus subtraction; Lane 2—PCR results for intact HeLa total RNA plus subtraction; Lane 3—PCR results for fragmented HeLa total RNA minus subtraction; and Lane 4—PCR results for fragmented HeLa total RNA plus subtraction; Panel 1—5'-28S rRNA; Panel 2—3'-28S rRNA; Panel 3—5'-18S rRNA; Panel 4—3'-18S rRNA; Panel 5—5.8S rRNA; and Panel 6—5S rRNA.

FIG. 12B, Lanes 2 and 4 show the PCR results for 28S rRNA (Panels 1 and 2), 18S rRNA (Panel 3 and 4), 5.8S rRNA (Panel 5) and 5S rRNA (Panel 6) for the intact and fragmented HeLa total RNA, respectively following rRNA subtraction using the Exemplary Method and the RiboMinus™ Eukaryote Kit for RNA-Seq method. The corresponding non-rRNA-subtracted control reactions are shown in Lanes 1 and 3. It is evident from the results that there is overall excellent subtraction of the 28S rRNA (Panels 1 and 2) and 18S rRNA (Panel 3 and 4) sequences contained in both the intact and fragmented total RNA samples using the Exemplary Method (Exemplary Method Panel) but not the RiboMinus™ Eukaryote Kit for RNA-Seq method (RiboMinus™ Panel). However, both methods showed similar removal of the 5.8S (Panel 5) and 5S rRNA sequences (Panel 6).

Figure 12C:
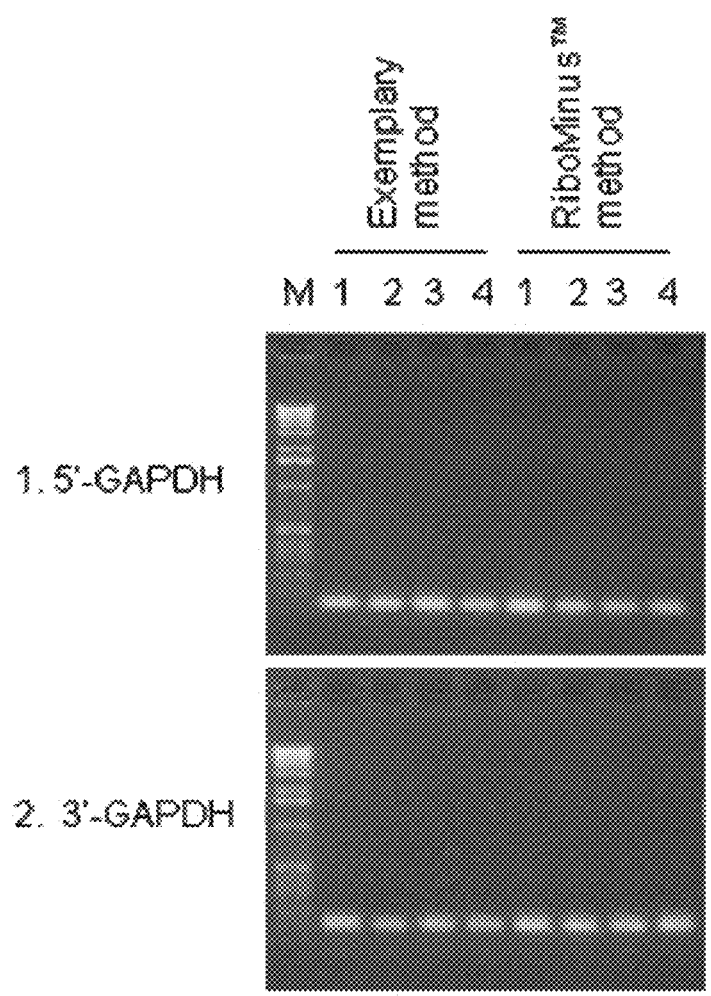
FIG. 12C shows Lane M—DNA molecular weight ladder; Lane 1—PCR results for intact HeLa total RNA minus subtraction; Lane 2—PCR results for intact HeLa total RNA plus subtraction; Lane 3—PCR results for fragmented HeLa total RNA minus subtraction; Lane 4—PCR results for fragmented HeLa total RNA plus subtraction; Panel 1—5'-GAPDH; and Panel 2—3'-GAPDH.

In addition, PCR primers specific for the terminal 5' and 3' regions of GAPDH (SEQ ID NO: 36, SEQ ID NO: 37, SEQ ID NO: 38: 5'-CACAAGAGGAAGAGAGAGA CCCTCA and SEQ ID NO: 39: 5'-TTGATGGTACAT-GACAAGGTGCGG) mRNA was used in PCR (GAPDH: 24 cycles) with the random primed cDNA templates and a 5-µl aliquot of each PCR reaction was analyzed by ethidium bromide stained agarose gel electrophoresis as shown in FIG. 12C. It is clearly evident from the PCR results that there is no obvious reduction in the amount of mRNA for GAPDH (Panels 1 and 2) for both methods with either the intact or fragmented HeLa total RNA (Lanes 2 and 4) compared to the non-rRNA-subtracted samples (Lanes 1 and 3), respectively. Overall, these results demonstrate a clear benefit of the Exemplary Method in the removal of 18S and 28S rRNA sequences independent of the state (intact or fragmented) of the total RNA sample compared to the RiboMinus™ Eukaryote Kit for RNA-Seq method. In fact, even for the intact total RNA sample, the Exemplary method appeared to be more efficient at removal of 18S and 28S rRNA sequences likely due, at least in part, to the fact that there is invariably some degree of fragmented rRNA in even a most intact total RNA sample that would not be removed by the RiboMinus™ method. In fact, the RiboMinus™ Eukaryote Kit for RNA-Seq method clearly states that this method requires use of only high-quality total RNA samples.

Next, the random primed cDNA samples were analyzed by QPCR as follows: The cDNA samples were diluted to anywhere from 2-fold to 10-fold depending on the starting amount. Then, 1 µl of each dilution was added to a 25 µl qPCR reaction comprising 1× FS PreMix E (GREEN), 12.5 pmole of forward and reverse PCR primers and 1 unit of FS Enzyme Mix. The cycling conditions were 98° C. for 2 minutes, followed by 40-45 cycles of 98° C. for 5 seconds, 60° C. for 15 seconds and 72° C. for 30 seconds using the Bio-Rad iCycler (Bio-Rad, Hercules, Calif.). The following QPCR primer pairs were used for 18S (SEQ. ID. No. 30: SEQ. ID. No. 31, SEQ. ID. No. 52: 5'-CTTAGAGGGA- CAAGTGGCG, SEQ. ID. No. 53: 5'-GTAGGGTAGGCA-CACGCTGA, SEQ. ID. No. 54: 5'-GAAACT-TAAAGGAATTGACGGAAG, SEQ. ID. No. 55: 5'-GAATCGAGAAAGAGCTATCAATC, SEQ. ID. No. 56: 5'-CGATTGGATGGTTTAGTGAGG and SEQ. ID. No. 57: 5'-CCTTGTTACGACTTTTACTTCCTCTAG), 28S (SEQ. ID. No. 58: 5'-GCCGAAACGATCTCAACCTA, SEQ. ID. No. 59: 5'-CGCCAGTTCTGCTTACCAAA, SEQ. ID. No. 60: 5'-CGGACCAAGGAGTCTAACA, SEQ. ID. No. 61: 5'-CAGGCATAGTTCACCATCTTTCG, SEQ. ID. No. 62: 5'-GGAGAGGGTGTAAATCTCGC, SEQ. ID. No. 63: 5'-GCCGACTTCCCTTACCTACA, SEQ. ID. No. 64: 5'-GTGTCAGAAAAGTTACCACAGG, SEQ. ID. No. 65: 5'-GGCGAATTCTGCTTCACAATGATAG, SEQ. ID. No. 66: 5'-GGGAGTAACTATGACTCTCTTAAGGT, SEQ. ID. No. 67: 5'-TTGGCTGTGGTTTCGCTGGAT, SEQ. ID. No. 68:5'-GTGAACAGCAGTTGAACATGG and SEQ. ID. No. 69:5'-CTTCACAAAGAAAAGAGAACTCTCCC), 5.8S (SEQ. ID. No. 70: 5'-CGACTCTTAGCGGTGGATCA and SEQ. ID. No. 71: 5'-AAGCGACGCTCAGACAG) and 5S (SEQ. ID. NO. 5 and SEQ. ID. No. 72: 5'-AAAGCCTA-CAGCACCCGGTATTC) rRNA sequences.

The QPCR results are shown in Table 2 below:

TABLE 2

Percentage Ribosomal RNA Reduction

| | Exemplary Method | | RiboMinus ™ Method | |
|---|---|---|---|---|
| QPCR Primer Sets | Intact Hela total RNA (2.5 µg) | Frag- mented Hela total RNA (2.5 µg) | Intact Hela total RNA (2.5 µg) | Frag- mented Hela total RNA (2.5 µg) |
| 18S.5' (nt 100-nt 247) | >99.9% | >99.9% | 93.30% | 50% |
| 18S.3' (nt 1544-nt 1663) | >99.9% | >99.9% | 97.10% | 81.10% |
| 18S.F3/R3 (nt 1288-nt 1417) | >99.9% | >99.9% | 96.40% | 34% |
| 18S.F4/R4 (nt 1818-nt 1937) | >99.9% | >99.9% | 97.40% | 88.30% |
| 28S 3.5K (nt 1748-nt 1867) | >99.9% | >99.9% | 85.60% | 0% |
| 28S #2 (nt 1324-nt 1530) | >99.9% | 99.60% | 92.80% | 90.50% |
| 28S.F5/R5 (nt 4341-nt 4456) | >99.9% | >99.9% | 93.80% | 78.20% |
| 28S.5'#2 (nt 2740-nt 2843) | >99.9% | >99.9% | 92.80% | 29.30% |
| 28S.F3/R3 (nt 2401-nt 2630) | >99.9% | >99.9% | 83.50% | 0% |
| 28S.F4/R4 (nt 3732-nt 3851) | >99.9% | >99.9% | 82.30% | 0% |
| 5.8S (nt 1-nt 157) | >99.9% | >99.9% | 99.40% | 99.60% |
| 5S (nt 1-nt 121) | 96.80% | 97.80% | 91.80% | 88.90% |

Clearly, from the results in Table 2, the exemplary method was significantly more efficient at removal of all ribosomal RNA sequences independent of the primer sets used for both 28S and 18S rRNA sequences with either intact or fragmented total RNA. Whereas, for the RiboMinus™ method with the fragmented RNA, there was little or no ribosomal subtraction depending on the location of the different primer sets for both 28S and 18S rRNA sequences.

Example 13

Significant Reduction of rRNA Background and Improvement in Uniquely Mappable Reads Using rRNA Removal Method Disclosed Herein Compared to the RiboMinus™ Method Intact and partially fragmented Universal Human Reference RNA (UHRR) (2×2.5 µg each) were treated with either the method as described in Example 9 above or the RiboMinus™ Eukaryote Kit for RNA-Seq rRNA removal kit. The respective rRNA-depleted samples were pooled and, for each, Illumina RNA-Seq libraries were prepared in triplicate using rRNA-depleted RNA from the equivalent of 1 µg total RNA. Replicates of the respective RNA-Seq libraries were pooled and sequencing was performed using Illumina® GAIIx next generation sequencer with 36-nt reads. The data were analyzed using Illumina's Pipeline Eland_rna Module and CASAVA Software as well as the TopHat Software for mapping splice junctions (see http:// followed by "tophat.cb-cb.umd.edu/index.html"). The mapping results showed that rRNA background was significantly reduced by the methods described in Example 9 compared to the RiboMinus™ method (see Table 3 below). In addition, the uniquely mappable sequences not including rRNA sequences were significantly increased (Table 3) in the sample treated with the methods as described in Example 9 compared to the RiboMinus™. Furthermore, for the fragmented samples, the Example 9 methods considerably outperformed the competitive kit, both in terms of reducing rRNA background and improving the uniquely mappable sequences (Table 3).

TABLE 3

| Total RNA Sample | rRNA Removal Method | % rRNA Background | % Uniquely Mappable Sequences |
|---|---|---|---|
| Intact UHRR | Example 9 | 1.4% | 58.1% |
| Intact UHRR | RiboMInus ™ | 18.4% | 51.4% |
| Fragmented UHRR | Example 9 | 2.1% | 59.6% |
| Fragmented UHRR | RiboMInus ™ | 63.3% | 24.6% |

Table 3 show that the rRNA removal methods described in Example 9 significantly reduces rRNA background and improves RNA-Seq results. Intact and partially fragmented Universal Human Reference RNA (UHRR) was treated with either the method from Example 9 or the commercial kit (RiboMinus™ method). The rRNA-depleted RNAs were then used to prepare RNA-Seq libraries that were sequenced on an Illumina® GAIIx sequencer.

Example 14

Prophetic Example for Plant rRNA Removal

Plants generally comprises rRNA sequences corresponding to chloroplast, mitochondrial and of nuclear origins. For chloroplast origin, the rRNA comprise 23S, 16S, 5S and 4.5S sequences (e.g. *Arabidopsis thaliana*; Accession # AP000423.1); for mitochondrial origin, the rRNA comprise 18S and 5S sequences (e.g., *Arabidopsis thaliana*; Accession # Y08501.2) and for nuclear origin, the rRNA comprise 25/26S, 17/18S and 5.8S sequences (e.g. *Arabidopsis thaliana*; AC006837.16). PCR templates corresponding to each of the plant rRNA sequence could be synthesized (in full or in part), as well as the respective biotinylated rRNA sequences as described in Example 1 for *E. coli*.

The respective biotinylated antisense could then be mixed either in a single ratio or several different ratios in order to efficiently remove all rRNA sequences from the different plant tissues (e.g. leaf, root, stem etc.) where it is known that the representation of the different rRNA are present in varying amounts, especially dependent on the chloroplast content. It is contemplated that the various plant rRNA sequences will be effectively removed similar to that described for human and *E. coli* rRNA sequences as in Examples 5-12 herein.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, internet web sites, and the like) cited in the present application is incorporated herein by reference in its entirety.

The invention claimed is:

1. A composition comprising antisense rRNA molecules complementary to at least 95% of a full-length sequence of at least one rRNA molecule selected from the group consisting of 28S, 26S, 25S, 18S, 5.8S, and 5S eukaryotic cytoplasmic rRNA molecules, 12S and 16S eukaryotic mitochondrial rRNA molecules, 23S, 16S, 4.5S, and 5S eukaryotic chloroplast rRNA molecules, and 23S, 16S, and 5S prokaryotic rRNA molecules, wherein the antisense rRNA molecules comprise affinity tags at a ratio of at least eight affinity tags per every 100 nucleobases of the antisense rRNA molecules.

2. The composition of claim 1, wherein the antisense rRNA molecules are complementary to multiple different rRNA molecules.

3. The composition of claim 1, wherein the at least one rRNA molecule is selected from the group consisting of 28S, 26S, 25S, 18S, 5.8S, and 5S eukaryotic cytoplasmic rRNA molecules, 12S and 16S eukaryotic mitochondrial rRNA molecules, and 23S, 16S, 4.5S, and 5S eukaryotic chloroplast rRNA molecules.

4. The composition of claim 1, wherein the at least one rRNA molecule is selected from the group consisting of:
   (a) at least four rRNA molecules selected from the group consisting of 28S, 26S, 25S, 18S, 5.8S, and 5S eukaryotic cytoplasmic rRNA molecules;
   (b) two rRNA molecules consisting of 12S and 16S eukaryotic mitochondrial rRNA molecules;
   (c) four rRNA molecules consisting of 16S, 23S, 4.5S, and 5S eukaryotic chloroplast rRNA molecules; and
   (d) three rRNA molecules consisting of 23S, 16S, and 5S prokaryotic rRNA molecules.

5. The composition of claim 1, wherein the at least one rRNA molecule is selected from the group consisting of 28S, 26S, 25S, 18S, 5.8S, and 5S eukaryotic cytoplasmic rRNA molecules and 12S and 16S eukaryotic mitochondrial rRNA molecules.

6. The composition of claim 1, wherein the at least one rRNA molecule includes:
   (a) both the 28S and 18S rRNA molecules, or
   (b) (i) the 25S rRNA molecule or the 26S rRNA molecule, and (ii) the 16S rRNA molecules.

7. The composition of claim 1, wherein the at least one rRNA molecule:
   (a) comprises both the 5.8S rRNA and the 5S rRNA molecules, and/or
   (b) comprises both the 12S and 16S eukaryotic mitochondrial rRNA molecules, and/or
   (c) is selected from the group consisting of 16S, 23S, 4.5S, and 5S eukaryotic chloroplast rRNA molecules.

8. The composition of claim 1, wherein the composition comprises antisense rRNA molecules complementary to at least one eukaryotic rRNA molecule and antisense rRNA molecules complementary to at least one prokaryotic rRNA molecule.

9. The composition of claim 1, wherein the at least one rRNA molecule comprises 18S, 5.8S, and 5S eukaryotic cytoplasmic rRNA molecules.

10. The composition of claim 1, wherein the at least one rRNA molecule comprises 23S and 16S prokaryotic rRNA molecules.

11. The composition of claim 10, wherein the at least one rRNA molecule further comprises the 5S prokaryotic rRNA molecule.

12. The composition of claim 1, wherein the at least one rRNA molecule comprises the 28S and 18S eukaryotic cytoplasmic rRNA molecules.

13. The composition of claim 1, wherein the at least one rRNA molecule comprises the 28S, 18S, 5.8S, and 5S eukaryotic cytoplasmic rRNA molecules.

14. The composition of claim 1, wherein the affinity tag comprises biotin.

15. The composition of claim 1, wherein the affinity tags are associated with at least one nucleobase selected from the group consisting of adenine, cytosine, guanine, and uracil.

16. A kit comprising:
   (a) the composition of claim 1 and
   (b) at least one component selected from the group consisting of:
      (i) a binding matrix comprising affinity tag-binding molecules;
      (ii) a control sample comprising total RNA from a cell or tissue sample;
      (iii) a solution comprising an RNase inhibitor;
      (iv) an RNase-free binding matrix wash solution;
      (v) a volume of RNase-free water;
      (vi) a hybridization buffer;
      (vii) a total RNA purification reagent; and
      (viii) an RNase-free binding matrix resuspension solution.

17. The kit of claim 16, wherein the at least one component comprises the binding matrix.

18. The kit of claim 16, wherein the at least one component comprises the control sample or the solution comprising the RNase inhibitor.

* * * * *

UNITED STATES PATENT AND TRADEMARK OFFICE
CERTIFICATE OF CORRECTION

PATENT NO. : 10,435,683 B2  
APPLICATION NO. : 15/688600  
DATED : October 8, 2019  
INVENTOR(S) : Roy R. Sooknanan Page 1 of 1

It is certified that error appears in the above-identified patent and that said Letters Patent is hereby corrected as shown below:

On the Title Page

Column 1, Item (73), Assignee, Line 1, replace "EPICCENTRE" with EPICENTRE

Signed and Sealed this  
Tenth Day of December, 2019

Andrei Iancu  
*Director of the United States Patent and Trademark Office*